US006894050B2

(12) United States Patent
Chiang et al.

(10) Patent No.: US 6,894,050 B2
(45) Date of Patent: May 17, 2005

(54) 5-HT RECEPTOR LIGANDS AND USES THEREOF

(75) Inventors: Phoebe Chiang, East Lyme, CT (US); William A. Novomisle, Stonington, CT (US); Willard M. Welch, Jr., Mystic, CT (US); Angel Guzman-Perez, Stonington, CT (US); Paul A. DaSilva-Jardine, Killingworth, CT (US); Ravi S. Garigipati, South Glastonbury, CT (US); Kevin K. Liu, East Lyme, CT (US)

(73) Assignee: Pfizer Inc., New York, NY (US)

( * ) Notice: Subject to any disclaimer, the term of this patent is extended or adjusted under 35 U.S.C. 154(b) by 321 days.

(21) Appl. No.: 10/163,881

(22) Filed: Jun. 5, 2002

(65) Prior Publication Data

US 2003/0125334 A1 Jul. 3, 2003

Related U.S. Application Data

(60) Provisional application No. 60/299,953, filed on Jun. 21, 2001.

(51) Int. Cl.[7] .................. C07D 241/20; C07D 401/12; C07D 409/12; A61K 31/497; A61P 25/28
(52) U.S. Cl. .................................. 514/252.11; 544/357
(58) Field of Search ...................... 544/357; 514/252.11

(56) References Cited

U.S. PATENT DOCUMENTS

| | | | |
|---|---|---|---|
| 4,081,542 A | 3/1978 | Lumma et al. | 424/250 |
| 4,435,401 A | 3/1984 | Campbell et al. | 424/251 |
| 5,447,931 A | 9/1995 | Baroni et al. | 514/252 |
| 6,593,330 B2 * | 7/2003 | Nilsson | 514/252.11 |

FOREIGN PATENT DOCUMENTS

| | | | | |
|---|---|---|---|---|
| WO | WO 0028993 | 5/2000 | ......... | A61K/31/495 |
| WO | WO 0044753 | 8/2000 | ......... | C07D/487/04 |
| WO | WO 0076984 | 12/2000 | ......... | C07D/241/18 |
| WO | WO 0208178 | 1/2002 | ......... | C07C/311/51 |
| WO | WO 0240456 | 5/2002 | ......... | C07D/241/18 |
| WO | WO 0240457 | 5/2002 | ......... | C07D/241/18 |

OTHER PUBLICATIONS

Lumma et al., *Journal of Medicinal Chemistry* "Piperazinylpyrazines with Central Serotoninmimetic Activity" 21 (6) 536–542 (1978).

* cited by examiner

*Primary Examiner*—Richard L. Raymond
*Assistant Examiner*—Hong Liu
(74) *Attorney, Agent, or Firm*—Peter C. Richardson; Gregg C. Benson; Arlene K. Musser

(57) ABSTRACT

Compounds of Formula (IA) that act as 5-HT receptor ligands and their uses in the treatment of diseases linked to the activation of 5-HT$_2$ receptors in animals are described herein

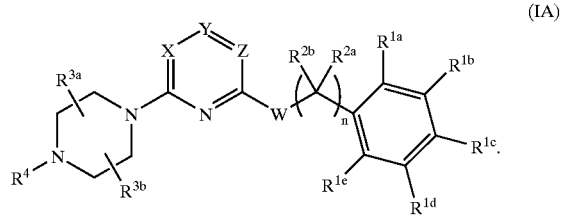

(IA)

11 Claims, No Drawings

5-HT RECEPTOR LIGANDS AND USES THEREOF

This application claims the benefit of U.S. Provisional Ser. No. 60/299,953 filed Jun. 21, 2001 and incorporated herein by reference.

FIELD OF THE INVENTION

The present invention relates to pyrazine compounds that act as 5-HT receptor ligands, in particular 5-$HT_{2c}$ receptor ligands, and their uses in the prevention or treatment of diseases linked to the activation of 5-$HT_{2c}$ receptors in animals.

BACKGROUND

Receptors for serotonin (5-hydroxytryptamine, 5-HT) are an important class of G protein-coupled receptors. Serotonin is thought to play a role in processes related to learning and memory, sleep, thermoregulation, mood, motor activity, pain, sexual and aggressive behaviors, appetite, neurodegenerative regulation, and biological rhythms. As expected, serotonin is linked to pathophysiological conditions such as anxiety, depression, obsessive-compulsive disorders, schizophrenia, suicide, autism, migraine, emesis, alcoholism and neurodegenerative disorders.

The serotonin receptors are currently classified into seven subfamilies (5-$HT_1$ through 5-$HT_7$). See, Hoyer, D., et al., "VII International Union of Pharmacology classification of receptors for 5-hydroxytryptamine", *Pharmacol. Rev.*, 56, 157–203 (1994). The subfamilies have been further divided into subtypes. For example, the 5-$HT_2$ receptor is currently divided into three subtypes: 5-$HT_{2a}$, 5-$HT_{2b}$ and 5-$HT_{2c}$. The three subtypes of 5-$HT_2$ receptors are linked to phospholipase C with the generation of two second messengers, diacylglycerol (which activates protein kinase C) and inositol trisphosphate (which releases intracellular stores of $Ca^{2+}$). The 5-$HT_{2c}$ receptors have a very high density in the choroid plexus, an epithelial tissue that is the primary site of cerebrospinal fluid production. See, Sanders-Bush, E. and S. E. Mayer, "5-Hydroxytryptamine (Serotonin) Receptor agonists and Antagonists", *Goodman & Gilman's The Pharmacological Basis of Therapeutics*, Chapter 11, 9th Ed., McGraw-Hill, New York, N.Y. (1996).

Julius, et al., isolated and characterized the 5-$HT_{2c}$ receptor and later reported that transgenic mice lacking the 5-$HT_{2c}$ receptor exhibit seizures and an eating disorder resulting in increased consumption of food (see, U.S. Pat. Nos. 4,985,352 and 5,698,766, respectively). Consequently, compounds selective for the 5-$HT_{2c}$ receptor may provide useful therapies for the treatment of seizure and eating disorders without the side effects typically associated with nonselectivity of the ligand.

Several compounds have been proposed as 5-$HT_{2c}$ receptor agonists or antagonists for use in the treatment of obesity and other related diseases associated with decreased neurotransmission of serotonin in mammals. See, e.g., EP 863136 (azetidine and pyrrolidine derivatives); EP 657426 (tricyclic pyrrole derivatives); EP 655440 (substituted 1-aminoethyl indoles); EP 572863 (pyrazinoindole derivatives); WO98/030548 (aminoalkylindazole compounds); WO 98/56768 (tricyclic pyrrole and pyrazole derivatives); WO 99/43647 (azetidine and pyrrolidine derivatives); WO 99/58490 (aryl-hydronaphthalenalkanamine derivatives); WO 00/12475 (indoline derivatives); WO 00/12482 (indazole derivatives); WO 00/12502 (pyrroloquinoline derivatives); WO 00/12510 (pyrroloindole, pyridoindole and azepinoindole derivatives); WO 00/28993 (naphthylacetylpiperazine derivatives); WO 00/44737 (aminoalkylbenzofuran derivatives); and WO 00/76984 (2,3-disubstituted pyrazines).

The non-selectivity of ligands for the various 5-HT receptors remains a challenge. It is suspected that the non-selectivity of some ligands contributes to various adverse side effects such as hallucinations and cardiovascular complications. Therefore, there remains a need for selective 5-$HT_{2c}$ receptor ligands.

SUMMARY

The present invention provides compounds of Formula (IA) which are useful as 5-$HT_2$ receptor ligands (in particular, 5-$HT_{2a}$ and 5-$HT_{2c}$ receptor ligands).

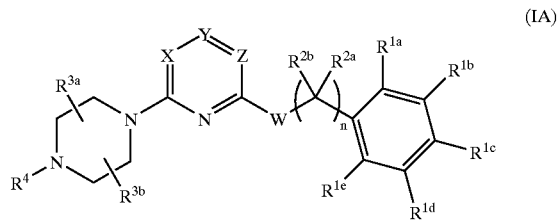

(IA)

wherein
Y is nitrogen;
X and Z are each independently CR, where R for each occurrence is hydrogen, halogen, ($C_1$–$C_4$)alkyl, amino, or ($C_1$–$C_4$)alkylamino;
W is oxy, thio, amino, ($C_1$–$C_4$)alkylamino, or acetylamino;
at least one of $R^{1a}$, $R^{1b}$, $R^{1d}$, and $R^{1e}$ is independently selected from the group consisting of halogen, nitro, amino, ($C_1$–$C_4$)alkylamino, cyano, —C(O)$NH_2$, ($C_1$–$C_4$)alkyl, halo-substituted($C_1$–$C_4$)alkyl, ($C_1$–$C_4$)alkoxy, and halo-substituted($C_1$–$C_4$)alkoxy, or $R^{1a}$ and $R^{1b}$ taken together form a five- or six-membered, aromatic or partially or fully saturated fused ring, or $R^{1a}$ taken together with $R^{2a}$ or $R^{2b}$ forms a five- or six-membered, fully saturated fused ring;
$R^{1c}$ is hydrogen;
$R^{2a}$ and $R^{2b}$ are each independently hydrogen, ($C_1$–$C_4$) alkyl, partially or fully saturated ($C_3$–$C_6$)cycloalkyl, or one of which taken together with $R^{1a}$ forms a five- or six-membered, fully saturated fused ring;
n is 0, 1, or 2;
$R^{3a}$ and $R^{3b}$ are each independently hydrogen, halogen, ($C_1$–$C_4$)alkyl, or ($C_1$–$C_4$)alkyl substituted with hydroxy, fluoro, or ($C_1$–$C_4$)alkoxy;
$R^4$ is hydrogen, hydroxy, ($C_1$–$C_4$)alkyl, ($C_1$–$C_4$)alkyl substituted with hydroxy or cyano, ($C_1$–$C_4$)alkylcarbonyl, ($C_1$–$C_4$)alkoxy, ($C_1$–$C_4$)alkoxy-carbonyl, ($C_3$–$C_4$)alkenyl, or an amino-protecting group;
a nitrogen oxide thereof, a prodrug of the compound or the nitrogen oxide; a pharmaceutically acceptable salt of the compound, the nitrogen oxide, or the prodrug, or a solvate or hydrate of the compound, the nitrogen oxide, the prodrug, or the salt.

Preferred compounds of Formula (IA) are those where Y is nitrogen; X and Z are each independently CR, where R is hydrogen, chloro, fluoro, methyl, or amino;
(i) $R^{1a}$ is halogen, ($C_1$–$C_4$)alkyl, trifluoromethyl, methoxy, or trifluoromethoxy, and $R^{1b}$, $R^{1d}$ and $R^{1e}$ are each hydrogen,
(ii) $R^{1b}$ is halogen, methyl, methoxy, nitro, amino, cyano, or —C(O)$NH_2$ and $R^{1a}$, $R^{1d}$ and $R^{1e}$ are each hydrogen, (iii) $R^{1a}$ and $R^{1b}$ are each independently halogen or methyl and $R^{1d}$ and $R^{1e}$ are each hydrogen, (iv) $R^{1b}$ and $R^{1d}$ are each independently halogen or methyl and $R^{1a}$ and $R^{1e}$ are each hydrogen, (v) $R^{1a}$ and $R^{1d}$ are each independently halogen or methyl and $R^{1b}$ and $R^{1e}$ are each hydrogen, (vi) $R^{1a}$ and $R^{1e}$ are each independently halogen or methyl and $R^{1b}$ and $R^{1d}$ are each hydrogen, or (vii) $R^{1a}$, $R^{1b}$ and $R^{1d}$ are each independently halogen or methyl and $R^{1e}$ is hydrogen;

W is oxy, thio, amino, or acetylamino; n is 1; $R^{2a}$ and $R^{2b}$ are each independently methyl or hydrogen; $R^{3a}$ and $R^{3b}$ are each independently hydrogen or $(C_1-C_2)$alkyl (preferably (2R)-methyl or (2R)-ethyl); and $R^4$ is hydrogen or $(C_1-C_4)$ alkyl; a nitrogen oxide thereof, a prodrug of the compound or the nitrogen oxide; a pharmaceutically acceptable salt of the compound, the nitrogen oxide, or the prodrug, or a solvate or hydrate of the compound, the nitrogen oxide, the prodrug, or the salt.

More preferred compounds are those where Y is N; X and Z are each independently CR, where R is hydrogen; (i) $R^{1a}$ is halogen, methyl, or trifluoromethyl and $R^{1b}$, $R^{1d}$ and $R^{1e}$ are each hydrogen, (ii) $R^{1b}$ is halogen, methyl, nitro, amino, cyano or —C(O)NH$_2$ and $R^{1a}$, $R^{1d}$ and $R^{1e}$ are each hydrogen, (iii) $R^{1b}$ and $R^{1d}$ are each independently halogen or methyl and $R^{1a}$ and $R^{1e}$ are each hydrogen, or (iv) $R^{1a}$ and $R^{1d}$ are each independently halogen or methyl and $R^{1b}$ and $R^{1e}$ are each hydrogen; W is oxy, thio, amino, or acetylamino; n is 1; $R^{2a}$ and $R^{2b}$ are each independently methyl or hydrogen; $R^{3a}$ is hydrogen, (2R)-methyl, or (2R)-ethyl; $R^{3b}$ is hydrogen; and $R^4$ is hydrogen; a nitrogen oxide thereof, a prodrug of the compound or the nitrogen oxide; a pharmaceutically acceptable salt of the compound, the nitrogen oxide, or the prodrug, or a solvate or hydrate of the compound, the nitrogen oxide, the prodrug, or the salt.

Most preferred are those compounds where Y is N, X and Z are each independently CR, where R for each occurrence is hydrogen or methyl; (i) $R^{1a}$ is halogen, or methyl and $R^{1b}$, $R^{1d}$ and $R^{1e}$ are each hydrogen, (ii) $R^{1b}$ is halogen, methyl, nitro, amino, cyano, or —C(O)NH$_2$ and $R^{1a}$, $R^{1d}$ and $R^{1e}$ are each hydrogen, (iii) $R^{1b}$ and $R^{1d}$ are each independently halogen or methyl and $R^{1a}$ and $R^{1e}$ are each hydrogen, or (iv) $R^{1a}$ and $R^{1d}$ are each independently halogen or methyl and $R^{1b}$ and $R^{1e}$ are each hydrogen; W is oxy, amino, or acetylamino; n is 1; $R^{2a}$ and $R^{2b}$ are each independently methyl or hydrogen; $R^{3a}$ is hydrogen, (2R)-methyl, or (2R)-ethyl; and $R^{3b}$ is hydrogen; and $R^4$ is hydrogen; a nitrogen oxide thereof, a prodrug of the compound or the nitrogen oxide; a pharmaceutically acceptable salt of the compound, the nitrogen oxide, or the prodrug, or a solvate or hydrate of the compound, the nitrogen oxide, the prodrug, or the salt.

Non-limiting examples of preferred compounds of Formula (IA) include; 6'-(3-chloro-benzyloxy)-3,4,5,6-tetrahydro-2H-[1,2']bipyrazinyl; 6'-(3-chloro-benzyloxy)-2-ethyl-3,4,5,6-tetrahydro-2H-[1,2']bipyrazinyl; 6'-(3-fluoro-benzyloxy)-3,4,5,6-tetrahydro-2H-[1,2']bipyrazinyl; 6'-(3-chloro-benzyloxy)-(2R)-methyl-3,4,5,6-tetrahydro-2H-[1,2']bipyrazinyl; 6'-(3-fluoro-benzyloxy)-(2R)-methyl-3,4,5,6-tetrahydro-2H-[1,2']bipyrazinyl; 6'-(3-chloro-benzyloxy)-3,4,5,6-tetrahydro-2H-[1,2']bipyrazinyl 4'-oxide; 6'-(2,5-dichloro-benzyloxy)-3,4,5,6-tetrahydro-2H-[1,2']bipyrazinyl; 6'-(2-fluoro-benzyloxy)-3,4,5,6-tetrahydro-2H-[1,2']bipyrazinyl; 6'-(3-nitro-benzyloxy)-3,4,5,6-tetrahydro-2H-[1,2']bipyrazinyl; 3-(3,4,5,6-tetrahydro-2H-[1,2']bipyrazinyl-6'-yloxymethyl)-benzonitrile; 6'-(2,5-difluoro-benzyloxy)-3,4,5,6-tetrahydro-2H-[1,2']bipyrazinyl; 5'-bromo-6'-(3-chloro-benzyloxy)-3,4,5,6-tetrahydro-2H-[1,2']bipyrazinyl; 6'-(3-bromo-benzyloxy)-3,4,5,6-tetrahydro-2H-[1,2']bipyrazinyl; 3-(3,4,5,6-tetrahydro-2H-[1,2']bipyrazinyl-6'-yloxymethyl)-phenylamine; 6'-(2-methyl-benzyloxy)-3,4,5,6-tetrahydro-2H-[1,2']bipyrazinyl; 6'-(3-chloro-benzyloxy)-5'-fluoro-3,4,5,6-tetrahydro-2H-[1,2']bipyrazinyl; 5'-chloro-6'-(3-chloro-benzyloxy)-3,4,5,6-tetrahydro-2H-[1,2']bipyrazinyl; 6'-(indan-(1S)-yloxy)-3,4,5,6-tetrahydro-2H-[1,2']bipyrazinyl; 6'-(3-methy-benzyloxy)-3,4,5,6-tetrahydro-2H-[1,2']bipyrazinyl; 6'-(3-chloro-benzyloxy)-3,4,5,6-tetrahydro-2H-[1,2']bipyrazinyl-3'-ylamine; 6'-(2-chloro-benzyloxy)-3,4,5,6-tetrahydro-2H-[1,2']bipyrazinyl; 6'-[2-(3-chloro-phenyl)-ethoxy]-3,4,5,6-tetrahydro-2H-[1,2']bipyrazinyl; 6'-(2-chloro-benzyloxy)-(2R)-methyl-3,4,5,6-tetrahydro-2H-[1,2']bipyrazinyl; 6'-(3,4-difluoro-benzyloxy)-3,4,5,6-tetrahydro-2H-[1,2']bipyrazinyl; 6'-(3,5-difluoro-benzyloxy)-3,4,5,6-tetrahydro-2H-[1,2']bipyrazinyl; (3-fluoro-benzyl)-(3,4,5,6-tetrahydro-2H-[1,2']bipyrazinyl-6'-yl)-amine; (3-chloro-benzyl)-(3,4,5,6-tetrahydro-2H-[1,2']bipyrazinyl-6'-yl)-amine; (3,5-difluoro-benzyl)-(3,4,5,6-tetrahydro-2H-[1,2']bipyrazinyl-6'-yl)-amine; 3-[(3,4,5,6-tetrahydro-2H-[1,2']bipyrazinyl-6'-ylamino)-methyl]-benzonitrile; (2,5-difluoro-benzyl)-(3,4,5,6-tetrahydro-2H-[1,2']bipyrazinyl-6'-yl)-amine; (3,5-dichloro-benzyl)-(3,4,5,6-tetrahydro-2H-[1,2']bipyrazinyl-6'-yl)-amine; (3-chloro-benzyl)-(2-methyl-3,4,5,6-tetrahydro-2H-[1,2']bipyrazinyl-6'-yl)-amine; (3-fluoro-benzyl)-(2-methyl-3,4,5,6-tetrahydro-2H-[1,2']bipyrazinyl-6'-yl)-amine; (2-chloro-benzyl)-(3,4,5,6-tetrahydro-2H-[1,2']bipyrazinyl-6'-yl)-amine; (2-chloro-6-fluoro-benzyl)-(3,4,5,6-tetrahydro-2H-[1,2']bipyrazinyl-6'-yl)-amine; (2,3-difluoro-benzyl)-(3,4,5,6-tetrahydro-2H-[1,2']bipyrazinyl-6'-yl)-amine; N-(3-chloro-benzyl)-N-(3,4,5,6-tetrahydro-2H-[1,2']bipyrazinyl-6'-yl)-acetamide; 6'-(3-chloro-benzylsulfanyl)-3,4,5,6-tetrahydro-2H-[1,2']bipyrazinyl; and 6'-benzylsulfanyl-3,4,5,6-tetrahydro-2H-[1,2']bipyrazinyl;

a nitrogen oxide thereof, a prodrug of the compound or the nitrogen oxide; a pharmaceutically acceptable salt of the compound, the nitrogen oxide, or the prodrug, or a solvate or hydrate of the compound, the nitrogen oxide, the prodrug, or the salt.

Non-limiting examples of more preferred compounds of Formula (1A) include; 6'-(3-chloro-benzyloxy)-3,4,5,6-tetrahydro-2H-[1,2']bipyrazinyl; 6'-(3-chloro-benzyloxy)-(2R)-methyl-3,4,5,6-tetrahydro-2H-[1,2']bipyrazinyl; 6'-(2-chloro-benzyloxy)-(2R)-methyl-3,4,5,6-tetrahydro-2H-[1,2']bipyrazinyl; 6'-(3-fluoro-benzyloxy)-(2R)-methyl-3,4,5,6-tetrahydro-2H-[1,2']bipyrazinyl; 6'-(2-fluoro-benzyloxy)-3,4,5,6-tetrahydro-2H-[1,2']bipyrazinyl; 6'-(3-fluoro-benzyloxy)-3,4,5,6-tetrahydro-2H-[1,2']bipyrazinyl; 6'-(3-chloro-benzyloxy)-2-ethyl-3,4,5,6-tetrahydro-2H-[1,2']bipyrazinyl; 6'-(2,5-difluoro-benzyloxy)-3,4,5,6-tetrahydro-2H-[1,2']bipyrazinyl; 6'-(2,5-dichloro-benzyloxy)-3,4,5,6-tetrahydro-2H-[1,2']bipyrazinyl; 6'-(3,5-difluoro-benzyloxy)-3,4,5,6-tetrahydro-2H-[1,2']bipyrazinyl; (3-fluoro-benzyl)-(3,4,5,6-tetrahydro-2H-[1,2']bipyrazinyl-6'-yl)-amine; (3-chloro-benzyl)-(3,4,5,6-tetrahydro-2H-[1,2']bipyrazinyl-6'-yl)-amine; (3,5-difluoro-benzyl)-(3,4,5,6-tetrahydro-2H-[1,2']bipyrazinyl-6'-yl)-amine; 3,5-dichloro-benzyl)-(3,4,5,6-tetrahydro-2H-[1,2']bipyrazinyl-6'-yl)-amine; (2-chloro-6-fluoro-benzyl)-(3,4,5,6-tetrahydro-2H-[1,2']bipyrazinyl-6'-yl)-amine; 6'-(3-chloro-benzyloxy)-3,4,5,6-tetrahydro-2H-[1,2']bipyrazinyl 4'-oxide; N-(3-chloro-benzyl)-N-(3,4,5,6-tetrahydro-2H-[1,2']bipyrazinyl-6'-yl)-acetamide; 6'-(3-chloro-benzylsulfanyl)-3,4,5,6-tetrahydro-2H-[1,2']bipyrazinyl; and 6'-(indan-(1S)-yloxy)-3,4,5,6-tetrahydro-2H-[1,2']bipyrazinyl;

a nitrogen oxide thereof, a prodrug of the compound or the nitrogen oxide; a pharmaceutically acceptable salt of the compound, the nitrogen oxide, or the prodrug, or a solvate or hydrate of the compound, the nitrogen oxide, the prodrug, or the salt.

Even more preferred compounds of the present invention include: 6'-(3-chloro-benzyloxy)-3,4,5,6-tetrahydro-2H-[1,2']bipyrazinyl; 6'-(3-fluoro-benzyloxy)-3,4,5,6-tetrahydro-2H-[1,2']bipyrazinyl; 6'-(3-chloro-benzyloxy)-3,4,5,6-tetrahydro-2H-[1,2']bipyrazinyl 4'-oxide; (3-fluoro-benzyl)-(3,4,5,6-tetrahydro-2H-[1,2']bipyrazinyl-6'-yl)-amine; 6'-(3-chloro-benzyloxy)-(2R)-methyl-3,4,5,6-tetrahydro-2H-[1,2']bipyrazinyl; 6'-(3,5-difluoro-benzyloxy)-3,4,5,6-tetrahydro-2H-[1,2']bipyrazinyl; 6'-(2,5-difluoro-benzyloxy)-3,4,5,6-tetrahydro-2H-[1,2']bipyrazinyl; and 6'-(indan-(1S)-yloxy)-3,4,5,6-tetrahydro-2H-[1,2']bipyrazinyl; a prodrug of the compound or the nitrogen oxide; a pharmaceutically acceptable salt of the compound, the nitrogen oxide, or the prodrug, or a solvate or hydrate of the compound, the nitrogen oxide, the prodrug, or the salt.

Preferred salts of the compounds described above include citrates, fumarates, hydrochlorides, L-malates, succinates, D,L-tartrates and more preferred salts include citrates, L-malates and D,L-tartrates.

In yet another embodiment of the present invention, compounds of Formula (IC) are provided.

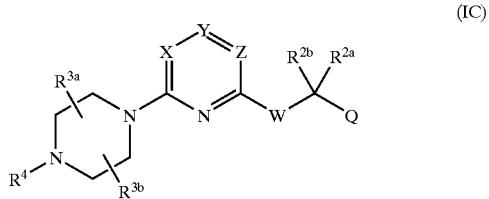

(IC)

wherein
Y is N;
X and Z are each independently CR, where R for each occurrence is hydrogen, halogen, $(C_1-C_4)$alkyl, amino, or $(C_1-C_4)$alkylamino;
W is oxy, thio, amino, $(C_1-C_4)$alkylamino, or acetylamino;
Q is a heteroaryl group selected from the group consisting of pyridin-2-yl, pyridin-3-yl, furan-3-yl, furan-2-yl, thiophen-2-yl, thiophen-3-yl, thiazol-2-yl, pyrrol-2-yl, pyrrol-3-yl, pyrazol-3-yl, quinolin-2-yl, quinolin-3-yl, isoquinolin-3-yl, benzofuran-2-yl, benzofuran-3-yl, isobenzofuran-3-yl, benzothiophen-2-yl, benzothiophen-3-yl, indol-2-yl, indol-3-yl, 2H-imidazol-2-yl, oxazol-2-yl, isoxazol-3-yl, 1,2,4-oxadiazol-3-yl, 1,2,4-oxadiazol-5-yl, 1,3,4-oxadiazol-2-yl, 1,3,4-oxadiazol-5-yl, 1,2,4-triazol-3-yl, 1,2,3-thiadiazol-4-yl, 1,2,3-thiadiazol-5-yl, 1,3,4-thiadiazol-2-yl, 1,3,4-thiadiazol-5-yl, and 1,2,4-oxathiazol-3-yl, where the heteroaryl group is optionally substituted with one to three substituents independently selected from halo, $(C_1-C_4)$alkyl, cyano, nitro, amino, $(C_1-C_4)$alkylamino, or $(C_1-C_4)$alkyoxy;
$R^{2a}$ and $R^{2b}$ are each independently hydrogen, $(C_1-C_4)$alkyl, or partially or fully saturated $(C_3-C_6)$cycloalkyl;
$R^{3a}$ and $R^{3b}$ are each independently hydrogen, halogen, $(C_1-C_4)$alkyl, or $(C_1-C_4)$alkyl substituted with hydroxy, fluoro, or $(C_1-C_4)$alkoxy;
$R^4$ is hydrogen, hydroxy, $(C_1-C_4)$alkyl, $(C_1-C_4)$alkyl substituted with hydroxy or cyano, $(C_1-C_4)$alkylcarbonyl, $(C_1-C_4)$alkoxy, $(C_1-C_4)$alkoxy-carbonyl, or $(C_3-C_4)$alkenyl;
a nitrogen oxide thereof, a prodrug of the compound or the nitrogen oxide; a pharmaceutically acceptable salt of the compound, the nitrogen oxide, or the prodrug, or a solvate or hydrate of the compound, the nitrogen oxide, the prodrug, or the salt.

Non-limiting examples of preferred compounds of Formula (IC) include: 6'-(pyridin-3-ylmethoxy)-3,4,5,6-tetrahydro-2H-[1,2']bipyrazinyl; 2-methyl-6'-(pyridin-3-ylmethoxy)-3,4,5,6-tetrahydro-2H-[1,2']bipyrazinyl; 6'-(thiophen-3-ylmethoxy)-3,4,5,6-tetrahydro-2H-[1,2']bipyrazinyl; 6'-([1,2,3]thiadiazol-4-ylmethoxy)-3,4,5,6-tetrahydro-2H-[1,2']bipyrazinyl; 6'-(6-fluoro-pyridin-2-ylmethoxy)-3,4,5,6-tetrahydro-2H-[1,2']bipyrazinyl; 2-methyl-6'-(6-methyl-pyridin-2-ylmethoxy)-3,4,5,6-tetrahydro-2H-[1,2']bipyrazinyl; 6'-(6-methyl-pyridin-2-ylmethoxy)-3,4,5,6-tetrahydro-2H-[1,2']bipyrazinyl; and 6'-(6-chloro-pyridin-2-ylmethoxy)-3,4,5,6-tetrahydro-2H-[1,2']bipyrazinyl; a nitrogen oxide thereof, a prodrug of the compound or the nitrogen oxide; a pharmaceutically acceptable salt of the compound, the nitrogen oxide, or the prodrug, or a solvate or hydrate of the compound, the nitrogen oxide, the prodrug, or the salt.

Non-limiting examples of more preferred compounds of Formula (1C) include 6'-(6-methyl-pyridin-2-ylmethoxy)-3,4,5,6-tetrahydro-2H-[1,2']bipyrazinyl; 6'-(6-chloro-pyridin-2-ylmethoxy)-3,4,5,6-tetrahydro-2H-[1,2']bipyrazinyl; 6'-(6-fluoro-pyridin-2-ylmethoxy)-3,4,5,6-tetrahydro-2H-[1,2']bipyrazinyl; 2-(6-chloro-pyridin-2-ylmethoxy)-4-piperazin-1-yl-pyrimidine; and 2-methyl-6'-(6-methyl-pyridin-2-ylmethoxy)-3,4,5,6-tetrahydro-2H-[1,2']bipyrazinyl; a nitrogen oxide thereof, a prodrug of the compound or the nitrogen oxide; a pharmaceutically acceptable salt of the compound, the nitrogen oxide, or the prodrug, or a solvate or hydrate of the compound, the nitrogen oxide, the prodrug, or the salt.

Some of the compounds described herein contain at least one chiral center; consequently, those skilled in the art will appreciate that all stereoisomers (e.g., enantiomers and diasteroisomers) of the compounds illustrated and discussed herein are within the scope of the present invention. In addition, tautomeric forms of the compounds are also within the scope of the present invention.

In another embodiment of the present invention, a pharmaceutical composition is provided that comprises (1) a compound of Formula (IA) or (1C), a nitrogen oxide thereof, a prodrug of the compound or the nitrogen oxide; a pharmaceutically acceptable salt of the compound, the nitrogen oxide, or the prodrug, or a solvate or hydrate of the compound, the nitrogen oxide, the prodrug, or the salt, and (2) a pharmaceutically acceptable excipient, diluent, or carrier.

In yet another embodiment of the present invention, a method for treating 5-$HT_2$ (preferably, 5-$HT_{2c}$) receptor-mediated diseases, conditions, or disorders in an animal that includes the step of administering to the animal a therapeutically effective amount of a compound of Formula (IB)

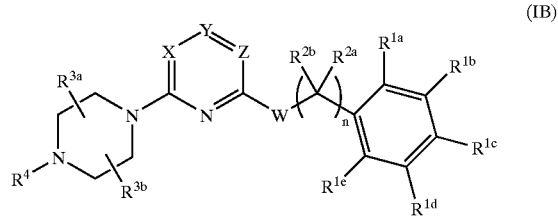

(IB)

wherein
Y is N;
X and Z are each independently CR, where R for each occurrence is hydrogen, halogen (preferably Cl or F), $(C_1-C_4)$alkyl, amino, or $(C_1-C_4)$alkylamino;

W is oxy, thio, amino, $(C_1-C_4)$alkylamino, or acetylamino;

$R^1a$, $R^1b$, $R^{1c}$, $R^{1d}$ and $R^{1e}$ are each independently hydrogen, halogen, nitro, cyano, amino, $(C_1-C_4)$alkylamino, $(C_1-C_4)$alkyl, halo-substituted $(C_1-C_4)$alkyl, $(C_1-C_4)$ alkoxy, halo-substituted $(C_1-C_4)$alkoxy, —C(O)NH$_2$, $R^{1a}$ and $R^{1b}$ taken together form a five- or six-membered, aromatic or partially or fully saturated fused ring, or $R^{1a}$ taken together with $R^{2a}$ or $R^{2b}$ forms a five- or six-membered, fully saturated, fused ring;

$R^{2a}$ and $R^{2b}$ are each independently hydrogen, $(C_1-C_4)$ alkyl, partially or fully saturated $(C_3-C_6)$cycloalkyl, or one of which taken together with $R^{1a}$ forms a five- or six-membered, fully saturated fused ring;

n is 0, 1, or 2;

$R^{3a}$ and $R^{3b}$ are each independently hydrogen, halogen, $(C_1-C_4)$alkyl, $(C_1-C_4)$alkyl substituted with hydroxy, fluoro, or $(C_1-C_4)$alkoxy;

$R^4$ is hydrogen, hydroxy, $(C_1-C_4)$alkyl, $(C_1-C_4)$alkyl substituted with hydroxy or cyano, $(C_1-C_4)$alkylcarbonyl, $(C_1-C_4)$alkoxy, $(C_1-C_4)$alkoxy-carbonyl, or $(C_3-C_4)$ alkenyl;

a nitrogen oxide thereof, a prodrug of said compound or said nitrogen oxide; a pharmaceutically acceptable salt of said compound, said nitrogen oxide, or said prodrug, or a solvate or hydrate of said compound, said nitrogen oxide, said prodrug, or said salt.

Non-limiting examples of preferred compounds of Formula (IB) include 6'-benzyloxy-3,4,5,6-tetrahydro-2H-[1,2'] bipyrazinyl; 6'-(3-chloro-benzyloxy)-3,4,5,6-tetrahydro-2H-[1,2']bipyrazinyl; 6'-(3-chloro-benzyloxy)-2-ethyl-3,4,5,6-tetrahydro-2H-[1,2']bipyrazinyl; 6'-(3-fluoro-benzyloxy)-3,4,5,6-tetrahydro-2H-[1,2']bipyrazinyl; 6'-(3-chloro-benzyloxy)-(2R)-methyl-3,4,5,6-tetrahydro-2H-[1,2'] bipyrazinyl; 6'-(3-fluoro-benzyloxy)-(2R)-methyl-3,4,5,6-tetrahydro-2H-[1,2']bipyrazinyl; 6'-(3-chloro-benzyloxy)-3,4,5,6-tetrahydro-2H-[1,2']bipyrazinyl 4'-oxide; 6'-(2,5-dichloro-benzyloxy)-3,4,5,6-tetrahydro-2H-[1,2'] bipyrazinyl; 6'-(2-fluoro-benzyloxy)-3,4,5,6-tetrahydro-2H-[1,2']bipyrazinyl; 6'-(3-nitro-benzyloxy)-3,4,5,6-tetrahydro-2H-[1,2']bipyrazinyl; 3-(3,4,5,6-tetrahydro-2H-[1,2'] bipyrazinyl-6'-yloxymethyl)-benzonitrile; 6'-(2,5-difluoro-benzyloxy)-3,4,5,6-tetrahydro-2H-[1,2']bipyrazinyl; 5'-bromo-6'-(3-chloro-benzyloxy)-3,4,5,6-tetrahydro-2H-[1,2']bipyrazinyl; 6'-(3-bromo-benzyloxy)-3,4,5,6-tetrahydro-2H-[1,2']bipyrazinyl; 3-(3,4,5,6-tetrahydro-2H-[1,2']bipyrazinyl-6'-yloxymethyl)-phenylamine; 6'-(2-methyl-benzyloxy)-3,4,5,6-tetrahydro-2H-[1,2']bipyrazinyl; 6'-(3-chloro-benzyloxy)-5'-fluoro-3,4,5,6-tetrahydro-2H-[1,2']bipyrazinyl; 5'-chloro-6'-(3-chloro-benzyloxy)-3,4,5,6-tetrahydro-2H-[1,2']bipyrazinyl; 6'-(indan-(1S)-yloxy)-3,4,5,6-tetrahydro-2H-[1,2']bipyrazinyl; 6'-(3-methy-benzyloxy)-3,4,5,6-tetrahydro-2H-[1,2']bipyrazinyl; 6'-(3-chloro-benzyloxy)-3,4,5,6-tetrahydro-2H-[1,2']bipyrazinyl-3'-ylamine; 6'-(2-chloro-benzyloxy)-3,4,5,6-tetrahydro-2H-[1,2']bipyrazinyl; 6'-[2-(3-chloro-phenyl)-ethoxy]-3,4,5,6-tetrahydro-2H-[1,2']bipyrazinyl; 6'-(2-chloro-benzyloxy)-(2R)-methyl-3,4,5,6-tetrahydro-2H-[1,2']bipyrazinyl; 6'-(3,4-difluoro-benzyloxy)-3,4,5,6-tetrahydro-2H-[1,2'] bipyrazinyl; 6'-(3,5-difluoro-benzyloxy)-3,4,5,6-tetrahydro-2H-[1,2']bipyrazinyl; (3-fluoro-benzyl)-(3,4,5,6-tetrahydro-2H-[1,2']bipyrazinyl-6'-yl)-amine; (3-chloro-benzyl)-(3,4,5,6-tetrahydro-2H-[1,2']bipyrazinyl-6'-yl)-amine; (3,5-difluoro-benzyl)-(3,4,5,6-tetrahydro-2H-[1,2']bipyrazinyl-6'-yl)-amine; 3-[(3,4,5,6-tetrahydro-2H-[1,2']bipyrazinyl-6'-ylamino)-methyl]-benzonitrile; (2,5-difluoro-benzyl)-(3,4,5,6-tetrahydro-2H-[1,2']bipyrazinyl-6'-yl)-amine; (3,5-dichloro-benzyl)-(3,4,5,6-tetrahydro-2H-[1,2']bipyrazinyl-6'-yl)-amine; (3-chloro-benzyl)-(2-methyl-3,4,5,6-tetrahydro-2H-[1,2']bipyrazinyl-6'-yl)-amine; (3-fluoro-benzyl)-(2-methyl-3,4,5,6-tetrahydro-2H-[1,2']bipyrazinyl-6'-yl)-amine; (2-chloro-benzyl)-(3,4,5,6-tetrahydro-2H-[1,2']bipyrazinyl-6'-yl)-amine; (2-chloro-6-fluoro-benzyl)-(3,4,5,6-tetrahydro-2H-[1,2']bipyrazinyl-6'yl)-amine; (2,3-difluoro-benzyl)-(3,4,5,6-tetrahydro-2H-[1,2']bipyrazinyl-6'-yl)-amine; N-(3-chloro-benzyl)-N-(3,4,5,6-tetrahydro-2H-[1,2']bipyrazinyl-6'-yl)-acetamide; 6'-(3-chloro-benzylsulfanyl)-3,4,5,6-tetrahydro-2H-[1,2']bipyrazinyl; and 6'-benzylsulfanyl-3,4,5,6-tetrahydro-2H-[1,2'] bipyrazinyl;

a nitrogen oxide thereof, a prodrug of the compound or the nitrogen oxide; a pharmaceutically acceptable salt of the compound, the nitrogen oxide, or the prodrug, or a solvate or hydrate of the compound, the nitrogen oxide, the prodrug, or the salt.

Non-limiting examples of more preferred compounds include: 6'-benzyloxy-3,4,5,6-tetrahydro-2H-[1,2'] bipyrazinyl; 6'-(3-chloro-benzyloxy)-3,4,5,6-tetrahydro-2H-[1,2']bipyrazinyl; 6'-(3-chloro-benzyloxy)-(2R)-methyl-3,4,5,6-tetrahydro-2H-[1,2']bipyrazinyl; 6'-(2-chloro-benzyloxy)-(2R)-methyl-3,4,5,6-tetrahydro-2H-[1,2'] bipyrazinyl; 6'-(3-fluoro-benzyloxy)-(2R)-methyl-3,4,5,6-tetrahydro-2H-[1,2']bipyrazinyl; 6'-(2-fluoro-benzyloxy)-3,4,5,6-tetrahydro-2H-[1,2']bipyrazinyl; 6'-(3-fluoro-benzyloxy)-3,4,5,6-tetrahydro-2H-[1,2']bipyrazinyl; 6'-(3-chloro-benzyloxy)-2-ethyl-3,4,5,6-tetrahydro-2H-[1,2'] bipyrazinyl; 6'-(2,5-difluoro-benzyloxy)-3,4,5,6-tetrahydro-2H-[1,2']bipyrazinyl; 6'-(2,5-dichloro-benzyloxy)-3,4,5,6-tetrahydro-2H-[1,2']bipyrazinyl; 6'-(3,5-difluoro-benzyloxy)-3,4,5,6-tetrahydro-2H-[1,2']bipyrazinyl; (3-fluoro-benzyl)-(3,4,5,6-tetrahydro-2H-[1,2']bipyrazinyl-6'-yl)-amine; (3-chloro-benzyl)-(3,4,5,6-tetrahydro-2H-[1,2']bipyrazinyl-6'-yl)-amine; (3,5-difluoro-benzyl)-(3,4,5,6-tetrahydro-2H-[1,2']bipyrazinyl-6'-yl)-amine; (3,5-dichloro-benzyl)-(3,4,5,6-tetrahydro-2H-[1,2']bipyrazinyl-6'-yl)-amine; (2-chloro-6-fluoro-benzyl)-(3,4,5,6-tetrahydro-2H-[1,2']bipyrazinyl-6'-yl)-amine; 6'-(3-chloro-benzyloxy)-3,4,5,6-tetrahydro-2H-[1,2']bipyrazinyl 4'-oxide; N-(3-chloro-benzyl)-N-(3,4,5,6-tetrahydro-2H-[1,2']bipyrazinyl-6'-yl)-acetamide; 6'-(3-chloro-benzylsulfanyl)-3,4,5,6-tetrahydro-2H-[1,2']bipyrazinyl; and 6'-(indan-(1S)-yloxy)-3,4,5,6-tetrahydro-2H-[1,2']bipyrazinyl;

a nitrogen oxide thereof, a prodrug of the compound or the nitrogen oxide; a pharmaceutically acceptable salt of the compound, the nitrogen oxide, or the prodrug, or a solvate or hydrate of the compound, the nitrogen oxide, the prodrug, or the salt.

Even more preferred compounds of Formula (IB) include: 6'-benzyloxy-3,4,5,6-tetrahydro-2H-[1,2']bipyrazinyl; 6'-(3-chloro-benzyloxy)-3,4,5,6-tetrahydro-2H-[1,2']bipyrazinyl; 6'-(3-fluoro-benzyloxy)-3,4,5,6-tetrahydro-2H-[1,2'] bipyrazinyl; 6'-(3-chloro-benzyloxy)-3,4,5,6-tetrahydro-2H-[1,2']bipyrazinyl 4'-oxide; (3-fluoro-benzyl)-(3,4,5,6-tetrahydro-2H-[1,2']bipyrazinyl-6'-yl)-amine; 6'-(3-chloro-benzyloxy)-(2R)-methyl-3,4,5,6-tetrahydro-2H-[1,2'] bipyrazinyl; 6'-(3,5-difluoro-benzyloxy)-3,4,5,6-tetrahydro-2H-[1,2']bipyrazinyl; 6'-(2,5-difluoro-benzyloxy)-3,4,5,6-tetrahydro-2H-[1,2']bipyrazinyl; and 6'-(indan-(1S)-yloxy)-3,4,5,6-tetrahydro-2H-[1,2']bipyrazinyl;

a nitrogen oxide thereof, a prodrug of the compound or the nitrogen oxide; a pharmaceutically acceptable salt of the compound, the nitrogen oxide, or the prodrug, or a solvate or hydrate of the compound, the nitrogen oxide, the prodrug, or the salt.

Compounds of the present invention may be administered in combination with other pharmaceutical agents, such as apo-B/MTP inhibitors, MCR-4 agonists, CCK-A agonists, monoamine reuptake inhibitors, sympathomimetic agents, β$_3$ adrenergic receptor agonists, dopamine agonists, melanocyte-stimulating hormone receptor analogs, cannabinoid 1 receptor antagonists, melanin concentrating hormone antagonists, leptins, leptin analogs, leptin receptor agonists, galanin antagonists, lipase inhibitors, bombesin agonists, neuropeptide-Y antagonists, thyromimetic agents, dehydroepiandrosterone or analogs thereof, glucocorticoid receptor agonists or antagonists, orexin receptor antagonists, urocortin binding protein antagonists, glucagon-like peptide-1 receptor agonists, ciliary neurotrophic factors, AGRPs (human agouti-related proteins), ghrelin receptor antagonists, histamine 3 receptor antagonists or reverse agonists, neuromedin U receptor agonists, and the like.

The combination therapy may be administered as (a) a single pharmaceutical composition which comprises a compound of the present invention, at least one additional pharmaceutical agent described above and a pharmaceutically acceptable excipient, diluent, or carrier; or (b) two separate pharmaceutical compositions comprising (i) a first composition comprising a compound of Formula (IA), (IC), or (IB) and a pharmaceutically acceptable excipient, diluent, or carrier, and (ii) a second composition comprising at least one additional pharmaceutical agent described above and a pharmaceutically acceptable excipient, diluent, or carrier. The pharmaceutical compositions may be administered simultaneously or sequentially and in any order.

In yet another aspect of the present invention, a pharmaceutical kit is provided for use by a consumer to treat 5-HT$_2$ receptor-mediated diseases, conditions, or disorders in an animal (preferably, 5-HT$_{2c}$ receptor-mediated diseases, conditions or disorders). The kit comprises a) a suitable dosage form comprising a compound of the present invention; and b) instructions describing a method of using the dosage form to treat or prevent a 5-HT$_2$ receptor-mediated disease, condition, or disorder.

In yet another embodiment of the present invention is a pharmaceutical kit comprising: a) a first dosage form comprising (i) a compound of the present invention and (ii) a pharmaceutically acceptable carrier, excipient or diluent; b) a second dosage form comprising (i) an additional pharmaceutical agent described above, and (ii) a pharmaceutically acceptable carrier, excipient or diluent; and c) a container.

Another aspect of the present invention is a method for treating female sexual dysfunction (FSD) comprising the step of administering to a female in need thereof a therapeutically effective amount of a compound of the present invention. The method may further include the administration of one or more additional active agents for treating FSD. The additional active agents may be selected from the group consisting of (1) as estrogen receptor modulators, estrogen agonists, estrogen antagonists or combinations thereof; (2) testosterone replacement agent, testosternone (Tostrelle), dihydrotestosterone, dehydroepiandrosterone (DHEA), a testosterone implant, or combinations thereof; (3) estrogen, a combination of estrogen and medroxyprogesterone or medroxyprogesterone acetate (MPA), or estrogen and methyl testosterone hormone replacement therapy agent; (4) one or more dopaminergic agents; (5) one or more of an NPY (neuropeptide Y) inhibitor; (6) one or more of a melanocortin receptor agonist or modulator or melanocortin enhancer; (7) one or more of an NEP inhibitor; (8) one or more of a PDE inhibitor; and (9) one or more of a bombesin receptor antagonist or modulator. The FSD treatments include female sexual arousal disorder (FSAD), female orgasmic disorder (FOD), hypoactive sexual desire disorder (HSDD), or sexual pain disorder.

In another embodiment of the present invention, a method is provided for treating male erectile dysfunction (MED) comprising the step of administering to a male in need thereof a therapeutically effective amount of a compound of the present invention.

Another aspect of the present invention is a method of increasing lean meat content in an edible animal comprising the step of administering to the edible animal a lean meat increasing amount of a compound of the present invention or a composition comprising the compound of the present invention. The compounds of the present invention may also be administered to the edible animal in combination with any one of the additional pharmaceutical agents described above.

Definitions

As used herein, the term "alkyl" refers to a hydrocarbon radical of the general formula $C_nH_{2n+1}$. The alkane radical may be straight or branched. For example, the term "(C$_1$–C$_4$)alkyl" refers to a monovalent, straight, or branched aliphatic group containing 1 to 4 carbon atoms (e.g., methyl, ethyl, n-propyl, i-propyl, n-butyl, i-butyl, s-butyl, t-butyl, and other constitutional isomers containing 1 to 4 carbon atoms (including stereoisomers). The alkane radical may be unsubstituted or substituted with one or more substituents. For example, a "halo-substituted alkyl" refers to an alkyl group substituted with one or more halogen atoms (e.g., fluoromethyl, difluoromethyl, trifluoromethyl, perfluoroethyl, chloromethyl, bromomethyl, and the like). Similarly, the alkyl portion of an alkoxy, alkylamino, dialkylamino, or alkylthio group has the same meaning as alkyl defined above and the halo-substituted alkyl portion of a halo-substituted alkoxy, alkyl amino, dialkylamino or alkylthio group has the same meaning as halo-substituted alkyl defined above.

The term "partially or fully saturated cycloalkyl" refers to nonaromatic rings that are either partially or fully hydrogenated. For example, partially or fully saturated (C$_3$–C$_6$) cycloalkyl includes groups such as cyclopropyl, cyclopropenyl, cyclobutyl, cyclobutenyl, cyclopentyl, cyclpentenyl, cyclopentadienyl, cyclohexyl, cyclohexenyl, cyclohexadienyl, and the like. The term "fused ring" refers to partially saturated as well as aromatic carbocyclic and heterocyclic ring systems. Preferably, the heterocyclic ring contains 1 or 2 heteroatoms independently selected from nitrogen, oxygen, and sulfur (optionally oxidized to the corresponding sulfone or sulfoxide). Non-limiting examples of fused ring systems include naphthalene, indane, indene, isoindene, benzofuran, isobenzofuran, benzo[b]thiophene, benzo[c]thiophene, indole, 3H-indole, 1H-isoindole, indazole, indoxazine, benzoxazole, anthranil, tetralin, 2H-1-benzopyran, quinoline, isoquinoline, cinnoline, quinazoline, 2H-1,3-benzoxazine, 2H-1,4-benzoxazine, 1H-2,3-benzoxazine, 4H-2,1-benzoxazine, 2H-1,2-benzoxazine, 4H-1,4-benzoxazine, and the like.

The term "heteroaryl" refers to aromatic monocyclic or bicyclic ring systems containing 1, 2 or 3 heteroatoms independently selected from nitrogen, oxygen, and sulfur. The heteroaryl group may be unsubstituted or substituted with 1 to 3 substituents. Preferred substituents include halo (Br, Cl, I, or F), (C$_1$–C$_4$) alkyl, cyano, nitro, amino, (C$_1$–C$_4$) alkylamino, and (C$_1$–C$_4$) alkoxy. Suitable heteroaryl groups include is a heteroaryl group selected from the group consisting of pyridin-2-yl, pyridin-3-yl, furan-3-yl, furan-2-yl, thiophen-2-yl, thiophen-3-yl, thiazol-2-yl, pyrrol-2-yl, pyrrol-3-yl, pyrazol-3-yl, quinolin-2-yl, quinolin-3-yl, isoquinolin-3-yl, benzofuran-2-yl, benzofuran-3-yl, isobenzofuran-3-yl, benzothiophen-2-yl, benzothiophen-3-yl, indol-2-yl, indol-3-yl, 2H-imidazol-2-yl, oxazol-2-yl, isoxazol-3-yl, 1,2,4-oxadiazol-3-yl, 1,2,4-oxadiazol-5-yl, 1,3,4-oxadiazol-2-yl, 1,3,4-oxadiazol-5-yl, 1,2,4-triazol-3-yl, 1,2,3-thiadiazol-4-yl, 1,2,3-thiadiazol-5-yl, 1,3,4-thiadiazol-2-yl, 1,3,4-thiadiazol-5-yl, 1,2,4-oxathiazol-3-yl, and the like.

The term "substituted" means that a hydrogen atom on a molecule has been replaced with a different atom or molecule. The atom or molecule replacing the hydrogen atom is denoted as a "substituent." The term substituted specifically envisions and allows for substitutions that are common in the art. However, it is generally understood by those skilled in the art that the substituents should be selected so as to not adversely affect the pharmacological characteristics of the compound or adversely interfere with the use of the medicament.

The term "nitrogen oxide" or "N-oxide" refers to the oxidation of at least one of the nitrogens in the pyrimidine or pyrazine ring of the compounds of Formula (IA), (IB) or (IC)(e.g., mono- or di-oxide). The nitrogen mono-oxides may exist as a single positional isomer or a mixture of positional isomers (e.g., a mixture of 1-N-oxide and 3-N-oxide pyrimidines or a mixture of 1-N-oxide and 4-N-oxide pyrazines).

The term "protecting group" or "Pg" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBz) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include —CH$_2$CH$_2$SO$_2$Ph, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)ethyl, nitroethyl and the like. For a general description of protecting groups and their use, see T. W. Greene, *Protective Groups in Organic Synthesis*, John Wiley & Sons, New York, 1991.

The term "ligand" refers to a compound that binds to a receptor. As used herein, the ligand may possess partial or full agonist or antagonist activity.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "animal" refers to humans, companion animals (e.g., dogs, cats and horses), food-source animals, zoo animals, marine animals, birds and other similar animal species. "Edible animals" refers to food-source animals such as cows, pigs, sheep and poultry.

The phrase "pharmaceutically acceptable" indicates that the substance or composition must be compatible chemically and/or toxicologically, with the other ingredients comprising a formulation, and/or the mammal being treated therewith.

The terms "treating", "treat", or "treatment" embrace both preventative, i.e., prophylactic, and palliative treatment.

The term "compounds of the present invention" (unless specifically identified otherwise) refer to compounds of Formulae (IA), (IC) and (IB), nitrogen oxides thereof, prodrugs of the compounds or nitrogen oxides, pharmaceutically acceptable salts of the compounds, nitrogen oxides, and/or prodrugs, and hydrates or solvates of the compounds, nitrogen oxides, salts, and/or prodrugs, as well as, all stereoisomers (including diastereoisomers and enantiomers), tautomers and isotopically labeled compounds.

DETAILED DESCRIPTION

The present invention provides a method for treating or preventing 5-HT$_2$ receptor-mediated diseases, conditions, or disorders by administering compounds of Formula (IB) which act as 5-HT$_2$ receptor ligands (preferably, 5-HT$_{2c}$ and/or 5-HT$_{2a}$ receptor ligands).

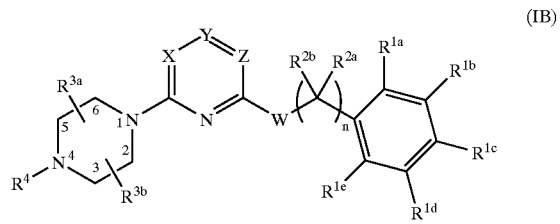

(IB)

wherein
Y is N;
X and Z are each independently CR, where R for each occurrence is hydrogen, halogen, (C$_1$–C$_4$)alkyl, amino, or (C$_1$–C$_4$)alkylamino;
W is oxy, thio, amino, (C$_1$–C$_4$)alkylamino, or acetylamino;
R$^{1a}$, R$^{1b}$, R$^{1c}$, R$^{1d}$ and R$^{1e}$ are each independently hydrogen, halogen, nitro, cyano, amino, (C$_1$–C$_4$)alkylamino, (C$_1$–C$_4$)alkyl, halo-substituted (C$_1$–C$_4$)alkyl, (C$_1$–C$_4$)alkoxy, halo-substituted (C$_1$–C$_4$)alkoxy, —C(O)NH$_2$, R$^{1a}$ and R$^{1b}$ taken together form a five- or six-membered, aromatic or partially or fully saturated fused ring, or R$^{1a}$ taken together with R$^{2a}$ or R$^{2b}$ forms a five- or six-membered, fully saturated, fused ring;
R$^{2a}$ and R$^{2b}$ are each independently hydrogen, (C$_1$–C$_4$) alkyl, partially or fully saturated (C$_3$–C$_6$)cycloalkyl, or one of which taken together with R$^{1a}$ forms a five- or six-membered, fully saturated fused ring;
n is 0, 1, or 2;
R$^{3a}$ and R$^{3b}$ are each independently hydrogen, halogen, (C$_1$–C$_4$)alkyl, or (C$_1$–C$_4$)alkyl substituted with hydroxy, fluoro, or (C$_1$–C$_4$)alkoxy;
R$^4$ is hydrogen, hydroxy, (C$_1$–C$_4$)alkyl, (C$_1$–C$_4$)alkyl substituted with hydroxy or cyano, (C$_1$–C$_4$)alkylcarbonyl, (C$_1$–C$_4$)alkoxy, (C$_1$–C$_4$)alkoxy-carbonyl, or (C$_3$–C$_4$) alkenyl;
a nitrogen oxide thereof, a prodrug of the compound or the nitrogen oxide; a pharmaceutically acceptable salt of the compound, the nitrogen oxide, or the prodrug, or a solvate or hydrate of the compound, the nitrogen oxide, the prodrug, or the salt.

Compounds of the present invention may be synthesized by synthetic routes that include processes analogous to those known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1–19, Wiley, New York (1967–1999 ed.), or *Beilsteins Handbuch der organischen Chemie*, 4, Aufl. ed. Springer-Verlag, Berlin, including supplements (also available via the Beilstein online database)).

For illustrative purposes, the reaction schemes depicted below provide potential routes for synthesizing the compounds of the present invention as well as key intermediates. For a more detailed description of the individual reaction steps, see the Examples section. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art. For example, a sulfide linkage (i.e., W=S) can be easily oxidized to its corresponding sulfinyl or sulfonyl group (i.e., W=SO or $SO_2$) using common oxidation procedures (e.g., oxidation with m-chloroperbenzoic acid).

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, *Protective Groups in Organic Synthesis*, John Wiley & Sons, New York, 1991.

Scheme I illustrates the preparation of compounds of the present invention where W is O, S, amino or $(C_1-C_4)$ alkylamino.

Scheme I

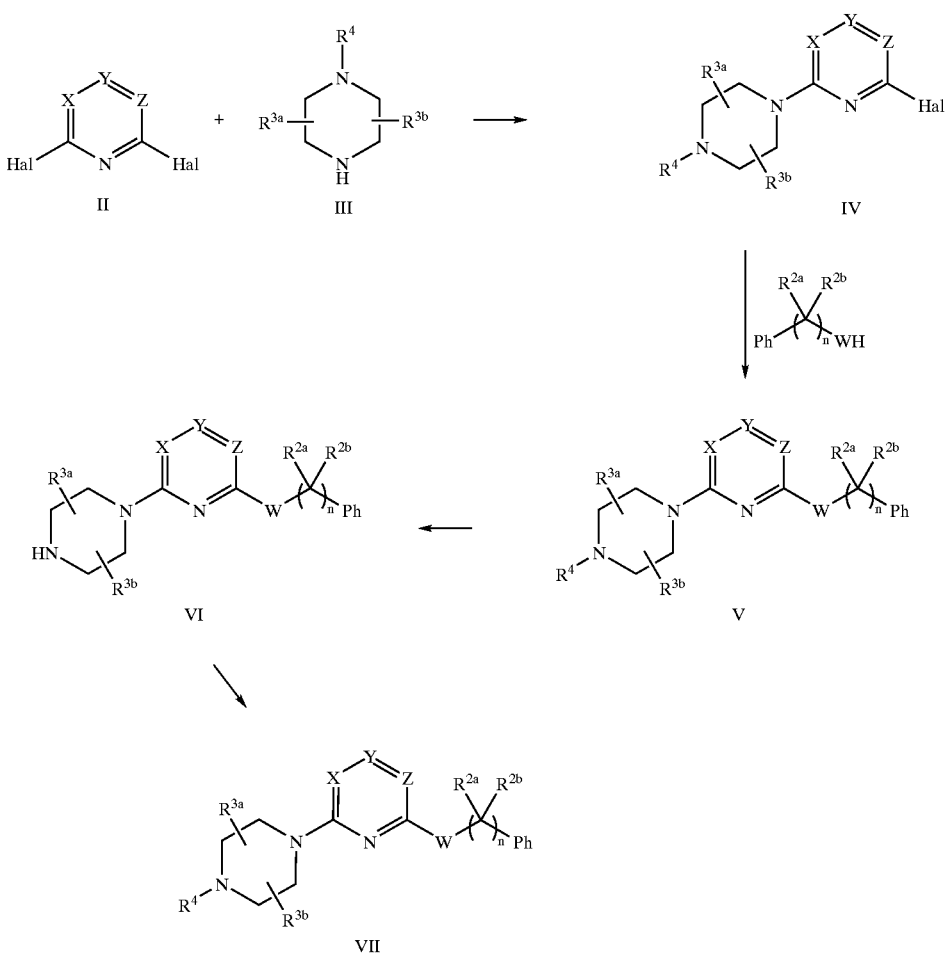

W = —O, —S, —NH, or $(C_1-C_4)$ alkylamine
Ph = substituted or unsubstituted phenyl Reaction of the di-halogen substituted heteroaryl compound of Formula II with a compound of Formula III ($R^4$ may optionally be an amino-protecting group) in a suitable solvent (e.g., ethanol, t-butanol, n-butanol, toluene, dioxane, THF, DMF, or acetonitrile) in the presence of a suitable base (e.g., sodium carbonate, potassium carbonate, cesium carbonate, sodium hydroxide (NaOH), potassium hydroxide, 1,8-diazabicyclo-[5.4.0]undec-7-ene (DBU), triethylamine (TEA) or pyridine) at about 25° C. to about 200° C. for about 1 to about 168 hours gives intermediate IV. Treatment of intermediate IV with an excess of the appropriate amine in a solvent (e.g., EtOH, t-BuOH, dioxane, THF or DMF) in the presence of a suitable base (e.g., sodium carbonate, potassium carbonate, cesium carbonate, NaOH, sodium hydride, DBU, TEA or pyridine) at about 25° C. to about 200° C. for about 1 to about 7 days produces intermediate V wherein W is an amino linking group or a ($C_1$–$C_4$)alkyl substituted amino linking group. Suitable amines include benzylamine, 3-chlorobenzyl amine, 3-fluorobenzyl amine, and the like.

Alternatively, intermediate IV may be reacted with an anion of an appropriate alcohol or thiol in a solvent (e.g., THF, toluene, dioxane, DMF, benzene, or a mixture of benzene and water) with or without a catalyst such as 18-crown-6 at about 25° C. to about 200° C. for about 1 to about 48 hours to yield compounds of formula V wherein W is O or S. The anion may be obtained by treatment of the corresponding alcohol or thiol with a base (e.g., potassium carbonate, sodium hydride, sodium hydroxide, potassium hydroxide, potassium t-butoxide, or sodium metal) in an inert solvent (e.g., toluene, dioxane, DMF, THF, or benzene) at about 25° C. to about 200° C. for about 1 to about 24 hours.

Suitable alcohols include benzyl alcohol, α-phenethyl alcohol, β-phenethyl alcohol, 3-fluoro-benzyl alcohol, 3-chloro-benzyl alcohol, 3-methoxybenzyl alcohol, 2-chlorobenzyl alcohol, 3-fluoro-α-phenethyl alcohol, 2-chloro-α-phenethyl alcohol, 3-chloro-α-phenethyl alcohol, 2,5-difluorobenzyl alcohol, 2,5-dichlorobenzyl alcohol, 3,5-difluorobenzyl alcohol, 3,5-dichlorobenzyl alcohol, 2-hydroxymethylpyridine, 2-hydroxymethyl-6-chloro-pyridine, 2-hydroxymethyl-6-methyl-pyridine, and the like.

Suitable thiols include α-toluenethiol, (2-methylphenyl)methanethiol, 3-(trifluoromethyl)-α-toluenethiol, 2-chloro-α-toluenethiol, (3-methylphenyl)-methanethiol, 2-chloro-6-fluorobenzylmercaptan, o-fluorobenzyl mercaptan, m-chlorobenzyl mercaptan, 2,4,6-trimethylbenzyl mercaptan, and the like.

The sulfide linkage can be oxidized to the corresponding sulfinyl or sulfonyl using standard oxidation procedures well known to those skilled in the art.

When $R^4$ is an amino-protecting group, intermediate V is deprotected to give the amine VI. For example, a BOC protected amine may be deprotected by treatment with trifluoroacetic acid (TFA) in $CH_2Cl_2$. The secondary amine VI may be acylated or converted to a carbamate according to methods well known to those skilled in the art. Alternatively, the secondary amine VI can be alkylated to the amine VII by methods well known to those skilled in the art. A preferred method is reductive alkylation. Generally, reductive alkylation reactions convert intermediate VI into a Schiff base by reaction with the desired aldehyde or ketone in a polar solvent at a temperature from about 10° C. to about 140° C. for about 2 to about 24 hours in the presence of 3 Å molecular sieves. Typically, an equivalent or a slight excess of the aldehyde or ketone is added to the amine. Suitable polar solvents include methylene chloride, 1,2-dichloroethane, dimethylsulfoxide, dimethylformamide, alcohols (e.g., methanol or ethanol), or mixtures thereof. A preferred solvent is methanol. In the same reaction vessel, the imine is then reduced to the tertiary amine in the presence of a reducing agent at a temperature from about 0° C. to about 10° C. and then warmed to a temperature from about 20° C. to about 40° C. for about 30 minutes to about 2 hours. Suitable reducing agents include pyridine●borane complex and metal borohydrides, such as sodium borohydride, sodium triacetoxy borohydride and sodium cyanoborohydride. Suitable aldehydes or ketones include paraformaldehyde, acetaldehyde, acetone and the like.

In an alternate synthetic approach, intermediate V where W is an amino or a ($C_1$–$C_4$)alkyl substituted amino linking group may be prepared from IV with an amine or a ($C_1$–$C_4$) alkyl substituted amino via metal-catalyzed coupling reaction as described in Metal-Catalyzed Cross-Coupling Reaction (Editors: F. Diederich, P. J. Stang; VCH, Weinheim, 1998). For example, treatment of the intermediate IV with an appropriate amine in a suitable solvent (e.g, xylene, toluene, THF, and dioxane) in the presence of a suitable base (e.g, sodium t-butoxide, sodium bicarbonate, and potassium biocarbonate) and a suitable phosphine ligand such as racemic 2,2'-bis(diphenylphosphino)-1,1'-binaphthyl (BINAP), triphenylphosphine, tri-t-butylphosphine or 2-dicyclohexylphosphino-2'-(N,N-dimethylamino)-biphenyl (AmPhos) and a suitable palladium catalyst such as trisdibenzylidene-acetone dipalladium ($Pd_2(dba)_3$) or palladium chloride at about 25° C. to about 200° C. for about 1 to about 24 hours gives compound of formula V wherein W is an amine linking group. The ratio of palladium to phosphine ligand is typically between about 1:1 and about 1:5. Typically, about 0.01 to about 0.3 equivalent of catalyst is used relative to starting IV.

Compounds wherein X and Z are CR, where one or both of the R groups is not hydrogen, may be obtained via the appropriate dihalide II. For example, compounds where one R=$NH_2$ and the other R=H may be obtained by employing 2-amino-3,5-dibromopyrazine as starting material. Alternatively, these types of compounds may be obtained by functionalization of a compound of the formula V, where X=Y=CH. These functionalization reactions are well-known to those skilled in the art, and include electrophilic aromatic substitution reactions, such as halogenations (e.g., chlorinations, brominations, and fluorinations). These reactions can produce both of the two possible monohalogenated compounds, as well as the dihalogenated compounds, which are easily separated by common purification methods, such as chromatography. For example, a compound of formula V, where X=Y=CH and $R^4$ is a nitrogen protecting group in an inert solvent (e.g., acetonitrile, chloroform, dichloromethane or THF) is reacted with a suitable electrophilic halogenating agent, such as N-chlorosuccinamide, N-bromosuccinamide, bromine, chlorine or Selectfluor™ at a temperature of about −78° C. to about 100° C. for about 1 hour to about 24 h gives mixtures of the two possible monohalogenated compounds and the dihalogenated compound. The relative amounts of each of these can vary depending on the particular case.

The brominated pyrazine compounds described above can be transformed to a variety of other derivatives by methods known to those skilled in the art. Conveniently, they can be transformed to alkyl derivatives via a palladium-catalyzed reaction, such as the Suzuki reaction employing alkyl boronic acids or a derivative thereof. For example, reaction of a brominated pyrazine with an alkylboronic acid in the presence of a suitable palladium catalyst, a suitable ligand, such as AmPhos or BINAP, a base, such as sodium tert-butoxide, $K_3PO_4$, or $CsCO_3$, in a suitable solvent, such as toluene, THF and dioxane, at a temperature of about 25° C. to about 110° C. for about 3 h to about 24 h.

Alternatively, Compound VII can be prepared according to Scheme II below.

above. Intermediate VIII is converted to intermediate V by reaction with piperazine III using aromatic nucleophilic substitution conditions or palladium-catalyzed coupling reaction conditions as described in Scheme 1. Compound V can then be converted to compound VI and compound VII according to the procedures described above in Scheme 1.

Compounds of the present invention where W is an amino linking group (NH) or alkylamino linking group can also be

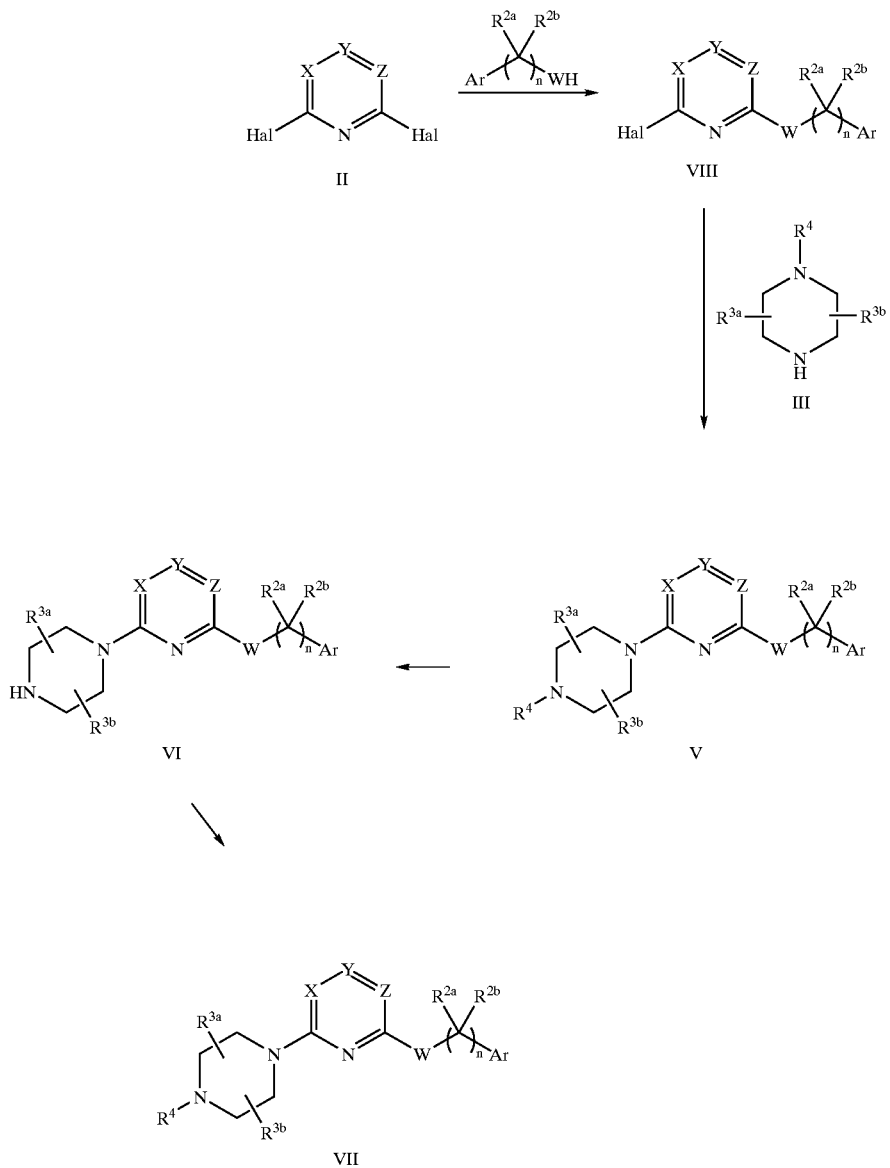

W = ―O, ―S, ―NH, or $(C_1–C_4)$ alkylamine
Ph = substituted or unsubstituted phenyl or heteroaryl Intermediate VIII is prepared by reacting the di-halogen substituted heteroaryl compound II with one equivalent of an appropriate alcohol, thiol or amine using aromatic nucleophilic substitution conditions described in Scheme 1 prepared by reductive alkylation of an amino group attached to the pyrazine ring as illustrated in Scheme III below. The synthetic procedures are analogous to those described above for the reductive alkylation of intermediate VI in Scheme I.

Scheme III

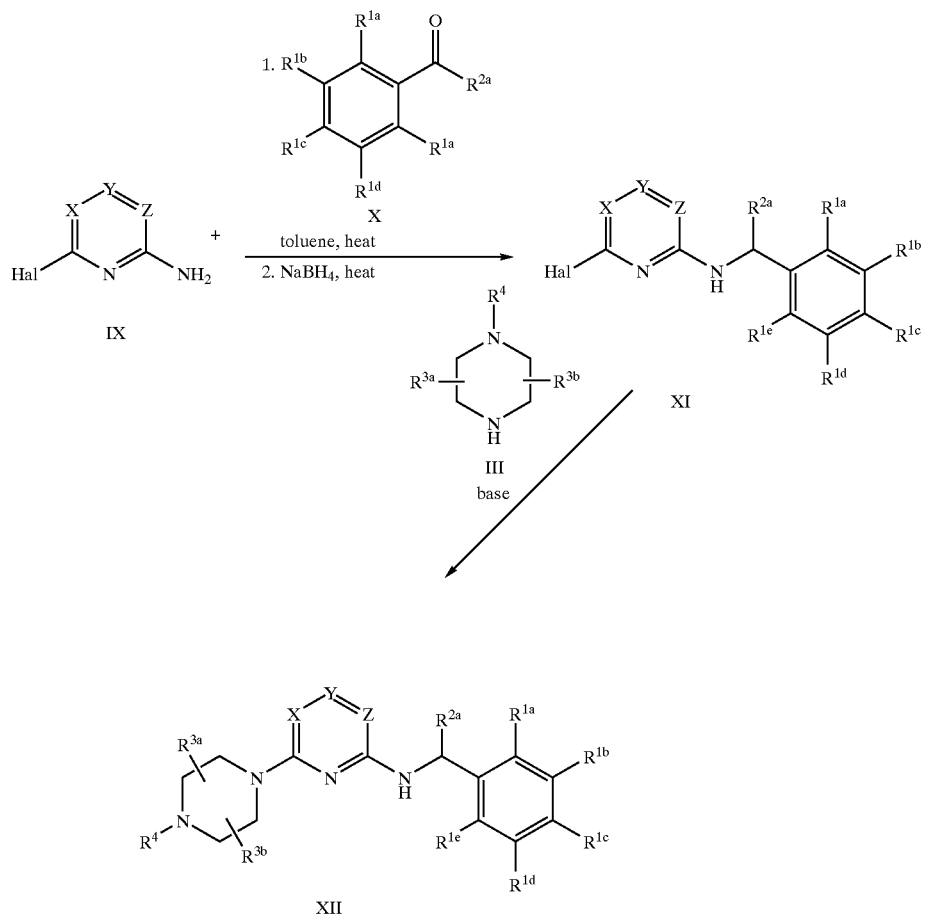

The compound of Formula IX can be converted to the benzyl amine XI by methods well known in the art. A preferred method is reductive alkylation as described earlier in Scheme I where a Schiff base is formed with intermediate X and then reduced with an appropriate reducing agent. Suitable aldehydes and ketones (i.e., compound of Formula X) include 3-chlorobenzaldehyde, 3-fluorobenzaldehyde, m-chloroacetophenone, m-chloropropiophenone, o-chloroacetophenone, 2-fluorobenzaldehyde, 2-chlorobenzaldehyde, 2,6-dichlorobenzaldehyde, 2,5-dichloroacetophenone, 2-chloro-5-methylacetophenone, 2,5-difluoroacetophenone, 2,5-difluoropropiophenone, 2,3-dichlorobenzaldehyde, 2,3-difluorobenzaldehyde, 2,5-difluorobenzaldehyde, 2-chloro-5-fluoroacetophenone, 5-chloro-2-methoxybenzaldehyde, 2-fluoro-5-methoxybenzaldehyde, 2,5-dichlorobenzaldehyde, 3,5-dichlorobenzaldehyde, 3,5-dichloroacetophenone, 3,5-difluorobenzaldehyde, 2,3,5-trifluorobenzaldehyde, 2,3,5-trifluoroacetophenone, 2,3,5-trifluoropropiophenone, 2,3,5-trichlorobenzaldehyde, 2,3,6-trifluorobenzaldehyde, and the like. Treatment of the resultant compound of Formula XI with piperazine III in a suitable solvent (e.g., ethanol, t-butanol, n-butanol, toluene, dioxane, THF, DMF or acetonitrile) in the presence of a suitable base (e.g., sodium carbonate, potassium carbonate, sodium hydroxide, TEA, DBU, or pyridine) at about 25° to about 200° C. for about 1 day to about seven days gives compounds of the Formula XII.

Compound XII may be oxidized to an N-oxide by reacting XII with a suitable oxidizing agent, such as a peracid, for example, m-chloroperbenzoic acid (mCPBA) in a suitable solvent, such as chloroform or dichloromethane at a temperature of about −78° C. to about 65° C., for about 2 h to about 24 h. Other useful methods of carrying out this oxidation are well-known to those skilled in the art.

Scheme IV below illustrates an alternative synthetic route for the synthesis of Compound XVII (same as compound VI wherein W is an amine linking group).

Scheme IV

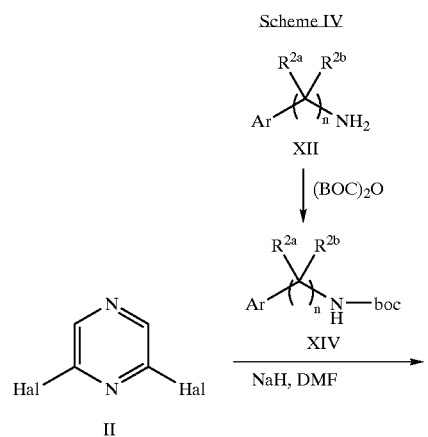

-continued

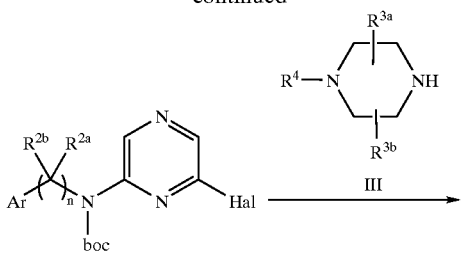

XV

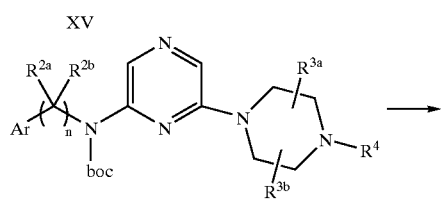

XVI

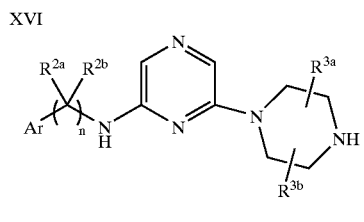

XVII

Compound II is reacted with an appropriate BOC protected amine in the presence of a base, such as sodium hydride in DMF to afford intermediate XV. The BOC protected amine may be obtained by treatment of the corresponding amine with di-tert-butyl dicarbonate in $CH_2Cl_2$ or THF. Treatment of XV with III using aromatic nucleophilic substitution conditions or palladium-catalyzed coupling conditions as described in Scheme 1 provides XVI. Deprotection of compound XVI with hydrochloride or trifluoroacetic acid in $CH_2Cl_2$ or THF (as described above) provides the desired product XVII.

Scheme V below illustrates how to synthesize compounds of the present invention where W is an acetylamine.

Scheme V

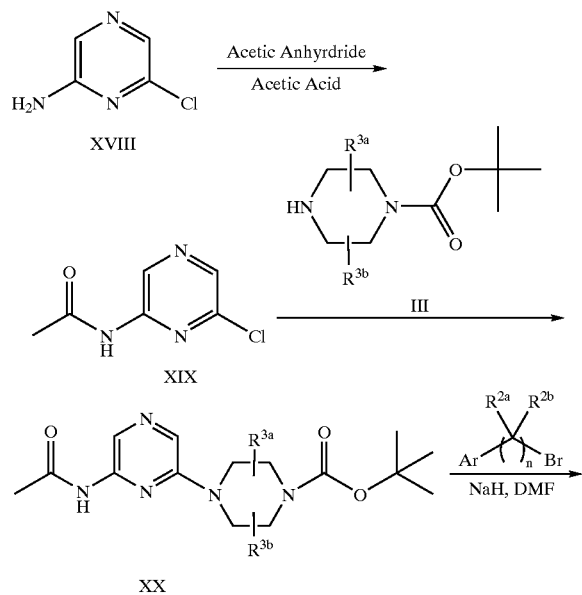

-continued

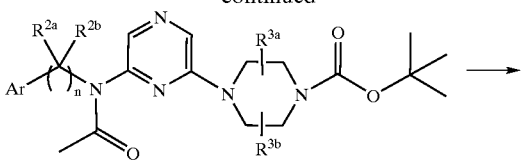

XXI

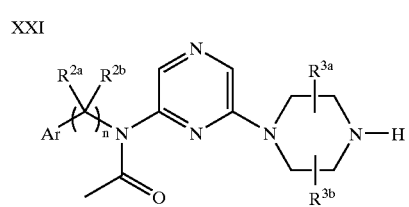

XXII

Acylation of XVIII with acetic anhydride in acetic acid gives acylated product XIX. Reaction of XIX with III wherein $R^4$ is BOC using aromatic nucleophilic substitution conditions or palladium-catalyzed coupling conditions as described in Scheme 1 above affords XX. Alkylation of XX with an appropriate alkylhalide in the presence of sodium hydride in DMF provides XXI. Deprotection of XXI with HCl or TFA in $CH_2Cl_2$ or THF as described above yields XXII.

Conventional methods and/or techniques of separation and purification known to one of ordinary skill in the art can be used to isolate the compounds of the present invention, as well as the various intermediates related thereto. Such techniques will be well-known to one of ordinary skill in the art and may include, for example, all types of chromatography (high pressure liquid chromatography (HPLC), column chromatography using common adsorbents such as silica gel, and thin-layer chromatography), recrystallization, and differential (i.e., liquid-liquid) extraction techniques.

The compounds of the present invention may be isolated and used per se or in the form of its pharmaceutically acceptable salt, solvate and/or hydrate. The term "salts" refers to inorganic and organic salts of a compound of the present invention. These salts can be prepared in situ during the final isolation and purification of a compound, or by separately reacting the compound, N-oxide, or prodrug with a suitable organic or inorganic acid and isolating the salt thus formed. Representative salts include the hydrobromide, hydrochloride, hydroiodide, sulfate, bisulfate, nitrate, acetate, trifluoroacetate, oxalate, besylate, palmitiate, pamoate, malonate, stearate, laurate, malate, borate, benzoate, lactate, phosphate, hexafluorophosphate, benzene sulfonate, tosylate, formate, citrate, maleate, fumarate, succinate, tartrate, naphthylate, mesylate, glucoheptonate, lactobionate, and laurylsulphonate salts, and the like. Preferred salts include hydrochloride, fumarate, citrate, L-malate, and D,L-tartrate, more preferred salts include citrate, L-malate, and D,L-tartrate. These may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, e.g., Berge, et al., *J. Pharm. Sci.*, 66, 1–19 (1977).

The term "nitrogen oxide" or "N-oxide" refers to the oxidation of at least one of the nitrogen atoms in the pyrazine ring. Oxidation of aromatic nitrogens is well known in the art. Typical oxidizing agents include reagents such as hydrogen peroxide, trifluoroperacetic acid, m-chloroperbenzoic acid and the like. In general, the oxidation is accomplished in an inert solvent (e.g., methylene chloride or chloroform). The position of the N-oxidation may vary depending upon the steric hinderance from substituents on an adjacent carbon atom. The N-oxide or mixture of N-oxides can be isolated or separated using conventional procedures such as liquid chromatography and/or selective crystallization.

The term "prodrug" means a compound that is transformed in vivo to yield a compound of Formula (IA, IB or IC) or a pharmaceutically acceptable salt, hydrate or solvate of the compound. The transformation may occur by various mechanisms, such as through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of the present invention contains a carboxylic acid functional group, a prodrug can comprise an ester formed by the replacement of the hydrogen atom of the acid group with a group such as $(C_1-C_8)$ alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$alkyl.

Similarly, if a compound of the present invention contains an alcohol functional group, a prodrug can be formed by the replacement of the hydrogen atom of the alcohol group with a group such as $(C_1-C_6)$alkanoyloxymethyl, 1-(($C_1-C_6$) alkanoyloxy)ethyl, 1-methyl-1-(($C_1-C_6$)alkanoyloxy)ethyl, $(C_1-C_6)$alkoxycarbonyloxymethyl, N—$(C_1-C_6)$ alkoxycarbonylaminomethyl, succinoyl, $(C_1-C_6)$alkanoyl, α-amino$(C_1-C_4)$alkanoyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)$alkyl$)_2$ or glycosyl (the radical resulting from the removal of a hydroxyl group of the hemiacetal form of a carbohydrate).

If a compound of the present invention incorporates an amine functional group, a prodrug can be formed by the replacement of a hydrogen atom in the amine group with a group such as R-carbonyl, RO-carbonyl, NRR'-carbonyl where R and R' are each independently $(C_1-C_{10})$alkyl, $(C_3-C_7)$cycloalkyl, benzyl, or R-carbonyl is a natural α-aminoacyl or natural α-aminoacyl-natural α-aminoacyl, —C(OH)C(O)OY' wherein Y' is H, $(C_1-C_6)$alkyl or benzyl, —C(OY$_0$)Y$_1$ wherein Y$_0$ is $(C_1-C_4)$ alkyl and Y$_1$ is $(C_1-C_6)$ alkyl, carboxy$(C_1-C_6)$alkyl, amino$(C_1-C_4)$alkyl or mono-N— or di-N,N—$(C_1-C_6)$alkylaminoalkyl, —C(Y$_2$)Y$_3$ wherein Y$_2$ is H or methyl and Y$_3$ is mono-N— or di-N, N—$(C_1-C_6)$alkylamino, morpholino, piperidin-1-yl or pyrrolidin-1-yl.

The compounds of the present invention may contain asymmetric or chiral centers, and, therefore, exist in different stereoisomeric forms. It is intended that all stereoisomeric forms of the compounds of the present invention as well as mixtures thereof, including racemic mixtures, form part of the present invention. In addition, the present invention embraces all geometric and positional isomers. For example, if a compound of the present invention incorporates a double bond or a fused ring, both the cis- and trans-forms, as well as mixtures, are embraced within the scope of the invention. Both the single positional isomers and mixture of positional isomers resulting from the N-oxidation of the pyrimidine and pyrazine rings are also within the scope of the present invention.

Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

The compounds of the present invention may exist in unsolvated as well as solvated forms with pharmaceutically acceptable solvents such as water, ethanol, and the like, and it is intended that the invention embrace both solvated and unsolvated forms.

It is also possible that the compounds of the present invention may exist in different tautomeric forms, and all such forms are embraced within the scope of the invention. For example, all of the tautomeric forms of the imidazole moiety are included in the invention. Also, for example, all ketoenol and imine-enamine forms of the compounds are included in the invention.

The present invention also embraces isotopically-labeled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labeled compounds of the present invention (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labeled compounds of the present invention can generally be prepared by following procedures analogous to those disclosed in the Schemes and/or in the Examples hereinbelow, by substituting an isotopically labeled reagent for a non-isotopically labeled reagent.

Compounds of the present invention are useful 5-HT$_2$ partial agonists or antagonists (preferably 5-HT$_{2a}$ or 5-HT$_{2c}$ partial agonists or antagonists); therefore, another embodiment of the present invention is a pharmaceutical composition comprising a therapeutically effective amount of a compound of the present invention and a pharmaceutically acceptable excipient, diluent or carrier.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients described above. The compound of the present invention is typically formulated into pharmaceutical dosage forms to provide an easily controllable dosage of the drug and to give the patient an elegant and easily handleable product.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The present invention further provides methods of treating 5-$HT_2$ receptor-mediated diseases, conditions, or disorders in an animal in need of such treatment that include administering to the animal a therapeutically effective amount of a compound of the present invention or a pharmaceutical composition comprising an effective amount of a compound of the present invention and a pharmaceutically acceptable excipient, diluent, or carrier. The method is particularly useful for treating 5-$HT_{2c}$ receptor-mediated diseases, conditions, or disorders. Preferably, the compounds of the present invention act as a partial agonist at the 5-$HT_{2c}$ receptor site. More preferably, the compounds of the present invention act as a partial agonist the 5-$HT_{2c}$ receptor site and as an antagonist at the 5-$HT_{2a}$ receptor site.

Preferably, the 5-$HT_2$ receptor-mediated disease, condition, or disorder is selected from the group consisting of weight loss (e.g., reduction in calorie intake), obesity, bulimia, premenstrual syndrome or late luteal phase syndrome, depression, a typical depression, bipolar disorders, psychoses, schizophrenia, migraine, alcoholism, tobacco abuse, panic disorder, anxiety, post-traumatic syndrome, memory loss, dementia of aging, social phobia, attention deficit hyperactivity disorder, disruptive behavior disorders, impulse control disorders, borderline personality disorder, obsessive compulsive disorder, chronic fatigue syndrome, sexual dysfunction in males (e.g., premature ejaculation and erectile difficulty), sexual dysfunction in females, anorexia nervosa, disorders of sleep (e.g., sleep apnea), autism, seizure disorders, epilepsy, mutism, spinal cord injury, damage of the central nervous system (e.g., trauma, stroke, neurodegenerative diseases or toxic or infective CNS diseases (e.g., encephalitis or meningitis)), cardiovascular disorders (e.g., thrombosis), gastrointestinal disorders (e.g., dysfunction of gastrointestinal motility), diabetes insipidus, and type II diabetes. Accordingly, the compounds of the present invention described herein are useful in treating or preventing 5-$HT_2$ receptor-mediated diseases, conditions, or disorders. Consequently, the compounds of the present invention (including the compositions and processes used therein) may be used in the manufacture of a medicament for the therapeutic applications described herein The compounds of the present invention can be administered to a patient at dosage levels in the range of from about 0.7 mg to about 7,000 mg per day. For a normal adult human having a body weight of about 70 kg, a dosage in the range of from about 0.01 mg to about 100 mg per kilogram body weight is typically sufficient. However, some variability in the general dosage range may be required depending upon the age and weight of the subject being treated, the intended route of administration, the particular compound being administered and the like. The determination of dosage ranges and optimal dosages for a particular patient is well within the ability of one of ordinary skill in the art having the benefit of the instant disclosure. It is also noted that the compounds of the present invention can be used in sustained release, controlled release, and delayed release formulations, which forms are also well known to one of ordinary skill in the art.

The compounds of this invention may also be used in conjunction with other pharmaceutical agents for the treatment of the diseases/conditions described herein. Therefore, methods of treatment that include administering compounds of the present invention in combination with other pharmaceutical agents are also provided. Suitable pharmaceutical agents that may be used in combination with the compounds of the present invention include anti-obesity agents such as apolipoprotein-B secretion/microsomal triglyceride transfer protein (apo-B/MTP) inhibitors, MCR-4 agonists, cholecystokinin-A (CCK-A) agonists, monoamine reuptake inhibitors (such as sibutramine), sympathomimetic agents, $\beta_3$ adrenergic receptor agonists, dopamine agonists (such as bromocriptine), melanocyte-stimulating hormone receptor analogs, cannabinoid 1 receptor antagonists, melanin concentrating hormone antagonists, leptins (the OB protein), leptin analogs, leptin receptor agonists, galanin antagonists, lipase inhibitors (such as tetrahydrolipstatin, i.e. orlistat), anorectic agents (such as a bombesin agonist), Neuropeptide-Y antagonists, thyromimetic agents, dehydroepiandrosterone or an analog thereof, glucocorticoid receptor agonists or antagonists, orexin receptor antagonists, urocortin binding protein antagonists, glucagon-like peptide-1 receptor agonists, ciliary neurotrophic factors (such as Axokine™ available from Regeneron Pharmaceuticals, Inc., Tarrytown, N.Y. and Procter & Gamble Company, Cincinnati, Ohio), human agouti-related proteins (AGRP), ghrelin receptor antagonists, histamine 3 receptor antagonists or reverse agonists, and neuromedin U receptor agonists. Other anti-obesity agents, including the preferred agents set forth hereinbelow, are well known, or will be readily apparent in light of the instant disclosure, to one of ordinary skill in the art.

Especially preferred are anti-obesity agents selected from the group consisting of orlistat, sibutramine, bromocriptine, ephedrine, leptin, and pseudoephedrine. Preferably, compounds of the present invention and combination therapies are administered in conjunction with exercise and a sensible diet.

Representative anti-obesity agents for use in the combinations, pharmaceutical compositions, and methods of the invention can be prepared using methods known to one of ordinary skill in the art, for example, sibutramine can be prepared as described in U.S. Pat. No. 4,929,629; bromocriptine can be prepared as described in U.S. Pat. Nos. 3,752,814 and 3,752,888; and orlistat can be prepared as described in U.S. Pat. Nos. 5,274,143; 5,420,305; 5,540,917; and 5,643,874. All of the above recited U.S. patents are incorporated herein by reference.

The dosage of the additional pharmaceutical agent (e.g., anti-obesity agent) will also be generally dependent upon a number of factors including the health of the subject being treated, the extent of treatment desired, the nature and kind of concurrent therapy, if any, and the frequency of treatment and the nature of the effect desired. In general, the dosage range of an anti-obesity agent is in the range of from about 0.001 mg to about 100 mg per kilogram body weight of the individual per day, preferably from about 0.1 mg to about 10 mg per kilogram body weight of the individual per day. However, some variability in the general dosage range may also be required depending upon the age and weight of the subject being treated, the intended route of administration, the particular anti-obesity agent being administered and the like. The determination of dosage ranges and optimal dosages for a particular patient is also well within the ability of one of ordinary skill in the art having the benefit of the instant disclosure.

In another embodiment of the present invention, the compounds of the present invention have been found to be useful in the treatment of sexual dysfunction. Sexual dysfunction (SD) is a significant clinical problem, which can affect both males and females. The causes of SD may be both organic as well as psychological. Organic aspects of SD are typically caused by underlying vascular diseases, such as those associated with hypertension or diabetes mellitus, by prescription medication and/or by psychiatric disease such as depression. Physiological factors include fear, performance anxiety and interpersonal conflict. SD impairs sexual performance, diminishes self-esteem and disrupts personal relationships thereby inducing personal distress. In the clinic, SD disorders have been divided into female sexual dysfunction (FSD) disorders and male sexual dysfunction (MSD) disorders (Melman et al 1999). FSD is best defined as the difficulty or inability of a woman to find satisfaction in sexual expression. Male sexual dysfunction (MSD) is generally associated with erectile dysfunction, also known as male erectile dysfunction (MED) (Benet et al 1994— Male Erectile dysfunction assessment and treatment options. Comp. Ther. 20: 669–673.).

The compounds of the invention are particularly beneficial for the prophylaxis and/or treatment of sexual dysfunction in the male (e.g. male erectile dysfunction—MED) and in the female—female sexual dysfunction (FSD), e.g. female sexual arousal disorder (FSAD).

It is known that some individuals can suffer from male erectile dysfunction (MED). MED is defined as: "the inability to achieve and/or maintain a penile erection for satisfactory sexual performance" (NIH Consensus Development Panel on Impotence, 1993)"

It has been estimated that the prevalence of erectile dysfunction (ED) of all degrees (minimal, moderate and complete impotence) is 52% in men 40 to 70 years old, with higher rates in those older than 70 (Melman,A. & Gingell, J. C. (1999). The epidemiology and pathophysiology of erectile dysfunction. *J. Urology* 161:5–11). The condition has a significant negative impact on the quality of life of the patient and their partner, often resulting in increased anxiety and tension which leads to depression and low self esteem. Whereas two decades ago, MED was primarily considered to be a psychological disorder (Benet, A. E. et al (1994), Male erectile dysfunction assessment and treatment options. *Comp. Ther.* 20: 669–673), it is now known that for the majority of patients there is an underlying organic cause. As a result, much progress has been made in identifying the mechanism of normal penile erection and the pathophysiology of MED.

Penile erection is a haemodynamic event which is dependent upon the balance of contraction and relaxation of the corpus cavernosal smooth muscle and vasculature of the penis (Lerner, S. E. et al (1993). A review of erectile dysfunction: new insights and more questions. *J. Urology* 149: 1246–1255). Corpus cavernosal smooth muscle is also referred to herein as corporal smooth muscle or in the plural sense corpus cavernosa. Relaxation of the corpus cavernosal smooth muscle leads to an increased blood flow into the trabecular spaces of the corpus cavernosa, causing them to expand against the surrounding tunica and compress the draining veins. This produces a vast elevation in blood pressure which results in an erection (Naylor, A. M. (1998). Endogenous neurotransmitters mediating penile erection. *Br. J. Urology* 81: 424–431).

The changes that occur during the erectile process are complex and require a high degree of co-ordinated control involving the peripheral and central nervous systems, and the endocrine system (Naylor, 1998). Corporal smooth muscle contraction is modulated by sympathetic noradrenergic innervation via activation of postsynaptic $\alpha_1$ adrenoceptors. MED may be associated with an increase in the endogenous smooth muscle tone of the corpus cavernosum. However, the process of corporal smooth muscle relaxation is mediated partly by non-adrenergic, non-cholinergic (NANC) neurotransmission. There are a number of other NANC neurotransmitters found in the penis, other than NO, such as calcitonin gene related peptide (CGRP) and vasoactive intestinal peptide (VIP). The main relaxing factor responsible for mediating this relaxation is nitric oxide (NO), which is synthesised from L-arginine by nitric oxide synthase (NOS) (Taub, H. C. et al (1993). Relationship between contraction and relaxation in human and rabbit corpus cavernosum. *Urology* 42: 698–704). It is thought that reducing corporal smooth muscle tone may aid NO to induce relaxation of the corpus cavernosum. During sexual arousal in the male, NO is released from neurones and the endothelium and binds to and activates soluble guanylate cyclase (sGC) located in the smooth muscle cells and endothelium, leading to an elevation in intracellular cyclic guanosine 3',5'-monophosphate (cGMP) levels. This rise in cGMP leads to a relaxation of the corpus cavernosum due to a reduction in the intracellular calcium concentration ($[Ca^{2+}]_i$), via unknown mechanisms thought to involve protein kinase G activation (possibly due to activation of $Ca^{2+}$ pumps and $Ca^{2+}$-activated $K^+$ channels).

The categories of female sexual dysfunction (FSD) are best defined by contrasting them to the phases of normal female sexual response: desire, arousal and orgasm (see S R Leiblum, (1998), Definition and Classification of Female Sexual Disorders, *Int. J. Impotence Res.*, 10, S104–S106). Desire or libido is the drive for sexual expression. Its manifestations often include sexual thoughts either when in the company of an interested partner or when exposed to other erotic stimuli. Arousal includes the vascular response to sexual stimulation, an important component of which is genital engorgement and increased vaginal lubrication, elongation of the vagina and increased genital sensation/sensitivity and a subjective excitement response. Orgasm is the release of sexual tension that has culminated during arousal. Hence, FSD occurs when a woman has an absent, inadequate or unsatisfactory response in any one or more of these phases, usually desire, arousal or orgasm.

The American Psychiatric Association classifies female sexual dysfunction (FSD) into four classes: FSAD, hypoactive sexual desire disorder (HSDD), female orgasmic disorder (FOD), and sexual pain disorders (e.g. dyspareunia and vaginismus) [see the American Psychiatric Association's Diagnostic and Statistical Manual of Mental Disorders, 4th Edition (DSM-IV)].

DSM-IV defines the four classes as follows:

HSDD—Persistently or recurrently deficient (or absent) sexual fantasies and desire for sexual activity. The judgement of deficiency or absence is made by the clinician, taking into account factors that affect functioning, such as age and the context of the persons life.

FSAD—Persistent or recurrent inability to attain, or to maintain until completion of the sexual activity, an adequate lubrication-swelling response of sexual excitement.

FOD—Persistent or recurrent delay in, or absence of, orgasm following a normal sexual excitement phase. Women exhibit wide variability in the type or intensity of stimulation that triggers orgasm. The diagnosis of FOD should be based on the clinician's judgement that the woman's orgasmic capacity is less than would be reasonable for her age, sexual experience, and the adequacy of the sexual stimulation she receives.

Sexual Pain Disorders such as Dyspareunia and Vaginismus. Dysparenuia—Recurrent or persistent genital pain associated with sexual intercourse. Vaginismus—Recurrent or persistent involuntary spasm of the musculature of the outer third of the vagina that interferes with sexual intercourse.

HSDD is present if a woman has no or little desire to be sexual, and has no or few sexual thoughts or fantasies. This type of FSD can be caused by low testosterone levels, due either to natural menopause or to surgical menopause. Other causes in both pre-menopausal woman (i.e. woman who are pre-menopausal and who have not have hysterectomies) as well as post-menopausal women include illness, medications, fatigue, depression and/or anxiety. Factors having a potential (conscious or sub-conscious) psychological impact such as relationship difficulties or religious factors may be related to the presence of/development of HSDD in females. The Diagnostic and Statistical Manual (DSM) IV of the American Psychiatric Association defines Female Sexual Arousal Disorder (FSAD) as being: "... a persistent or recurrent inability to attain or to maintain until completion of the sexual activity adequate lubrication-swelling response of sexual excitement. The disturbance must cause marked distress or interpersonal difficulty...".

The arousal response consists of vasocongestion in the pelvis, vaginal lubrication and expansion and swelling of the external genitalia. The disturbance causes marked distress and/or interpersonal difficulty.

FSAD is a highly prevalent sexual disorder affecting pre-, per- and post-menopausal (± hormone replacement therapy (HRT)) women. It is associated with concomitant disorders such as depression, cardiovascular diseases, diabetes and urogenital (UG) disorders. The primary consequences of FSAD are lack of engorgement/swelling, lack of lubrication and lack of pleasurable genital sensation. The secondary consequences of FSAD are reduced sexual desire, pain during intercourse and difficulty in achieving an orgasm. It has recently been hypothesised that there is a vascular basis for at least a proportion of patients with symptoms of FSAD (Goldstein et al., Int. J. Impot. Res., 10, S84–S90,1998) with animal data supporting this view (Park et al., Int. J. Impot. Res., 9, 27–37, 1997).

Drug candidates for treating FSAD, which are under investigation for efficacy, are primarily erectile dysfunction therapies that promote circulation to male genitalia. They consist of two types of formulation, oral or sublingual medications (Apomorphine, Phentolamine, phosphodiesterase type 5 (PDE5) inhibitors, e.g. Sildenafil), and prostaglandin ($PGE_1$) that are injected or administered transurethrally in men and topically to the genitalia in women.

The compounds of the present invention are advantageous by providing a means for restoring a normal sexual arousal response—namely increased genital blood flow leading to vaginal, clitoral and labial engorgement. This will result in increased vaginal lubrication via plasma transudation, increased vaginal compliance and increased genital sensitivity. Hence, the present invention provides a means to restore, or potentiate, the normal sexual arousal response.

By female genitalia herein we mean: "The genital organs consist of an internal and external group. The internal organs are situated within the pelvis and consist of ovaries, the uterine tubes, uterus and the vagina. The external organs are superficial to the urogenital diaphragm and below the pelvic arch. They comprise the mons pubis, the labia majora and minora pudendi, the clitoris, the vestibule, the bulb of the vestibule, and the greater vestibular glands" (Gray's Anatomy, C. D. Clemente, 13th American Edition). R. J. Levin teaches us that because "... male and female genitalia develop embryologically from the common tissue anlagen, [that] male and female genital structures are argued to be homologues of one another. Thus the clitoris is the penile homologue and the labia homologues of the scrotal sac...." (Levin, R. J. (1991), *Exp. Clin. Endocrinol.*, 98, 61–69).

In summary, FSAD is characterised by inadequate genital response to sexual stimulation. The genitalia do not undergo the engorgement that characterises normal sexual arousal. The vaginal walls are poorly lubricated, so that intercourse is painful. Orgasms may be impeded. Arousal disorder can be caused by reduced oestrogen at menopause or after childbirth and during lactation, as well as by illnesses, with vascular components such as diabetes and atherosclerosis. Other causes result from treatment with diuretics, antihistamines, antidepressants e.g. selective serotonin reuptake inhibitors (SSRIs) or antihypertensive agents.

FOD is the persistent or recurrent difficulty, delay in or absence of attaining orgasm following sufficient sexual stimulation and arousal, which causes personal distress.

Sexual pain disorders (includes dyspareunia and vaginismus) are characterised by pain resulting from penetration and sexual activity and may be caused by medications which reduce lubrication, endometriosis, pelvic inflammatory disease, inflammatory bowel disease or urinary tract problems.

According to a further aspect, the present invention additionally provides a method for the treatment and/or prevention of male sexual dysfunction (MSD), in particular male erectile dysfunction (MED) via treatment with a compound of the present invention as detailed hereinbefore. Particularly preferred for the treatment of MED as detailed herein is 6'-(3-Chloro-benzyloxy)-3,4,5,6-tetrahydro-2H-[1,2'] bipyrazinyl.

According to a yet further aspect, the present invention additionally provides a method for the treatment and/or prevention of male sexual dysfunction via treatment with a combination of a compound of the present invention as defined hereinbefore and one or more compounds which inhibit the activity of PDE, in particular compounds which inhibit the activity of cGMP PDE5, and/or one or more compounds which inhibit the activity of NEP.

Men who display an insufficient response or lack of response to treatment with Viagra™ may benefit either from therapy based on treatment with compounds of the present invention alone or via combination therapy based on compound(s) of the present invention and a cGMP PDE5i, such as for example sildenafil. Patients with mild to moderate MED should benefit from combined treatment based on compound(s) of the present invention alone or in combination with a NEPi, and patients with severe MED may also respond. Mild, moderate and severe MED will be terms known to the man skilled in the art, but guidance can be found in: *The Journal of Urology*, vol 151, 54–61 (January 1994).

MED patient groups, which are described in more detail in Clinical Andrology vol 23,no.4, p773–782, and chapter 3 of the book by I. Eardley and K. Sethia "Erectile Dysfunction—Current Investigation and Management, published by Mosby-Wolfe, are as follows: psyhcogenic, endocrinologic, neurogenic, arteriogenic, drug-induced sexual dysfunction (lactogenic) and sexual dysfunction related to cavernosal factors, particularly venogenic causes.

Suitable cGMP PDE5 inhibitors for the use in combination with a compound of the present invention for the treatment of MED according to the present invention include: the pyrazolo [4,3-d]pyrimidin-7-ones disclosed in EP-A-0463756; the pyrazolo [4,3-d]pyrimidin-7-ones disclosed in published international application WO 01/27112; the pyrazolo[4,3-d]pyrimidin-7-ones disclosed in published international application WO 01/27113; the indole-1,4-diones disclosed in WO95/19978 and the triazin-4-ones disclosed in published international application WO99/24433.

More preferred are compounds such as, 5-[2-ethoxy-5-(4-methyl-1-piperazinylsulphonyl)phenyl]-1-methyl-3-n-propyl-1,6-dihydro-7H-pyrazolo[4,3-d]pyrimidin-7-one (sildenafil) also known as 1-[[3-(6,7-dihydro-1-methyl-7-oxo-3-propyl-1H-pyrazolo[4,3-d]pyrimid in-5-yl)-4-ethoxyphenyl]sulphonyl]-4-methyl piperazine (see EP-A-0463756);

5-[2-ethoxy-5-(4-ethylpiperazin-1-ylsulphonyl)pyridin-3-yl]-3-ethyl-2-[2-methoxyethyl]-2,6-dihydro-7H-pyrazolo [4,3-d]pyrimidin-7-one, also known as 1-{6-ethoxy-5-[3-ethyl-6,7-dihydro-2-(2-methoxyethyl)-7-oxo-2H-pyrazolo [4,3-d]pyrimidin-5-yl]-3-pyridyisulphonyl}-4-ethylpiperazine (see WO 01/27113, Example 8);

5-(5-Acetyl-2-butoxy-3-pyridinyl)-3-ethyl-2-(1-ethyl-3-azetidinyl)-2,6-dihydro-7H-pyrazoleo[4,3-d]pyrimidin-7-one (see WO 01/27112, Example 132);

(6R,12aR)-2,3,6,7,12,12a-hexahydro-2-methyl-6-(3,4-methylenedioxyphenyl)-pyrazino[2',1':6,1]pyrido[3,4-b] indole-1,4-dione (IC-351, tadalafil), i.e. the compound of examples 78 and 95 of published international application WO95/19978, as well as the compound of examples 1, 3, 7 and 8; and 2-[2-ethoxy-5-(4-ethyl-piperazin-1-yl-1-sulphonyl)-phenyl]-5-methyl-7-propyl-3H-imidazo[5,1-f][1,2,4] triazin-4-one (vardenafil) also known as 1-[[3-(3,4-dihydro-5-methyl-4-oxo-7-propylimidazo[5,1-f]-as-triazin-2-yl)-4-ethoxyphenyl]sulphonyl]-4-ethylpiperazine (i.e. the compound of examples 20, 19, 337 and 336 of published international application WO99/24433); and pharmaceutically acceptable salts thereof.

According to a further aspect the present invention provides a composition for the treatment of MED comprising 6'-(3-Chloro-benzyloxy)-3,4,5,6-tetrahydro-2H-[1,2'] bipyrazinyl and sildenafil.

The suitability of any particular cGMP PDE5 inhibitor for use in combination with a compound of the present invention can be readily determined by evaluation of its potency and selectivity using literature methods followed by evaluation of its toxicity, absorption, metabolism, pharmacokinetics, etc in accordance with standard pharmaceutical practice.

Preferred cGMP PDE5 inhibitors for use herein have an $IC_{50}$ at less than 100 nanomolar, more preferably, at less than 50 nanomolar, more preferably still at less than 10 nanomolar. Preferably the CGMP PDE5 inhibitors for use in the pharmaceutical combinations according to the present invention are selective for the PDE5 enzyme. Preferably they have a selectivity of PDE5 over PDE3 of greater than 100 more preferably greater than 300. More preferably the PDE5 has a selectivity over both PDE3 and PDE4 of greater than 100, more preferably greater than 300.

Selectivity ratios may readily be determined by the skilled person. $IC_{50}$ values for the PDE3 and PDE4 enzyme may be determined using established literature methodology, see S A Ballard et al, Journal of Urology, 1998, vol. 159, pages 2164–2171.

Preferred herein are NEP inhibitors wherein said NEP is EC 3.4.24.11 and more preferably wherein said NEP inhibitor is a selective inhibitor for EC 3.4.24.11, more preferably a selective NEP inhibitor is a selective inhibitor for EC 3.4.24.11, which has an $IC_{50}$ of less than 100 nM (e.g. ompatrilat, candoxatril, candoxatrilat, sampatrilat). Suitable NEP inhibitor compounds are described in EP-A-1097719.

Particularly preferred NEPi compounds for as auxiliary agents for use in the treatment of MED according to the present invention are those described in co-pending International Patent Application PCT/IB02/00807 filed on the 18th Mar. 2002.

Especially preferred is (S)-2-[(1-{[3-(4-chlorophenyl) propyl]-carbamoyl}cyclo-pentyl)methyl]-4-methoxybutanoic acid or a pharmacuetically acceptable salt such as the sodium salt thereof as detailed at Example 22 in PCT/IB02/00807. Details for the synthesis of this compound and the sodium salt are provided in the Experimental Section hereinafter.

According to a further aspect the present invention provides a composition for the treatment of MED comprising 6'-(3-Chloro-benzyloxy)-3,4,5,6-tetrahydro-2H-[1,2'] bipyrazinyl and (S)-2-[(1-{[3-(4-chlorophenyl)propyl] carbamoyl}cyclo-pentyl)methyl]-4-methoxybutanoic acid.

According to yet a further aspect of the present invention, there is provided use of a compound of the present invention for the treatment of female sexual dysfunction (FSD).

According to another aspect of the present invention, there is provided use of a compound of the present invention and one or more additional active agents for the treatment of female sexual dysfunction (FSD).

Preferably, the one or more additional active agents is/are selected from the group consisting of:

1) estrogen receptor modulators and/or estrogen agonists and/or estrogen antagonists;
2) testosterone replacement agent and/or testosternone (Tostrelle) and/or dihydrotestosterone and/or dehydroepiandrosterone (DHEA) and/or a testosterone implant;
3) estrogen, estrogen and medroxyprogesterone or medroxyprogesterone acetate (MPA) (as a combination), or estrogen and methyl testosterone hormone replacement therapy agent;
4) one or more dopaminergic agents;
5) one or more of an NPY (neuropeptide Y) inhibitor;
6) one or more of a melanocortin receptor agonist or modulator or melanocortin enhancer;
7) one or more of an NEP (neutral endopeptidase) inhibitor;
8) one or more of a PDE (phosphodiesterase) inhibitor; and
9) one or more of a bombesin receptor antagonist or modulator.

Preferably, said FSD is female sexual arousal disorder (FSAD). Alternatively, said FSD is female orgasmic disorder (FOD). In a further alternative, said FSD is hypoactive sexual desire disorder (HSDD). In yet a further alternative, said FSD is a sexual pain disorder, preferably Dyspareunia or Vaginismus.

Examples of estrogen receptor modulators and/or estrogen agonists and/or estrogen antagonists, include raloxifene or lasofoxifene, (−)-cis-6-phenyl-5-[4-(2-pyrrolidin-1-yl-ethoxy)-phenyl]-5,6,7,8-tetrahydronaphthalene-2-ol and pharmaceutically acceptable salts thereof (compound (a) below), the preparation of which is detailed in WO 96/21656.

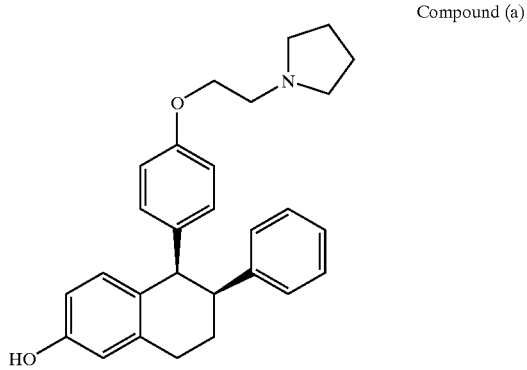

Compound (a)

An example of a testosterone replacement agent is dehydroandrostendione.

Examples of hormone replacement therapy agent include Premarin, Cenestin, Oestrofeminal, Equin, Estrace, Estrofem, Elleste Solo, Estring, Eastraderm TTS, Eastraderm Matrix, Dermestril, Premphase, Preempro, Prempak, Premique, Estratest, Estratest HS, and Tibolone.

Examples of dopaminergic agents include apomorphine or a selective D2, D3 or D2/D3 agonist such as, pramipexole and ropirinol (as claimed in WO-0023056), L-Dopa or carbidopa, PNU95666 (as disclosed in WO-0040226).

Examples of NPY (neuropeptide Y) inhibitors include NPY1 or NPY5 inhibitors, preferably NPY1 inhibitor. Preferably, said NPY inhibitors (including NPY Y1 and NPY Y5) having an IC50 of less than 100 nM, more preferably less than 50 nM. Suitable NPY, and in particular NPY1 inhibitor compounds, are described in EP-A-1097718.

Examples of a melanocortin receptor agonist or modulator or melanocortin enhancer include melanotan II, PT-14, PT-141 or compounds disclosed in WO-09964002, WO-00074679, WO-09955679, WO-00105401, WO-00058361, WO-00114879, WO-00113112 or WO-09954358.

Suitable NEP inhibitors are as described hereinabove.

According to a further aspect, the present invention provides a composition for the treatment of FSD comprising 6'-(3-Chloro-benzyloxy)-3,4,5,6-tetrahydro-2H-[1,2'] bipyrazinyl and (S)-2-[(1-{[3-(4-chlorophenyl)propyl]carbamoyl}cyclo-pentyl)methyl]-4-methoxybutanoic acid.

Preferred PDE inhibitors include a PDE 2, 3, 4, 5, 7 or 8 inhibitor, preferably PDE2 or PDE5 inhibitor and more preferably a PDE5 inhibitor (as described hereinabove), most preferably sildenafil.

According to a further aspect, the present invention provides a composition for the treatment of FSD comprising 6'-(3-Chloro-benzyloxy)-3,4,5,6-tetrahydro-2H-[1,2'] bipyrazinyl and sildenafil.

Preferred examples of one or more of bombesin receptor antagonists or modulators would be antagonists or modulators for $BB_1$, including those described in PCT/GB01/05018 (filed 14 Nov. 2001) and PCT/GB00/04380 (filed 17 Nov. 2000). Also preferred are bombesin $BB_2$, $BB_3$, or $BB_4$ receptor antagonists. Preferred bombesin receptor antagonists are also mentioned as "auxiliary agents" in PCT/IB01/02399 (filed 10 Dec. 2001).

It should be noted that a full list of possible "additional active agents" can be found in PCT/IB01/02399 (filed 10 Dec. 2001)—and are described as "auxiliary agents" therein.

In accordance with yet another aspect of the present invention, other 5-$HT_{2c}$ receptor agonists may be used in addition to a compound of the present invention. Such 5-$HT_{2c}$ receptor agonists include, but are not limited to, those disclosed in Chaki and Nakazato—Expert Opin. Ther. Patents (2001), 11(11):1677–1692 (see especially Section 3.9—5$HT_{2c}$, on page 1687 and FIG. 7 on page 1686), or Isaac—Drugs of the Future (2001), 26(4):383–393 (see especially FIG. 2 on page 385). For the avoidance of doubt, the aforementioned publications are incorporated herein by reference in their entireties.

Preferably, said 5-$HT_{2c}$ receptor agonists are selective 5-$HT_{2c}$ receptor agonists.

Receptor binding data or binding selectivity data may not always correlate with or reflect functional data or functional selectivity data. For example, a compound may be a 5-$HT_{2c}$ receptor agonist when binding assays are analysed, but functionally the compound may have the same potency at other 5-HT receptors. Thus, the term "selective" as used herein in relation to the present invention with respect to methods of treatment for sexual dysfunction means "functionally selective".

Thus, according to another aspect, the present invention additionally provides the use of 5-$HT_{2c}$ receptor agonists, preferably selective 5-$HT_{2c}$ receptor agonists, for the treatment of FSD, preferably FSAD, FOD, HSDD or a sexual pain disorder (such as Dyspareunia or Vaginismus).

According to the methods of the invention, a compound of the present invention or a combination of a compound of the present invention and at least one additional pharmaceutical agent is administered to a subject in need of such treatment, preferably in the form of a pharmaceutical composition. In the combination aspect of the invention, the compound of the present invention and at least one other pharmaceutical agent (e.g., anti-obesity agent described above) may be administered either separately or in the pharmaceutical composition comprising both. It is generally preferred that such administration be oral. However, if the subject being treated is unable to swallow, or oral administration is otherwise impaired or undesirable, parenteral or transdermal administration may be appropriate.

According to the methods of the invention, when a combination of a compound of the present invention and at least one other pharmaceutical agent are administered together, such administration can be sequential in time or simultaneous with the simultaneous method being generally preferred. For sequential administration, a compound of the present invention and the additional pharmaceutical agent can be administered in any order. It is generally preferred that such administration be oral. It is especially preferred that such administration be oral and simultaneous. When a compound of the present invention and the additional pharmaceutical agent are administered sequentially, the administration of each can be by the same or by different methods.

According to the methods of the invention, a compound of the present invention or a combination of a compound of the present invention and at least one additional pharmaceutical agent (referred to herein as a "combination") is preferably administered in the form of a pharmaceutical composition. Accordingly, a compound of the present invention or a combination can be administered to a patient separately or together in any conventional oral, rectal, transdermal, parenteral, (for example, intravenous, intramuscular, or subcutaneous) intracisternal, intravaginal, intraperitoneal, intravesical, local (for example, powder, ointment or drop), or buccal, or nasal, dosage form.

Compositions suitable for parenteral injection generally include pharmaceutically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Prevention of microorganism contamination of the compositions can be accomplished with various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and gelatin.

Solid dosage forms for oral administration include capsules, tablets, powders, and granules. In such solid dosage forms, a compound of the present invention or a combination is admixed with at least one inert customary pharmaceutical excipient (or carrier) such as sodium citrate or dicalcium phosphate or (a) fillers or extenders (e.g., starches, lactose, sucrose, mannitol, silicic acid and the like); (b) binders (e.g., carboxymethylcellulose, alginates, gelatin, polyvinylpyrrolidone, sucrose, acacia and the like); (c) humectants (e.g., glycerol and the like); (d) disintegrating agents (e.g., agar-agar, calcium carbonate, potato or tapioca starch, alginic acid, certain complex silicates, sodium carbonate and the like); (e) solution retarders (e.g., paraffin and the like); (f) absorption accelerators (e.g., quaternary ammonium compounds and the like); (g) wetting agents (e.g., cetyl alcohol, glycerol monostearate and the like); (h) adsorbents (e.g., kaolin, bentonite and the like); and/or (i) lubricants (e.g., talc, calcium stearate, magnesium stearate, solid polyethylene glycols, sodium lauryl sulfate and the like). In the case of capsules and tablets, the dosage forms may also comprise buffering agents.

Solid compositions of a similar type may also be used as fillers in soft or hard filled gelatin capsules using such excipients as lactose or milk sugar, as well as high molecular weight polyethylene glycols, and the like.

Solid dosage forms such as tablets, dragees, capsules, and granules can be prepared with coatings and shells, such as enteric coatings and others well known in the art. They may also contain opacifying agents, and can also be of such composition that they release the compound of the present invention and/or the additional pharmaceutical agent in a delayed manner. Examples of embedding compositions that can be used are polymeric substances and waxes. The drug can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the compound of the present invention or the combination, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed oil, groundnut oil, corn germ oil, olive oil, castor oil, sesame seed oil and the like), glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

Suspensions, in addition to the compound of the present invention or the combination, may further comprise suspending agents, e.g., ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal or vaginal administration preferably comprise suppositories, which can be prepared by mixing a compound of the present invention or a combination with suitable non-irritating excipients or carriers, such as cocoa butter, polyethylene glycol or a suppository wax which are solid at ordinary room temperature but liquid at body temperature and therefore melt in the rectum or vaginal cavity thereby releasing the active component(s).

Dosage forms for topical administration of the compounds of the present invention and combinations of the compounds of the present invention with anti-obesity agents may comprise ointments, powders, sprays and inhalants.

The drugs are admixed under sterile condition with a pharmaceutically acceptable carrier, and any preservatives, buffers, or propellants that may be required. Ophthalmic formulations, eye ointments, powders, and solutions are also intended to be included within the scope of the present invention.

The following paragraphs describe exemplary formulations, dosages, etc. useful for non-human animals. The administration of the compounds of the present invention and combinations of the compounds of the present invention with anti-obesity agents can be effected orally or non-orally (e.g., by injection).

An amount of a compound of the present invention or combination of a compound of the present invention with an anti-obesity agent is administered such that an effective dose is received. Generally, a daily dose that is administered orally to an animal is between about 0.01 and about 1,000 mg/kg of body weight, preferably between about 0.01 and about 300 mg/kg of body weight.

Conveniently, a compound of the present invention (or combination) can be carried in the drinking water so that a therapeutic dosage of the compound is ingested with the daily water supply. The compound can be directly metered into drinking water, preferably in the form of a liquid, water-soluble concentrate (such as an aqueous solution of a water-soluble salt).

Conveniently, a compound of the present invention (or combination) can also be added directly to the feed, as such, or in the form of an animal feed supplement, also referred to as a premix or concentrate. A premix or concentrate of the compound in a carrier is more commonly employed for the inclusion of the agent in the feed. Suitable carriers are liquid or solid, as desired, such as water, various meals such as alfalfa meal, soybean meal, cottonseed oil meal, linseed oil meal, corncob meal and corn meal, molasses, urea, bone meal, and mineral mixes such as are commonly employed in poultry feeds. A particularly effective carrier is the respective animal feed itself; that is, a small portion of such feed. The carrier facilitates uniform distribution of the compound in the finished feed with which the premix is blended. Preferably, the compound is thoroughly blended into the premix and, subsequently, the feed. In this respect, the compound may be dispersed or dissolved in a suitable oily vehicle such as soybean oil, corn oil, cottonseed oil, and the like, or in a volatile organic solvent and then blended with the carrier. It will be appreciated that the proportions of compound in the concentrate are capable of wide variation since the amount of the compound in the finished feed may be adjusted by blending the appropriate proportion of premix with the feed to obtain a desired level of compound.

High potency concentrates may be blended by the feed manufacturer with proteinaceous carrier such as soybean oil meal and other meals, as described above, to produce concentrated supplements, which are suitable for direct feeding to animals. In such instances, the animals are permitted to consume the usual diet. Alternatively, such concentrated supplements may be added directly to the feed to produce a nutritionally balanced, finished feed containing a therapeutically effective level of a compound of the present invention. The mixtures are thoroughly blended by standard procedures, such as in a twin shell blender, to ensure homogeneity.

If the supplement is used as a top dressing for the feed, it likewise helps to ensure uniformity of distribution of the compound across the top of the dressed feed.

Drinking water and feed effective for increasing lean meat deposition and for improving lean meat to fat ratio are generally prepared by mixing a compound of the present invention with a sufficient amount of animal feed to provide from about $10^{-3}$ to about 500 ppm of the compound in the feed or water.

The preferred medicated swine, cattle, sheep and goat feed generally contain from about 1 to about 400 grams of a compound of the present invention (or combination) per ton of feed, the optimum amount for these animals usually being about 50 to about 300 grams per ton of feed.

The preferred poultry and domestic pet feeds usually contain about 1 to about 400 grams and preferably about 10 to about 400 grams of a compound of the present invention (or combination) per ton of feed.

For parenteral administration in animals, the compounds of the present invention (or combination) may be prepared in the form of a paste or a pellet and administered as an implant, usually under the skin of the head or ear of the animal in which increase in lean meat deposition and improvement in lean meat to fat ratio is sought.

In general, parenteral administration involves injection of a sufficient amount of a compound of the present invention (or combination) to provide the animal with about 0.01 to about 20 mg/kg/day of body weight of the drug. The preferred dosage for poultry, swine, cattle, sheep, goats and domestic pets is in the range of from about 0.05 to about 10 mg/kg/day of body weight of drug.

Paste formulations can be prepared by dispersing the drug in a pharmaceutically acceptable oil such as peanut oil, sesame oil, corn oil or the like.

Pellets containing an effective amount of a compound of the present invention, pharmaceutical composition, or combination can be prepared by admixing a compound of the present invention or combination with a diluent such as carbowax, carnuba wax, and the like, and a lubricant, such as magnesium or calcium stearate, can be added to improve the pelleting process.

It is, of course, recognized that more than one pellet may be administered to an animal to achieve the desired dose level which will provide the increase in lean meat deposition and improvement in lean meat to fat ratio desired. Moreover, implants may also be made periodically during the animal treatment period in order to maintain the proper drug level in the animal's body.

The present invention has several advantageous veterinary features. For the pet owner or veterinarian who wishes to increase leanness and/or trim unwanted fat from pet animals, the instant invention provides the means by which this may be accomplished. For poultry and swine breeders, utilization of the method of the present invention yields leaner animals that command higher sale prices from the meat industry.

Embodiments of the present invention are illustrated by the following Examples. It is to be understood, however, that the embodiments of the invention are not limited to the specific details of these Examples, as other variations thereof will be known, or apparent in light of the instant disclosure, to one of ordinary skill in the art.

EXAMPLES

Unless specified otherwise, starting materials are generally available from commercial sources such as Aldrich Chemicals Co. (Milwaukee, Wis.), Lancaster Synthesis, Inc. (Windham, N.H.), Acros Organics (Fairlawn, N.J.), Maybridge Chemical Company, Ltd. (Cornwall, England), Tyger Scientific (Princeton, N.J.), and AstraZeneca Pharmaceuticals (London, England).

General Experimental Procedures

NMR spectra were recorded on a Varian Unity™ 400 (available from Varian Inc., Palo Alto, Calif.) at room temperature at 400 MHz for proton. Chemical shifts are expressed in parts per million (δ) relative to residual solvent as an internal reference. The peak shapes are denoted as follows: s, singlet; d, doublet; t, triplet; q, quartet; m, multiplet; bs, broad singlet; 2s, two singlets. Atmospheric pressure chemical ionization mass spectra (APCI) were obtained on a Fisons™ Platform II Spectrometer (carrier gas: acetonitrile: available from Micromass Ltd, Manchester, UK). Chemical ionization mass spectra (CI) were obtained on a Hewlett-Packard™ 5989 instrument (ammonia ionization, PBMS: available from Hewlett-Packard Company, Palo Alto, Calif.). Electrospray ionization mass spectra (ES) were obtained on a Waters™ ZMD instrument (carrier gas: acetonitrile: available from Waters Corp., Milford, Mass.). Where the intensity of chlorine or bromine-containing ions are described, the expected intensity ratio was observed (approximately 3:1 for $^{35}Cl/^{37}Cl$-containing ions and 1:1 for $^{79}Br/^{81}Br$-containing ions) and the intensity of only the lower mass ion is given. In some cases only representative $^1H$ NMR peaks are given. MS peaks are reported for all examples. Optical rotations were determined on a PerkinElmer™ 241 polarimeter (available from PerkinElmer Inc., Wellesley, Mass.) using the sodium D line (λ=589 nm) at the indicated temperature and are reported as follows $[\alpha]_D^{temp}$, concentration (c=g/100 mL), and solvent.

Column chromatography was performed with either Baker™ silica gel (40 μm; J. T. Baker, Phillipsburg, N.J.) or Silica Gel 50 (EM Sciences™, Gibbstown, N.J.) in glass columns or in Flash 40 Biotage™ columns (ISC, Inc., Shelton, Conn.) under low nitrogen pressure.

Example 1

Preparation of Intermediate 6'-Chloro-2,3,5,6-tetrahydro-[1,2']bipyrazinyl-4-carboxylic acid tert-butyl ester (I-1a)

A mixture of 2,6-dichloropyrazine (2.98 g, 20 mmol), piperazine-1-carboxylic acid tert-butyl ester (3.72 g, 20 mmol) and sodium carbonate (2.12 g, 20 mmol) in t-butanol (50 mL) was heated at reflux under nitrogen for 65 h. The solution was concentrated in vacuo. The residue was partitioned between ethyl acetate (50 mL) and water (50 mL). The aqueous phase was extracted with ethyl acetate (3×30 mL). The combined organic extracts were washed with brine (50 mL), dried over magnesium sulfate, filtered, and concentrated in vacuo to give the title compound (I-1a) as a white solid.

$^1H$ NMR (400 MHz, $CDCl_3$) δ 7.96 (s, 1H); 7.82 (s, 1H); 3.52–3.60 (m, 8H); 1.46 (s, 9H). MS (ES$^+$) Calc: 298.1, Found: 299.1 (M+1).

Preparation of Intermediate 6'-(3-Chloro-benzyloxy)-2,3,5,6-tetrahydro-[1,2']bipyrazinyl-4-carboxylic acid tert-butyl ester (I-1b)

A mixture of 6'-chloro-2,3,5,6-tetrahydro-[1,2']bipyrazinyl-4-carboxylic acid tert-butyl ester (I-1a) (300 mg, 1.0 mmol), 3-chlorobenzyl alcohol (0.142 mL, 1.2 mmol), KOH (191 mg, 3.4 mmol) and 18-crown-6 (10.6 mg, 0.04 mmol) in toluene (6 mL) was stirred at reflux for 5.5 h and concentrated in vacuo. The residue was partitioned between $H_2O$ (30 mL) and $CH_2Cl_2$ (30 mL). The aqueous phase was separated and extracted with $CH_2Cl_2$ (2×30 mL). The combined organic extracts were dried and concentrated in vacuo. The crude product was purified by preparative TLC (5% MeOH in $CH_2Cl_2$) to afford the title compound (I-1b) (380 mg).

$^1H$ NMR (400 MHz, $CDCl_3$) δ 7.63 (s, 1H); 7.59 (s, 1H); 7.40 (s, 1H); 7.27 (s, 3H); 5.26 (s, 2H); 3.51 (s, 8H); 1.46 (s, 9H). MS (ES$^+$) Calc: 404.1, Found: 405.0 (M+1).

Preparation of 6'-(3-Chloro-benzyloxy)-3,4,5,6-tetrahydro-2H-[1,2']bipyrazinyl (1-A)

To a solution of 6'-(3-chloro-benzyloxy)-2,3,5,6-tetrahydro-[1,2']bipyrazinyl-4-carboxylic acid tert-butyl (I-1b) (380 mg, 0.94 mmol) in $CH_2Cl_2$ (6 mL) was added trifluoroacetic acid (1.4 mL). After stirring at room temperature for 2 h, the solution was concentrated in vacuo. The residue was partitioned between 1M HCl (20 mL) and EtOAc (30 mL). The aqueous phase was washed with EtOAc (2×30 mL), basified with 3 N NaOH, and extracted with EtOAc (3×30 mL). The combined organic extracts were concentrated in vacuo to give the title compound (1-A) (252 mg) as an oil.

$^1H$ NMR (400 MHz, $CDCl_3$) δ 7.62 (s, 1H); 7.56 (s, 1H); 7.40 (s, 1H); 7.28–7.25 (m, 3H); 5.26 (s, 2H); 3.49 (t, 4H); 2.95 (t, 4H); 1.96 (s, 1H). MS (ES$^+$) Calc: 304.1, Found: 305.1 (M+1).

Preparation of 6'-(3-Chloro-benzyloxy)-3,4,5,6-tetrahydro-2H-[1,2']bipyrazinyl, hydrochloride (1-B)

To a solution of 6'-(3-chloro-benzyloxy)-3,4,5,6-tetrahydro-2H-[1,2']bipyrazinyl (1-A) in $CH_2Cl_2$ (4 mL) was added dropwise 1M HCl in ether (1.5 mL) and then hexane (4 mL) was added. The solid was collected and dried to give the hydrochloride salt (1-B) (300 mg).

$^1H$ NMR (400 MHz, $CD_3OD$) δ 7.98 (br s, 1H); 7.72 (s, 1H); 7.50 (s, 1H); 7.39–7.33 (m, 3H); 5.48 (br s, 2H); 4.00 (br s, 4H); 3.35 (bs, 4H). MS (ES$^+$) Calc: 304.1, Found: 305.1 (M+1).

Preparation of 6'-(3-Chloro-benzyloxy)-3,4,5,6-tetrahydro-2H-[1,2']bipyrazinyl, fumarate (1-C)

To a solution of 6'-(3-chloro-benzyloxy)-3,4,5,6-tetrahydro-2H-[1,2']bipyrazinyl 1-A (252 mg, 0.83 mmol) in a mixture of isopropyl ether (8 mL) and MeOH (1 mL) was added 0.5 M fumaric acid in MeOH (1.86 mL, 0.93 mmol) in one portion. The resulting mixture was stirred at room temperature for 1 h. The white solid was collected by filtration and washed with isopropyl ether followed by hexane and dried in vacuo to give the title compound 1-C.

$^1H$ NMR (400 MHz, $CD_3OD$) δ 7.77 (s, 1H); 7.59 (s, 1H); 7.44 (d, 1H); 7.34–7.28 (m, 3H); 6.67 (s, 2H); 5.35 (s, 2H); 3.82–3.79 (m, 4H); 3.29–3.2. (m, 4H). MS (APCI$^+$) Calc: 304.1, Found: 305.4 (M+1).

Preparation of 6'-(3-Chloro-benzyloxy)-3,4,5,6-tetrahydro-2H-[1,2']bipyrazinyl, succinate (1-D)

To a solution of 6'-(3-chloro-benzyloxy)-3,4,5,6-tetrahydro-2H-[1,2']bipyrazinyl 1-A (183 mg, 0.60 mmol) in a mixture of isopropyl ether (3 mL) and MeOH (1 mL) was added 0.5 M succinic acid in MeOH (1.32 mL, 0.66 mmol) in one portion. The resulting solution was concentrated. The residue was dissolved in a mixture of MeOH (0.5 mL) and isopropyl ether (4 mL). The clear solution was kept at room temperature for 19 h. The white solid was collected by filtration and washed with isopropyl ether followed by hexane and dried in vacuo to give the title compound 1-D (240 mg).

$^1H$ NMR (400 MHz, $CD_3OD$) δ 7.75 (s, 1H); 7.57 (s, 1H); 7.44 (d, 1H); 7.34–7.29 (m, 3H); 5.35 (s, 2H); 3.79–3.76 (m,

4H); 3.30–3.28. (m, 4H); 2.50 (s, 4H). MS (APCl⁺) Calc: 304.1, Found: 305.3 (M+1).

Using the appropriate starting materials, the compounds listed in Table 1 were prepared in an analogous manner to the sequence of reactions described above for the preparation of compound (1-A) or its corresponding hydrochloride salt (1-B), fumarate salt (1-C), or succinate salt (1-D). Other salts were prepared from the corresponding free bases using similar procedures.

TABLE 1

| Ex. No. | Compound Name | MS Calc. | Found (M + 1) |
|---|---|---|---|
| 1-E | 6'-(3-Trifluoromethoxy-benzyloxy)-3,4,5,6-tetrahydro-2H-[1,2']bipyrazinyl | 354.1 | 355.1 |
| 1-F | 6'-(3-Trifluoromethyl-benzyloxy)-3,4,5,6-tetrahydro-2H-[1,2']bipyrazinyl | 338.1 | 339.1 |
| 1-G | 6'-Benzyloxy-3,4,5,6-tetrahydro-2H-[1,2']bipyrazinyl, hydrochloride | 270.2 | 271.2 |
| 1-H | 6'-(2-Fluoro-benzyloxy)-3,4,5,6-tetrahydro-2H-[1,2']bipyrazinyl | 288.1 | 289.1 |
| 1-I | 6'-(3-Fluoro-benzyloxy)-3,4,5,6-tetrahydro-2H-[1,2']bipyrazinyl, hydrochloride, | 288.1 | 289.1 |
| 1-J | 6'-(2-Chloro-benzyloxy)-3,4,5,6-tetrahydro-2H-[1,2']bipyrazinyl | 304.1 | 305.1 |
| 1-K | 6'-(3-Chloro-benzyloxy)-(2S)-methyl-3,4,5,6-tetrahydro-2H-[1,2']bipyrazinyl | 318.1 | 319.1 |
| 1-L | 6'-(3-Chloro-benzyloxy)-(2R)-methyl-3,4,5,6-tetrahydro-2H-[1,2']bipyrazinyl | 318.1 | 319.1 |
| 1-M | 6'-(2,5-Difluoro-benzyloxy)-3,4,5,6-tetrahydro-2H-[1,2']bipyrazinyl | 306.1 | 307.1 |
| 1-N | 6'-(3,5-Dichloro-benzyloxy)-3,4,5,6-tetrahydro-2H-[1,2']bipyrazinyl | 338.1 | 339.0 |
| 1-O | 6'-(3,5-Difluoro-benzyloxy)-3,4,5,6-tetrahydro-2H-[1,2']bipyrazinyl | 306.1 | 307.1 |
| 1-P | 6'-(2-Trifluoromethyl-benzyloxy)-3,4,5,6-tetrahydro-2H-[1,2']bipyrazinyl | 338.1 | 339.1 |
| 1-Q | 6'-(2-Trifluoromethoxy-benzyloxy)-3,4,5,6-tetrahydro-2H-[1,2']bipyrazinyl | 354.1 | 355.1 |
| 1-R | 6'-(4-Chloro-benzyloxy)-3,4,5,6-tetrahydro-2H-[1,2']bipyrazinyl | 304.1 | 305.1 |
| 1-S | 6'-(4-Fluoro-benzyloxy)-3,4,5,6-tetrahydro-2H-[1,2']bipyrazinyl | 288.1 | 289.1 |
| 1-T | 6'-(2,5-Dichloro-benzyloxy)-3,4,5,6-tetrahydro-2H-[1,2']bipyrazinyl | 338.1 | 339.0 |
| 1-U | 6'-(3-Chloro-benzyloxy)-(3R)-methyl-3,4,5,6-tetrahydro-2H-[1,2']bipyrazinyl | 318.1 | 319.1 |
| 1-V | 6'-(3-Chloro-benzyloxy)-(3R,5S)-dimethyl-3,4,5,6-tetrahydro-2H-[1,2']bipyrazinyl | 331.1 | 332.1 |
| 1-W | 6'-(3,5-Bis-trifluoromethyl-benzyloxy)-3,4,5,6-tetrahydro-2H-[1,2']bipyrazinyl | 406.1 | 407.3 |
| 1-X | 6'-(3-Fluoro-5-trifluoromethyl-benzyloxy)-3,4,5,6-tetrahydro-2H-[1,2']bipyrazinyl | 356.1 | 357.3 |
| 1-Z | 6'-[1-(3,5-Difluoro-phenyl)-ethoxy]-3,4,5,6-tetrahydro-2H-[1,2']bipyrazinyl | 320.1 | 321.3 |
| 1-AA | 6'-(3,5-Dimethyl-benzyloxy)-3,4,5,6-tetrahydro-2H-[1,2']bipyrazinyl | 298.1 | 299.3 |
| 1-AB | 6'-(2,5-Dimethyl-benzyloxy)-3,4,5,6-tetrahydro-2H-[1,2']bipyrazinyl | 298.1 | 299.3 |
| 1-AC | 6'-(2,5-Difluoro-benzyloxy)-3,4,5,6-tetrahydro-2H-[1,2']bipyrazinyl, fumarate | 306.3 | 307.3 |
| 1-AD | 6'-(3-Chloro-benzyloxy)-(2R)-methyl-3,4,5,6-tetrahydro-2H-[1,2']bipyrazinyl, fumarate | 318.1 | 319.3 |
| 1-AE | 6'-[(1R)-Phenyl-ethoxy]-3,4,5,6-tetrahydro-2H-[1,2']bipyrazinyl | 284.4 | 285.3 |
| 1-AF | 6'-[(1S)-Phenyl-ethoxy]-3,4,5,6-tetrahydro-2H-[1,2']bipyrazinyl | 284.4 | 285.3 |
| 1-AG | 6'-(2-Chloro-benzyloxy)-(2R)-methyl-3,4,5,6-tetrahydro-2H-[1,2']bipyrazinyl | 318.1 | 319.3 |
| 1-AH | 6'-(2-Fluoro-benzyloxy)-(2R)-methyl-3,4,5,6-tetrahydro-2H-[1,2']bipyrazinyl | 302.3 | 303.3 |
| 1-AI | 6'-(3-Fluoro-benzyloxy)-(2R)-methyl-3,4,5,6-tetrahydro-2H-[1,2']bipyrazinyl | 302.3 | 303.3 |
| 1-AJ | 6'-(2,5-Dichloro-benzyloxy)-(2R)-methyl-3,4,5,6-tetrahydro-2H-[1,2']bipyrazinyl | 352.1 | 353.3 |
| 1-AK | 6'-(3-Chloro-benzyloxy)-(3S)-methyl-3,4,5,6-tetrahydro-2H-[1,2']bipyrazinyl | 318.1 | 319.6 |
| 1-AL | 6'-(3-Fluoro-benzyloxy)-(3S)-methyl-3,4,5,6-tetrahydro-2H-[1,2']bipyrazinyl | 302.4 | 303.4 |
| 1-AM | 6'-(Naphthalen-1-ylmethoxy)-3,4,5,6-tetrahydro-2H-[1,2']bipyrazinyl, hydrochloride | 320.4 | 321.3 |
| 1-AN | 6'-(2,3-Difluoro-benzyloxy)-3,4,5,6-tetrahydro-2H-[1,2']bipyrazinyl | 306.3 | 307.3 |
| 1-AO | 6'-(2,3-Dichloro-benzyloxy)-3,4,5,6-tetrahydro-2H-[1,2']bipyrazinyl | 338.1 | 339.2 |
| 1-AP | 6'-(2-Chloro-benzyloxy)-3,4,5,6-tetrahydro-2H-[1,2']bipyrazinyl, fumarate | 304.2 | 305.3 |
| 1-AQ | 6'-(Indan-(1S)-yloxy)-3,4,5,6-tetrahydro-2H-[1,2']bipyrazinyl | 296.4 | 297.3 |
| 1-AR | 6'-(Indan-(1R)-yloxy)-3,4,5,6-tetrahydro-2H-[1,2']bipyrazinyl | 296.4 | 297.3 |
| 1-AS | 6'-(3-Chloro-benzyloxy)-4-methyl-3,4,5,6-tetrahydro-2H-[1,2']bipyrazinyl | 318.1 | 319.3 |
| 1-AT | 6'-(3-Fluoro-benzyloxy)-4-methyl-3,4,5,6-tetrahydro-2H-[1,2']bipyrazinyl | 302.4 | 303.4 |
| 1-AU | 6'-(2-Fluoro-benzyloxy)-3,4,5,6-tetrahydro-2H-[1,2']bipyrazinyl hydrochloride salt | 288.1 | 289.1 |
| 1-AV | 6'-(Pyridin-3-ylmethoxy)-3,4,5,6-tetrahydro-2H-[1,2']bipyrazinyl | 271.1 | 272.3 |
| 1-AW | 6'-(Pyridin-2-ylmethoxy)-3,4,5,6-tetrahydro-2H-[1,2']bipyrazinyl hydrochloride salt | 271.1 | 272.3 |
| 1-AX | 6'-(3,4-Difluoro-benzyloxy)-3,4,5,6-tetrahydro-2H-[1,2']bipyrazinyl | 306.1 | 307.4 |
| 1-AY | 6'-(3,4-Dichloro-benzyloxy)-3,4,5,6-tetrahydro-2H-[1,2']bipyrazinyl | 339.1 | 339.3 |
| 1-AZ | 6'-[2-(3-Chloro-phenyl)-ethoxy]-3,4,5,6-tetrahydro-2H-[1,2']bipyrazinyl | 318.1 | 319.4 |
| 1-BA | 6'-[2-(4-Chloro-phenyl)-ethoxy]-3,4,5,6-tetrahydro-2H-[1,2']bipyrazinyl | 318.1 | 319.4 |
| 1-BB | 6'-[2-(3-Fluoro-phenyl)-ethoxy]-3,4,5,6-tetrahydro-2H-[1,2']bipyrazinyl | 302.1 | 303.4 |
| 1-BC | 6'-(3-Nitro-benzyloxy)-3,4,5,6-tetrahydro-2H-[1,2']bipyrazinyl | 315.1 | 316.3 |
| 1-BD | 3-(3,4,5,6-Tetrahydro-2H-[1,2']bipyrazinyl-6'-yloxymethyl)-phenylamine | 285.1 | 286.3 |
| 1-BE | 3-(3,4,5,6-Tetrahydro-2H-[1,2']bipyrazinyl-6'-yloxymethyl)-benzamide | 313.1 | 314.3 |
| 1-BF | 6'-([1,2,3]Thiadiazol-4-ylmethoxy)-3,4,5,6-tetrahydro-2H-[1,2']bipyrazinyl | 278.1 | 279.2 |
| 1-BG | 6'-(6-Methyl-pyridin-2-ylmethoxy)-3,4,5,6-tetrahydro-2H-[1,2']bipyrazinyl | 285.2 | 286.4 |
| 1-BH | 6'-(Furan-3-ylmethoxy)-3,4,5,6-tetrahydro-2H-[1,2']bipyrazinyl | 260.2 | 261.4 |
| 1-BI | 6'-(3-Chloro-benzyloxy)-2-ethyl-3,4,5,6-tetrahydro-2H-[1,2']bipyrazinyl | 332.1 | 333.4 |
| 1-BJ | 6'-(3-Chloro-thiophen-2-ylmethoxy)-3,4,5,6-tetrahydro-2H-[1,2']bipyrazinyl hydrochloride salt | 310.1 | 311.3 |
| 1-BK | 6'-(Thiophen-2-ylmethoxy)-3,4,5,6-tetrahydro-2H-[1,2']bipyrazinyl | 276.1 | 277.3 |
| 1-BL | 6'-(Thiophen-3-ylmethoxy)-3,4,5,6-tetrahydro-2H-[1,2']bipyrazinyl | 276.1 | 277.3 |
| 1-BM | 2-Methyl-6'-(pyridin-2-ylmethoxy)-3,4,5,6-tetrahydro-2H-[1,2']bipyrazinyl | 285.1 | 286.3 |
| 1-BN | 2-Methyl-6'-(pyridin-3-ylmethoxy)-3,4,5,6-tetrahydro-2H-[1,2']bipyrazinyl | 285.1 | 286.3 |
| 1-BO | 2-Methyl-6'-(6-methyl-pyridin-2-ylmethoxy)-3,4,5,6-tetrahydro-2H-[1,2']bipyrazinyl, fumarate | 299.2 | 300.4 |
| 1-BP | 6'-(6-Methoxy-pyridin-2-ylmethoxy)-3,4,5,6-tetrahydro-2H-[1,2']bipyrazinyl | 301.1 | 302.3 |
| 1-BQ | Methyl-(6-methyl-pyridin-2-ylmethyl)-(3,4,5,6-tetrahydro-2H-[1,2']bipyrazinyl-6'-yl)-amine | 298.2 | 299.4 |
| 1-BR | (3-Fluoro-benzyl)-(2-methyl-3,4,5,6-tetrahydro-2H-[1,2']bipyrazinyl-6'-yl)-amine | 301.2 | 302.3 |
| 1-BS | (6-Methyl-pyridin-2-ylmethyl)-(3,4,5,6-tetrahydro-2H-[1,2']bipyrazinyl-6'-yl)-amine formate salt | 284.2 | 285.3 |

TABLE 1-continued

| Ex. No. | Compound Name | MS Calc. | Found (M + 1) |
|---|---|---|---|
| 1-BT | (3-Chloro-benzyl)-(2-methyl-3,4,5,6-tetrahydro-2H-[1,2']bipyrazinyl-6'-yl)-amine | 317.1 | 318.3 |
| 1-BU | 6'-(2-Methoxy-pyridin-3-ylmethoxy)-3,4,5,6-tetrahydro-2H-[1,2']bipyrazinyl | 301.1 | 302.2 |
| 1-BV | 6'-(2,4-Dichloro-benzyloxy)-3,4,5,6-tetrahydro-2H-[1,2']bipyrazinyl | 338.1 | 339.1 |
| 1-BW | 6'-(2-Methyl-benzyloxy)-3,4,5,6-tetrahydro-2H-[1,2']bipyrazinyl | 284.2 | 285.2 |
| 1-BX | 6'-(3-Methoxy-benzyloxy)-3,4,5,6-tetrahydro-2H-[1,2']bipyrazinyl | 300.1 | 301.2 |
| 1-BY | 6'-(3-Chloro-benzyloxy)-2,5-dimethyl-3,4,5,6-tetrahydro-2H-[1,2']bipyrazinyl | 332.1 | 333.2 |
| 1-BZ | 6'-(2-Chloro-benzyloxy)-2,5-dimethyl-3,4,5,6-tetrahydro-2H-[1,2']bipyrazinyl | 332.1 | 333.2 |
| 1-CA | 6'-(3-Fluoro-benzyloxy)-2,5-dimethyl-3,4,5,6-tetrahydro-2H-[1,2']bipyrazinyl | 316.2 | 317.3 |
| 1-CB | 6'-Benzylsulfanyl-3,4,5,6-tetrahydro-2H-[1,2']bipyrazinyl | 286.1 | 287.4 |
| 1-CC | 6'-(3-Chloro-benzylsulfanyl)-3,4,5,6-tetrahydro-2H-[1,2']bipyrazinyl | 320.1 | 321.4 |
| 1-CD | 6'-(4-Methyl-thiazol-2-ylmethoxy)-3,4,5,6-tetrahydro-2H-[1,2']bipyrazinyl | 291.1 | 292.2 |
| 1-CE | 6'-(3-Bromo-benzyloxy)-3,4,5,6-tetrahydro-2H-[1,2']bipyrazinyl hydrochloride | 348.1 | 349.1 |
| 1-CF | 6'-(3-methy-benzyloxy)-3,4,5,6-tetrahydro-2H-[1,2']bipyrazinyl hydrochloride | 284.2 | 285.2 |
| 1-CG | 6'-(4-Piperidin-1-ylmethyl-benzyloxy)-3,4,5,6-tetrahydro-2H-[1,2']bipyrazinyl | 367.2 | 368.5 |
| 1-CH | 6'-[1-(2-Fluoro-pyridin-3-yl)-ethoxy]-3,4,5,6-tetrahydro-2H-[1,2']bipyrazinyl | 303.1 | 304.4 |
| 1-CI | 6'-(7,8-Difluoro-quinolin-3-ylmethoxy)-3,4,5,6-tetrahydro-2H-[1,2']bipyrazinyl | 357.1 | |
| 1-CJ | 6'-(2-Phenyl-pyrrolidin-1-yl)-3,4,5,6-tetrahydro-2H-[1,2']bipyrazinyl | 309.2 | 310.2 |

Example 2

Preparation of Intermediate (3-Chloro-benzyl)-(6-chloro-pyrazin-2-yl)-amine (I-2a)

To a solution of 2-amino-6-chloropyrazine (100 mg, 0.77 mmol) in 7.7 mL of anhydrous toluene was added 3-chlorobenzaldehyde (87.4 µL, 0.77 mmol) followed by 50 mg of activated, powdered 4 Å molecular sieves. The reaction was refluxed under nitrogen for 3 h, then cooled to ambient temperature and treated with sodium borohydride (43.0 mg, 1.16 mmol). The resultant slurry was heated to reflux under nitrogen overnight. After cooling to ambient temperature the reaction was filtered through a pad of Celite®, and the flitrate was concentrated in vacuo to a brown residue. Chromatography on a silica gel preparatory TLC plate (1:1 hexane:ethyl acetate) provided 71.0 mg of the title compound I-2a.

$^1$H NMR (400 MHz, CDCL$_3$) δ 7.78 (s, 1H); 7.71 (s, 1H); 7.35–7.25 (m, 4H); 5.53 (bs, 1H); 4.53 (d, 2H). MS (ES$^+$) Calc: 253, Found: 254.3 (M+1).

Preparation of Intermediate 6'-(3-Chloro-benzylamino)-2,3,5,6-tetrahydro-[1,2']bipyrazinyl-4-carboxylic acid tert-butyl ester (I-2b)

A mixture of (3-chloro-benzyl)-(6-chloro-pyrazin-2-yl)-amine (I-2a) (71.0 mg, 0.28 mmol), piperazine-1-carboxylic acid tert-butyl ester (260.2 mg, 1.40 mmol) and 1,8-diazabicyclo[5.4.0]undec-7-ene (208.9 µL, 1.40 mmol) in 1.0 mL of ethanol was refluxed for 18 h under nitrogen. The reaction was then cooled to ambient temperature and poured into 20 mL of water. This was extracted 2×30 mL of ethyl acetate and the combined organic extracts were washed with 3×15 mL water followed by 15 mL of brine. The organic layer was then dried over sodium sulfate, filtered and concentrated in vacuo to a yellow residue that was chromatographed (prep. TLC, 1:1 hexane:ethyl acetate) to give the title compound (I-2b) as a white solid, 13.5 mg.

$^1$H NMR (400 MHz, CDCL$_3$) δ 7.38 (s, 1H); 7.31 (s, 1H); 7.25–7.18 (m, 4H); 4.81 (bs, 1H); 4.48 (d, 2H); 3.46 (bs, 8H); 1.46 (s, 9H). MS (ES$^+$) Calc: 403, Found: 404.3 (M+1).

Preparation of (3-Chloro-benzyl)-(3,4,5,6-tetrahydro-2H-[1,2']bipyrazinyl-6'-yl)-amine (2-A)

The title compound (2-A) was prepared from 6'-(3-chloro-benzylamino)-2,3,5,6-tetrahydro-[1,2']bipyrazinyl-4-carboxylic acid tert-butyl ester (I-2b). To a solution of (I-2b) in CH$_2$Cl$_2$ was added trifluoroacetic acid. After stirring at room temperature for 3 h, the mixture was poured into 1N NaOH and extracted with CH$_2$Cl$_2$ (1×35 mL). The organic layer was washed with brine, dried and concentrated to afford the title compound as a free amine (2-A).

$^1$H NMR (400 MHz, CD$_3$OD) δ 7.33 (s, 1H); 7.27–7.15 (m, 5H); 4.46 (s, 2H); 3.41 (dd, 4H); 2.81 (dd, 4H). MS (ES$^+$) Calc: 303.2, Found: 304.3 (M+1).

Example 3

Example 3 illustrates alternative methods for preparing compounds of the present invention wherein W is oxygen and further illustrates compounds of the present invention where W is oxygen not illustrated in Example 1.

Example 3-A

Preparation of Intermediate 3-(6-Chloro-pyrazin-2-yloxymethyl)-benzonitrile (I-3a)

To a solution of 3-hydroxymethyl-benzonitrile (2.0 g, 15.0 mmol) and 2,6-dichloro-pyrazine (2.24 g, 15.0 mmol) in THF (150 mL) was added 60% NaH in mineral oil (0.9 g, 22.5 mmol). After stirring at ambient temperature for 2 h, the reaction mixture was poured into 1N HCl (100 mL) and extracted with Ethyl Acetate (1×250 mL). The organic layer was washed with brine, dried (Na$_2$SO$_4$), filtered, and concentrated to dryness. The crude material was chromatographed over Silica Gel (40 g) eluting with hexanes (1000 mL) followed by ethyl acetate (500 mL) to obtain 3.53 g of the desired pure product (I-3a) as a white solid.

MS (ES$^+$) Calc.: 245.0, Found: 246.1 (M+1). $^1$HNMR (CDCl$_3$): δ 8.20 (d, 2H), 7.75(d, 1H), 7.69–7.62 (m, 2H), 7.5(t, 1H), 5.40(s, 2H).

Preparation of Intermediate 3-(3,4,5,6-Tetrahydro-2H-[1,2']bipyrazinyl-6'-yloxymethyl)-benzonitrile (I-3b)

A mixture of 3-(6-chloro-pyrazin-2-yloxymethyl)-benzonitrile I-3a (3.53 g, 14.4 mmol) and piperazine (12.4 g, 143.70 mmol) in ethanol (144 mL) was stirred under reflux for 48 h. The reaction mixture was concentrated to dryness and the residue was dissolved in ethyl acetate (300 mL). The ethyl acetate solution was washed with H$_2$O (4×125 mL), brine (125 mL), dried (Na$_2$SO$_4$), filtered, and concentrated to dryness. The crude material was chromatographed over Silica Gel (40 g) using 5% methanol/methylene chloride with 1% NH$_4$OH as the eluant to give 3.03 g of the desired product (I-3b) as a white solid.

MS (ES$^+$) Calc.: 295.1, Found: 296.2 (M+1). $^1$HNMR (CDCl$_3$): δ 7.71(d, 1H), 7.68–7.58(2s+m, 4H), 7.47(m, 1H), 5.32(s, 2H), 3.54–3.50(m, 4H), 2.98–2.95(m, 4H).

Preparation of 3-(3 4,5,6-Tetrahydro-2H-[1,2'] bipyrazinyl-6'-yloxymethyl)-benzamide (3-A)

A solution of 3-(3,4,5,6-tetrahydro-2H-[1,2']bipyrazinyl-6'-yloxy-methyl)-benzonitrile I-3b (3.03 g, 10.3 mM) in a mixture of methanol (10 mL) and 1N NaOH (51.3 mL, 51.3 mmol) was heated at 60° C. for 24 h. The reaction mixture was partitioned between $H_2O$ (150 mL) and ethyl acetate (300 mL). The organic layer was washed with $H_2O$, brine, dried ($Na_2SO_4$), filtered, and concentrated to dryness. The crude material was chromatographed over Silica Gel (40 g) using 10% methanol/methylene chloride with 1% $NH_4OH$ as the eluant to yield 834 mg of the title compound (3-A) as a white solid.

MS (ES$^+$) Calc.: 313.2, Found: 314.3 (M+1). $^1$HNMR (CDCl$_3$): δ 7.96(d, 1H), 7.80–7.78(dd, 1H), 7.62–7.59(s+m, 1H), 7.46–7.42(s+m, 2H), 5.39 (s, 2H), 3.53–3.51(m, 4H), 2.87–2.84(m, 4H).

Example 3-B

Preparation of Intermediate 2-Chloromethyl-6-fluoro-pyridine (I-3c)

Compound I-3d was prepared according to the procedure described in the *J.Org.Chem.*, 2000, 65, 7718–7722.

Preparation of Intermediate (6-Fluoro-pyridin-2-yl)-methanol (I-3d)

To a solution of 2-chloromethyl-6-fluoro-pyridine I-3c (1.43 g, 9.84 mmol) in $H_2O$ (22 mL) was added $K_2CO_3$ (1.77 g, 12.8 mmol). The reaction mixture was stirred overnight at reflux. The cooled aqueous mixture was first extracted with heptane (2×20 mL)and then ethyl acetate (2×50 mL). The ethyl acetate layers were combined, washed with brine, dried ($Na_2SO_4$), and concentrated to dryness. The crude residue was chromatographed over silica gel (15 g) using 2% methanol/methylene chloride with 0.5% $NH_4OH$ as the eluant to yield 518.7 mg of the title compound (I-3d) as a yellow oil.

$^1$HNMR (CDCl$_3$): δ 7.81–7.75(q, 1H), 7.19–7.17(m, 1H), 6.84–6.81(m, 1H), 4.72 (s, 2H).

Preparation of Intermediate 2-Chloro-6-(6-fluoro-pyridin-2-ylmethoxy)-pyrazine (I-3e)

To a solution of (6-fluoro-pyridin-2-yl)-methanol I-3d (368 mg, 2.89 mmol) and 2,6-dichloro-pyrazine (431.2 mg, 2.89 mM) in THF (14.7 mL) at room temperature was added 60% NaH in mineral oil (174 mg, 4.34 mmol). The resulting mixture was stirred at ambient temperature for 19 h and concentrated. The residue was purified by column chromatography (ethyl acetate/hexanes=1:4)) to afford 560 mg of the title compound (I-3e).

MS (ES$^+$) Calc.: 239.1, Found: 240.1 (M+1). $^1$HNMR (CDCl$_3$): δ 8.24(s, 1H), 8.19 (s, 1H), 7.85–7.79(q, 1H), 7.34–7.32(dd, 1H), 6.91–6.88(dd, 1H), 5.42 (s, 2H).

Preparation of 6'-(6-Fluoro-pyridin-2-ylmethoxy)-3,4,5,6-tetrahydro-2H-[1,2']bipyrazinyl (3-B)

Following the general procedure for the preparation of I-3b above, 2-chloro-6-(6-fluoro-pyridin-2-ylmethoxy)-pyrazine (100 mg, 0.42 mmol) and piperazine (360 mg, 4.17 mmol) were reacted to give the title compound (3-B). The crude material was purified by preparative TLC using 5% methanol/methylene chloride with 1% $NH_4OH$ as the eluant to yield 23 mg of the title product (3-B).

MS (ES$^+$) Calc.: 289.1, Found: 290.2 (M+1). $^1$HNMR (CDCl$_3$): δ 7.80–7.74(q, 1H), 7.64–7.63 (2s, 2H), 7.32–7.30 (dd, 1H), 6.84–6.82(dd, 1H), 5.36 (s, 2H), 3.49–3.46 (m, 4H), 2.94–2.92 (m, 4H), 2.23 (br s, 1H).

Using the appropriate starting materials, the compounds listed in Table 2 were prepared in an analogous manner to the sequence of reactions described above for the preparation of compounds (3-A and 3-B).

TABLE 2

| Ex. No. | Compound Name | MS Calc. | Found (M + 1) |
|---|---|---|---|
| 3-C | 6'-(2-Pyridin-3-yl-ethoxy)-3,4,5,6-tetrahydro-2H-[1,2']bipyrazinyl | 285.4 | 286.4 |
| 3-D | 6'-(6-Chloro-pyridin-2-ylmethoxy)-3,4,5,6-tetrahydro-2H-[1,2']bipyrazinyl | 305.8 | 306.3 |

Example 3-E

Preparation of Intermediate 3-(6-Chloro-pyrazin-2-yloxymethyl)-benzonitrile (I-3f)

A mixture of 2,6-dichloropyrazine (400 mg, 0.671 mmol), 3-hydroxymethyl-benzonitrile (428 mg, 0.805 mmol), KOH (181 mg, 0.805 mmol) and 18-crown-6 (28 mg, 0.027 mmol) in toluene (10 mL) was stirred at reflux for 6 h and concentrated in vacuo. The residue was partitioned between $H_2O$ and ethyl acetate. The aqueous phase was separated and extracted with ethyl acetate twice. The combined organic extracts were washed with water and brine, dried and concentrated in vacuo. The crude product I-3f (667.2 mg) was used for next step without further purification.

Preparation 3-(3,4,5,6-Tetrahydro-2H-[1,2'] bipyrazinyl-6'-yloxymethyl-benzonitrile (3-E)

A mixture of 3-(6-chloro-pyrazin-2-yloxymethyl)-benzonitrile I-3f (667.2 mg, 2.716 mmol), piperazine (297 mg, 3.531 mmol), sodium t-butoxide (287 mg, 2.987 mmol), BINAP (67.7 mg, 0.109 mmol), and Pd$_2$(dba)$_3$ (49.7 mg, 0.054 mmol) in toluene (10 mL) was heated at 90° C. overnight. The solution was cooled to room temperature and filtered through a celite pad. The celite pad was washed with ethyl acetate several times. The combined filtrate was concentrated in vacuo to give the crude title compound. The product was purified by chromatography (silica, 10% MeOH/dichlormethane with 1% $NH_4OH$) to give 180 mg 3-(3,4,5,6-tetrahydro-2H-[1,2']bipyrazinyl-6'-yloxymethyl)-benzonitrile (3-E).

NMR (400 MHz, CD$_3$OD) δ 7.81 (s, 1H); 7.74 (d, 1H); 7.65 (m, 2H); 7.54 (t, 1H); 7.48 (s, 1H); 5.40 (s, 2H); 3.54 (t, 4H); 3.88(t, 4H). MS (ES$^+$) Calc: 295.1, Found: 296.3 (M+1).

Example 3-F

Preparation of Intermediate 3'-Chloro-6'-(3-chloro-benzyloxy)-3,4,5,6-tetrahydro-2H-[1,2']bipyrazinyl-4-carboxylic acid tert-butyl ester (I-3h) and Intermediate 5'-Chloro-6'-(3-chloro-benzyloxy)-3,4,5,6-tetrahydro-2H-[1,2']bipyrazinyl-4-carboxylic acid tert-butyl ester (I-3g)

A solution of 6'-(3-chloro-benzyloxy)-2,3,5,6-tetrahydro-[1,2']bipyrazinyl-4-carboxylic acid tert-butyl ester (1-1b)

(322 mg, 0.80 mmol) in CHCl$_3$ (10 ml) at 0° C. under a nitrogen atmosphere was treated with N-chlorosuccinamide (106 mg, 0.80 mmol). The resulting mixture was allowed to warm to room temperature and stirred for 16 h. The reaction mixture was partitioned between CHCl$_2$ and saturated aqueous NaHCO$_3$ solution. The organic phase was washed with twice with saturated aqueous NaHCO$_3$ solution and once with brine, dried over MgSO$_4$ (anhydrous), filtered and concentrated in vacuo. The residue was purified by flash chromatography (CHCl$_2$-EtOAc 99:1 to 95:5). Three compounds were obtained in the following elution order: dichlorinated material (45 mg, 13%), Compound I-3g (116 mg, 33%) and Compound I-3h (30 mg, 7%). The structures of the two monochlorinated products were assigned by nOe experiments.

Compound I-3g: $^1$H NMR (400 MHz, CDCl$_3$) δ 1.46 (s, 9H), 3.34–3.37 (m, 4H), 3.51–3.54 (m, 4H), 5.25 (s, 2H), 7.24–7.26 (m, 3H), 7.37 (s, 1H), 7.57 (s, 1H). MS (ES$^+$) Calc: 438.1, Found: 439.2 (M+1).

Compound I-3h: $^1$H NMR (400 MHz, CDCl$_3$) δ 1.48 (s, 9H), 3.48–3.57 (m, 8H), 5.35 (s, 2H), 7.29–7.33 (m, 3H), 7.41–7.42 (m, 2H). MS (ES$^+$) Calc: 438.1, Found: 439.2 (M+1).

Preparation of 3'-Chloro-6'(3-chloro-benzyloxy)-3,4,5,6-tetrahydro-2H-[1,2']bipyrazinyl hydrochloride (3-F)

A solution of 3'-Chloro-6'-(3-chloro-benzyloxy)-3,4,5,6-tetrahydro-2H-[1,2']bipyrazinyl-4-carboxylic acid tert-butyl ester (Compound I-3g) (40 mg, 0.091 mmol) in 1,4-dioxane (0.5 ml) at 23° C. was treated with HCl in 1,4-dioxane (4 M, 0.23 ml, 0.91 mmol). The resulting mixture was stirred at room temperature for 5 h (during which a precipitate appeared) and treated with ether. The solid was collected by filtration and washed with ether to afford the title compound 3-F (27 mg, 72%).

$^1$H NMR (400 MHz, DMSO-d$_6$) δ 3.18 (bs, 4H), 3.55 (bs, 4H), 5.35 (s, 2H), 7.40 (m, 3H), 7.52 (s, 1H), 7.77 (s, 1H), 9.32–9.39 (m, 2H) MS (ES$^+$) Calc: 338.1, Found: 339.3 (M+1).

Example 3-G

5'-Fluoro-6'-(3-chloro-benzyloxy)-3,4,5,6-tetrahydro-2H-[1,2']bipyrazinyl-4-carboxylic acid tert-butyl ester (I-3i): and 3'-Fluoro-6'-(3-chloro-benzyloxy)-3,4,5,6-tetrahydro-2H-[1,2']bipyrazinyl-4-carboxylic acid tert-butyl ester (I-3i')

A solution of 6'-(3-chloro-benzyloxy)-2,3,5,6-tetrahydro-[1,2']bipyrazinyl-4-carboxylic acid tert-butyl ester (1-1b) (600 mg, 1.49 mmol) in acetonitrile (12.4 ml) at 0° C. under a nitrogen atmosphere was treated with Selectfluor™ ([1-(chloromethyl)-4-fluoro-1,4-diazoniabicyclo[2.2.2]-octane bis(tetrafluoroborate)]) (526 mg, 1.49 mmol). The resulting mixture was allowed to warm to room temperature and stirred for 16 h. The reaction mixture was partitioned between CH$_2$Cl$_2$ and water. The organic phase was washed twice with water, twice with saturated aqueous NaHCO$_3$ solution and twice with brine, dried over MgSO$_4$ (anhydrous), filtered and concentrated in vacuo. The residue was purified by flash chromatography (CHCl$_2$-EtOAc 99:1 to 95:5). Three compounds were obtained in the following elution order: difluorinated material (160 mg, 25%), Intermediate I-3i (32 mg, 5%) and Intermediate I-3i' (141 mg, 22%). The structures of the two monofluorinated products were assigned by nuclear Overhauser effect (nOe) experiments.

Intermediate I-3i: $^1$H NMR (400 MHz, CDCl$_3$) δ 1.48 (s, 9H), 3.41 (m, 4H), 3.54 (m, 4H), 5.36 (s, 2H), 7.05 (d, J=3, 1H), 7.30 (m, 3H), 7.43 (s, 1H). MS (ES$^+$) Calc: 422.2, Found: 423.4 (M+1).

Intermediate I-3i': $^1$H NMR (400 MHz, CDCl$_3$) δ 1.45 (s, 9H), 3.49 (m, 8H), 5.22 (s, 2H), 7.10 (d, J=3, 1H), 7.25 (m, 3H), 7.37 (s, 1H) MS (ES$^+$) Calc: 422.2, Found: 423.2 (M+1).

Preparation of 6'-(3-Chloro-benzyloxy)-5'-fluoro-3,4,5,6-tetrahydro-2H-[1,2']bipyrazinyl formate (3-G)

A solution of 6'-(3-chloro-benzyloxy)-5'-fluoro-3,4,5,6-tetrahydro-2H-[1,2']bipyrazinyl-4-carboxylic acid tert-butyl ester (I-3i) (50 mg, 0.12 mmol) in formic acid (96%, 0.5 ml) was stirred at room temperature for 2 h, and concentrated in vacuo. The residue was triturated three times with ether. The title compound 3-I was collected as a white solid (15 mg, 34%). MS (ES$^+$) Calc: 322.1, Found: 323.4 (M+1).

Example 3-H

Preparation of 3'-Bromo-6'-(3-chloro-benzyloxy)-3,4,5,6-tetrahydro-2H-[1,2']bipyrazinyl-4-carboxylic acid tert-butyl ester (I-3j) and 5'-Bromo-6'-(3-chloro-benzyloxy)-3,4,5,6-tetrahydro-2H-[1,2'] bipyrazinyl-4-carboxylic acid tert-butyl ester (I-3j')

A solution of 6'-(3-chloro-benzyloxy)-2,3,5,6-tetrahydro-[1,2']bipyrazinyl-4-carboxylic acid tert-butyl ester (1-1b) (1.5 g, 3.7 mmol) in CHCl$_3$ (44 ml) at 0° C. under a nitrogen atmosphere was treated with N-bromosuccinamide (6.49 mg, 3.53 mmol). The resulting mixture was allowed to warm to room temperature and stirred for 16 h. The reaction mixture was partitioned between CH$_2$Cl$_2$ and saturated aqueous NaHCO$_3$ solution. The organic phase was washed with saturated aqueous NaHCO$_3$ solution and with brine, dried over MgSO$_4$ (anhydrous), filtered and concentrated in vacuo. The residue was purified by flash chromatography (CHCl$_2$-EtOAc 99:1 to 96:4). Three compounds were obtained in the following elution order: dibrominated material (68 mg, 4%), Intermediate I-3j (176 mg, 10%) and Intermediate I-3j' (805 mg, 45%). The structures of the two monobrominated products were assigned by nuclear Overhauser effect (nOe) experiments.

Intermediate I-3j: $^1$H NMR (400 MHz, CDCl$_3$) δ 1.49 (s, 9H), 3.32–3.37 (m, 4H), 3.55–3.58 (m, 4H), 5.28 (s, 2H), 7.27–7.31 (m, 3H), 7.41 (s, 1H), 7.65 (s, 1H). MS (ES$^+$) Calc: 482.1, Found: 483.4 (M+1).

Intermediate I-3j': $^1$H NMR (400 MHz, CDCl$_3$) δ 1.48 (s, 9H), 3.50 (m, 8H), 5.35 (s, 2H), 7.28–7.32 (m, 3H), 7.43 (m, 2H). MS (ES$^+$) Calc: 482.1, Found: 483.4 (M+1).

Preparation of Intermediate 6'-(3-Chloro-benzyloxy)-3'-methyl-3,4,5,6-tetrahydro-2H-[1,2'] bipyrazinyl-4-carboxylic acid tert-butyl ester (I-3k)

A mixture of 3'-bromo-6'-(3-chloro-benzyloxy)-3,4,5,6-tetrahydro-2H-[1,2']bipyrazinyl-4-carboxylic acid tert-butyl ester (I-3j) (82 mg, 0.17 mmol), methylboronic acid (15.3 mg, 0.25 mmol), K$_3$PO$_4$ (72 mg, 0.34 mmol), dppf (4.7 mg, 0.0085 mmol) and PdCl$_2$dppf(CH$_2$Cl$_2$)$_2$ (6.9 mg, 0.0085 mmol) in THF (anhydrous, 1.2 ml) under a nitrogen atmosphere was heated to reflux for 16 h. The reaction mixture was cooled to room temperature and filtered through a pad of silica gel, eluting with EtOAc-hexane (6:4). The filtrate was concentrated in vacuo. The residue was purified by preparative TLC (EtOAc-hexane 1:1) to provide 72 mg of the title compound I-3k (>99% yield).

MS (ES$^+$) Calc: 418.2, Found: 419.2 (M+1).

Preparation of 6'-(3-Chloro-benzyloxy)-3'-methyl-3, 4,5,6-tetrahydro-2H-[1,2']bipyrazinyl hydrochloride (3-H)

A solution of Intermediate I-3k (72 mg, 0.17 mmol) in HCl in 1,4-dioxane (4 M, 1.0 ml, 4 mmol) at 23° C. was stirred at room temperature for 1 h (during which a precipitate appeared) and treated with ether. The solid was collected by filtration and washed with ether to afford 50 mg of the title compound 3-H (75% yield).

MS (ES$^+$) Calc: 318.1, Found: 319.2 (M+1).

The compounds listed in Table 3 were prepared using analogous procedures to those used for the preparation of 3-F (hydrochloride salt) and 3-G (formate salt) using either N-chlorosuccinamide, N-bromosuccinamide, or Selectfluor for introducing the halogen onto the pyrazine ring.

TABLE 3

| Ex. No. | Compound Name | MS Calc. | Found (M + 1) |
|---|---|---|---|
| 3-I | 5'-Chloro-6'-(3-chloro-benzyloxy)-3,4,5,6-tetrahydro-2H-[1,2']bipyrazinyl hydrochloride | 338.1 | 339.3 |
| 3-J | 3'-Fluoro-6'-(3-chloro-benzyloxy)-3,4,5,6-tetrahydro-2H-[1,2']bipyrazinyl hydrochloride | 322.1 | 323.4 |
| 3-K | 5'-Fluoro-6'-(3-chloro-benzyloxy)-3,4,5,6-tetrahydro-2H-[1,2']bipyrazinyl formate | 322.1 | 323.4 |
| 3-L | 3'-Bromo-6'-(3-chloro-benzyloxy)-3,4,5,6-tetrahydro-2H-[1,2']bipyrazinyl formate | 382.0 | 383.2 |
| 3-M | 5'-Bromo-6'-(3-chloro-benzyloxy)-3,4,5,6-tetrahydro-2H-[1,2']bipyrazinyl hydrochloride | 382.0 | 383.1 |

Example 3-N

Preparation of Intermediate 3-Chloro-5-(3-chloro-benzyloxy)-pyrazine (I-3l)

A solution of 3-chlorobenyl alcohol (9.57 g, 67.1 mmol) in toluene (134 ml) at 23° C. under a nitrogen atmosphere was treated with NaH (60% dispersion in oil, 2.5 g, 67.1 mmol). The resulting suspension was heated to reflux for 30 min and cooled to room temperature. The mixture was treated with 2,6-dichloropyrazine (10.0 g, 67.1 mmol) and heated to reflux for 18 h. The reaction mixture was cooled to room temperature and partitioned between water and EtOAc. The organic phase was washed with brine, dried over MgSO$_4$ (anhydrous), filtered and concentrated in vacuo. The residue was purified by flash chromatography (CH$_2$Cl$_2$-hexanes 3:7) to afford 10.0 g of the title compound (I-3l) as a clear oil (58%).

$^1$H NMR (400 MHz, CDCl$_3$) δ 5.36 (s, 2H), 7.33 (m, 3H), 8.18 (s, 1H), 8.19 (s, 1H) MS (ES$^+$) Calc: 254.0, Found: 255.2 (M+1).

Preparation of Intermediate 3-Chloro-5-(3-chloro-benzyloxy)-pyrazine 1-oxide (I-3m)

A solution of 3-chloro-5-(3-chloro-benzyloxy)-pyrazine I-3l (500 mg, 1.97 mmol) in CHCl$_3$ (10 ml) at 0° C. under a nitrogen atmosphere, was treated with 680 mg (3.94 mmol) m-chloroperbenzoic acid (mCPBA). The resulting mixture was allowed to warm to room temperature, stirred at 23° C. for 16 h, heated at reflux for 2 h and cooled to room temperature. The reaction mixture was treated with Ca(OH)$_2$ (680 mg, 3.94 mmol), stirred at room temperature for 3 h and filtered. The solid was washed with CH$_2$Cl$_2$. The filtrate and washings were combined, dried over MgSO$_4$ (anhydrous), filtered, and concentrated in vacuo. The residue was purified by flash chromatography (EtOAc-hexanes 4:6) to provide 465 mg of the title compound (I-3m) as a white solid (87%).

$^1$H NMR (400 MHz, CDCl$_3$) δ 5.3 (s, 2H), 7.27 (m, 3H), 7.36 (s, 1H), 7.69 (s, 1H), 7.77 (s, 1H) MS (ES$^+$) Calc: 270.0, Found: 271.2 (M+1).

Preparation of Intermediate 6'-(3-Chloro-benzyloxy)-3,4,5,6-tetrahydro-2H-[1,2']bipyrazinyl 4'-oxide-4-carboxylic acid tert-butyl ester (I-3n)

A solution of 3-chloro-5-(3-chloro-benzyloxy)-pyrazine 1-oxide (I-3m) (200 mg, 0.74 mmol) in acetonitrile (2 ml) under a nitrogen atmosphere was treated with piperazine-1-carboxylic acid tert-butyl ester (343 mg, 1.85 mmol) and heated at reflux for 5 h. The reaction mixture was cooled to room temperature and partitioned between water and EtOAc. The organic phase was washed with saturated aqueous NaHCO$_3$ solution and was dried over MgSO$_4$ (anhydrous), filtered and concentrated in vacuo. The residue was purified by preparative TLC (EtOAc-hexanes 1:1) to provide 200 mg of the title compound I-3n (64%).

$^1$H NMR (400 MHz, CDCl$_3$) δ 1.48 (s, 9H), 3.5 (m, 8H), 5.3 (s, 2H), 7.31 (m, 3H), 7.38 (s, 1H) MS (ES$^+$) Calc: 420.2, Found: 421.4 (M+1).

Preparation of 6'-(3-Chloro-benzyloxy)-3,4,5,6-tetrahydro-2H-[1,2']bipyrazinyl 4'-oxide hydrochloride (3-N)

A solution of 6'-(3-chloro-benzyloxy)-3,4,5,6-tetrahydro-2H-[1,2']bipyrazinyl 4'-oxide-4-carboxylic acid tert-butyl ester (I-3n) (100 mg, 0.24 mmol) in HCl in 1,4-dioxane (4 M, 2.0 ml, 8 mmol) at 23° C. was stirred at room temperature for 20 min (during which a precipitate appeared). The solid was collected by filtration and washed with ether to afford 85 mg of the title compound 3-N (99%).

$^1$H NMR (400 MHz, DMSO-d$_6$) δ 3.10 (bs, 4H), 3.73 (bs, 4H), 5.34 (s, 2H), 7.39–7.5 (m, 5H), 7.73 (s, 1H), 9.26–9.32 (m, 2H) MS (ES$^+$) Calc: 320.1, Found: 321.3 (M+1).

Example 3-O

Preparation of Intermediate 5-Bromo-3-(3-chloro-benzyloxy)-pyrazin-2-ylamine (I-3o)

3-Chlorobenzyl alcohol (2.36 mL, 20 mmol) was added slowly with vigorous stirring to a suspension of NaH (60% dispersion in mineral oil, 0.80 g, 20 mmol) in THF (25 mL) at room temperature under dry nitrogen with vigorous gas evolution. The resulting suspension was stirred for 10 min at room temperature. 2-Amino-3,5-dibromopyrazine (2.53 g, 10 mmol) was added in a single portion to give a dark amber solution. The solution was heated to reflux for 2 h then cooled to room temperature. The solvent was removed in vacuo to give an oily brown solid which was dissolved in EtOAc (50 mL). The EtOAc solution was washed with saturated aqueous NaHCO$_3$ (75 mL). The NaHCO$_3$ solution was back extracted with EtOAc (2×75 mL). The combined EtOAc extracts were washed with water (100 mL) and brine (75 mL), dried over Na$_2$SO$_4$, filtered, and concentrated to a viscous oily solid. The residue was filtered through a plug of silica gel, eluting with $CH_2Cl_2$, discarding the first two void volumes, and the filtrate was concentrated to a pinkish solid. The solid was dissolved in $Et_2O$ (50 mL) and treated with 4 M HCl in 1,4-dioxane (10 mL, 40 mmol). The resulting suspension was stirred 30 min at room temperature and the precipitate collected by filtration, washing with $Et_2O$ (3×10 mL). The off-white solid obtained was dried in vacuo to give 2.63 g of the hydrochloride salt. The salt was converted to the free base by vigorous stirring at room temperature in saturated aqueous $NaHCO_3$ (100 mL) and EtOAc (100 mL). After 30 min, the phases were separated and the aqueous phase was extracted with EtOAc (2×50 mL). The combined extracts were washed with brine, dried over $Na_2SO_4$ (anhydrous), filtered, and concentrated in vacuo to give the title compound I-3o as a pink solid (1.83 g, 58% yield).

$^1$H NMR (400 MHz, $CDCl_3$) δ 7.67 (s, 1H); 7.44 (d, 1H); 7.35–7.31 (m, 3H); 5.36 (s, 2H); 4.87 (broad s, 2H). MS ($ES^+$) Calc: 313.0, Found: 314.2 (M+1).

Preparation of Intermediate [5-Bromo-3-(3-chloro-benzyloxy)-pyrazin-2-yl]-carbamic acid tert-butyl ester (I-3p)

5-Bromo-3-(3-chloro-benzyloxy)-pyrazin-2-ylamine I-3o (1.82 g, 5.8 mmol) and triethylamine (1.22 mL, 8.7 mmol) were dissolved in 1,4-dioxane (29 mL) under dry nitrogen. 4-Dimethylaminopyridine (71 mg, 0.58 mmol) and di-tert-butyl dicarbonate (1.9 g, 8.7 mmol) were added in single portions and the solution was heated to 95° C. The solution was stirred at 95° C. for 3 h then an additional amount of TEA (0.61 mL, 4.4 mmol) and di-tert-butyl dicarbonate (0.95 g, 4.4 mmol) were added. The solution was stirred an additional 30 min at 95° C. then cooled to room temperature, treated with brine, and extracted with EtOAc (120 ml). The extract was washed with brine (120 mL), dried over $Na_2SO_4$ (anhydrous), filtered, and concentrated in vacuo to an amber viscous oil. Purification by silica gel column (hexanes/EtOAc 9:1) and trituration with hexane (5 mL) gave the title compound I-3p as a slightly yellow solid (2.26 g, 94% yield).

$^1$H NMR (400 MHz, $CDCl_3$) δ 8.15 (s, 1H); 7.47 (s, 1H); 7.33–7.26 (m, 3H); 5.42 (s, 2H); 1.38 (s, 9H). MS ($ES^+$) Calc: 413.0, Found: 358.2 ([M-56]+1, carbamic acid fragment generated on ionization).

Preparation of Intermediate 5'-tert-Butoxycarbonylamino-6'-(3-chloro-benzyloxy)-2,3,5,6-tetrahydro-[1,2']bipyrazinyl-4-carboxylic acid tert-butyl ester (I-3g)

[5-Bromo-3-(3-chloro-benzyloxy)-pyrazin-2-yl]-carbamic acid tert-butyl ester I-3p (2.18 g, 5.3 mmol), pperazine-1-carboxylic acid tert-butyl ester (1.18 g, 6.3 mmol), sodium tert-butoxide (0.71 g, 7.4 mmol), racemic BINAP (196 mg, 315 μmol), and tris(benzylideneacetone)dipalladium (96.5 mg, 105 μmol) were placed in a vial equipped with a septum cap. The vial was evacuated and backfilled with dry nitrogen three times, and toluene (11 mL) added. The mixture was heated to 80° C. for 2 h then cooled to room temperature. Resulting suspension was transferred to a flask with $CH_2Cl_2$ and concentrated in vacuo to an amber oily solid. Purification by silica gel column (hexanes/EtOAc 7:3) gave the title compound I-3q as a yellow foam (560 mg, 25% yield).

$^1$H NMR (400 MHz, $CDCl_3$) δ 7.48 (s, 1H); 7.42 (s, 1H); 7.32–7.28 (m, 3H); 6.73 (broad s, 1H); 5.33 (s, 2H); 3.55–3.5 (m, 4H); 3.43–3.39 (m, 4H) 1.51 (s, 9H); 1,48 (s, 9H). MS ($ES^+$) Calc: 519.2, Found: 520.1 (M+1).

Preparation of 6'-(3-Chloro-benzyloxy)-3,4,5,6-tetrahydro-2H-[1,2']bipyrazinyl-5'-ylamine (3-O)

5'-tert-Butoxycarbonylamino-6'-(3-chloro-benzyloxy)-2,3,5,6-tetrahydro-[1,2']bipyrazinyl-4-carboxylic acid tert-butyl ester I-3q (50 mg, 96 μmol) was dissolved in $CH_2Cl_2$ (1 mL) and trifluoroacetic acid (1 mL) was added with stirring at room temperature. The solution was stirred at room temperature for 3 h then diluted with $CH_2Cl_2$ (20 mL). The $CH_2Cl_2$ solution was washed with saturated aqueous $NaHCO_3$ (3×50 mL) and brine (25 mL), dried over $Na_2SO_4$ (anhydrous), filtered, and concentrated in vacuo to give the title compound 3-O as a reddish-brown solid (29 mg, 95% yield).

$^1$H NMR (400 MHz, $CDCl_3$) δ 7.44 (s, 1H); 7.33–7.30 (m, 3H); 7.12 (s, 1H); 5.35 (s, 2H); 4.35 (broad s, 2H); 3.29 (dd, 4H); 3.05(dd, 4H). MS ($ES^+$) Calc: 319.1, Found: 320.4 (M+1).

Example 3-P

Preparation of the Intermediate 3'-Amino-6'bromo-2,3,5,6-tetrahydro-[1,2']bipyrazinyl-4-carboxylic acid tert-butyl ester (I-3r)

2-Amino-3,5-dibromopyrazine (1.26 g, 5.0 mmol) and piperazine-1-carboxylic acid tert-butyl ester (4.64 g, 25 mmol) were placed in a dry RBF and heated with stirring to 120° C. under dry nitrogen. Molten mixture was stirred at this temperature for 6 h and cooled to room temperature. The resulting slurry was diluted with EtOAc (20 mL) and stirred for 20 min. Amine salts were removed by filtration and washed with EtOAc (3×5 mL). Filtrate was washed with pH 4 buffer (35 mL) and brine (35 mL), dried over $Na_2SO_4$ (anhydrous), filtered, and concentrated in vacuo. The residue was purified by flash chromatography (hexanes/EtOAc 7:3) gives the title compound I-3r as an off white solid (1.64 g, 92% yield).

$^1$H NMR (400 MHz, $CDCl_3$) δ 7.81 (s, 1H); 4.54 (m, 2H); 3.75–3.38 (m, 4H); 3.37–2.95 (m, 4H); 1.47 (s, 9H). MS ($ES^+$) Calc: 357.1, Found: 358.3 (M+1).

Preparation of Intermediate 3'-Amino-6'-(3-chloro-benzyloxy)-2,3,5,6-tetrahydro-[1,2']bipyrazinyl-4-carboxylic acid tert-butyl ester (I-3s)

3'-Amino-6'-(3-chloro-benzyloxy)-2,3,5,6-tetrahydro-[1,2']bipyrazinyl-4-carboxylic acid tert-butyl ester I-3s was prepared from 3'-Amino-6'-bromo-2,3,5,6-tetrahydro-[1,2']bipyrazinyl-4-carboxylic acid tert-butyl ester I-3r (1.0 g, 2.8 mmol) and 3-chlorobenzyl alcohol (0.36 mL, 3.1 mmol) in a manner analogous to compound I-1b in example 1. The title compound I-3s was obtained as a red viscous oil (394 mg, 34% yield).

$^1$H NMR (400 MHz, $CDCl_3$) δ 7.45 (s, 1H); 7.42 (s, 1H); 7.32–7.22 (m, 3H); 5.22 (s, H); 4.40–4.00 (broad s, 1H); 3.76–3.34 (m, 4H); 3.30–2.92 (m, 4H); 1,48 (s, 9H). MS ($ES^+$) Calc: 419.2, Found: 420.4 (M+1).

Preparation of 6'-(3-Chloro-benzyloxy)-3,4,5,6-tetrahydro-2H-[1,2']bipyrazinyl-3'-ylamine (3-P)

3'-Amino-6'-(3-chloro-benzyloxy)-2,3,5,6-tetrahydro-[1,2']bipyrazinyl-4-carboxylic acid tert-butyl ester I-3s (150 mg, 357 μmol) was dissolved in 1,4-dioxane (6 mL) and an HCl solution (0.90 mL, 4 M in 1,4-dioxane, 3.6 mmol) was added with stirring at 40° C. The solution was stirred at 40° C. for 18 h and concentrated in vacuo to approximately 2 mL. The mixture was diluted with $Et_2O$. The resulting brown solid was collected by filtration and washed twice with Et$_2$O. The solid was purified by preparative HPLC to give the title compound 3-P as a tan solid (19 mg, 17% yield).

$^1$H NMR (400 MHz, CD$_3$OD) δ 8.44 (s, 1H); 7.45 (d, 1H); 7.39–7.27 (m, 3H); 5.28 (s, 2H); 3.46–3.34 (m, 8H). MS (ES$^+$) Calc: 319.1, Found: 320.6 (M+1).

Example 3-Q

Preparation of the Intermediate (2-Methyl-thiazol-4-yl)-methanol (I-3t)

Freshly distilled 2,2,6,6-tetramethylpiperidine (1.8 mL, 10.5 mmol) was dissolved in dry THF (50 mL) in a flame-dried RBF and cooled to −78° C. under dry nitrogen. A solution of n-butyllithium (4.8 mL, 2.1 M in hexanes, 10 mmol) was added slowly to the cooled solution with stirring. The resulting yellow solution was warmed to 0° C., stirred for 30 min and cooled to −78° C. A solution of 4-methylthiazole (455 μL, 5.0 mmol) in dry THF (5 mL) was added by cannula. The resulting solution was stirred for 30 min at −78° C. Dry DMF (774 μL, 10 mmol) was added with stirring over 5 min. The solution was stirred at −78° C. for 1 h then warmed to room temperature. After stirring 1 h, the solution was diluted with EtOH (20 mL) and sodium borohydride (0.57 g, 15 mmol) was added with gas evolution. The solution was stirred for 2 h then poured into aqueous saturated NH$_4$Cl (100 mL). The phases were separated and the aqueous phase was extracted with CH$_2$Cl$_2$ (3×50 mL). The combined organic extracts were washed with brine, dried over MgSO$_4$ (anhydrous), filtered, and concentrated in vacuo. The residue was purified by flash chromatography (3% MeOH in CH$_2$Cl$_2$) to give the title compound I-3t as a yellow oil (368 mg, 57% yield).

$^1$H NMR (400 MHz, CDCl$_3$) δ 7.26 (s, 1H); 4.86 (s, 2H); 4.37 (broad s, 1H); 2.38 (s, 3H). MS (EI) Calc: 129.0, Found: 129 (M+).

Preparation of Intermediate 6'-(4-Methyl-thiazol-2-ylmethoxy)-2,3,5,6-tetrahydro-[1,2']bipyrazinyl-4-carboxylic acid tert-butyl ester (I-3u)

(2-Methyl-thiazol-4-yl)-methanol I-3t (155 mg, 1.2 mmol) was dissolved in dry toluene (5 mL) under dry nitrogen and 6'-chloro-2,3,5,6-tetrahydro-[1,2']-bipyrazinyl-4-carboxylic acid tert-butyl ester (I-1a) (299 mg, 1.00 mmol), powdered KOH (191 mg, 3.4 mmol), and 18-crown-6 (13.2 mg, 50 μmol) were added with stirring. The mixture was heated at reflux with vigorous stirring. The mixture was stirred at reflux for 3 h then cooled to room temperature. The toluene was removed in vacuo. The residue was purified by preparative thin layer chromatography (10% methanol/90% CH$_2$Cl$_2$) to give the title compound I-3u as a viscous amber oil (375 mg, 96% yield).

$^1$H NMR (400 MHz, CDCl$_3$) δ 7.68 (s, 1H); 7.62 (s, 1H); 6.88 (q, 1H, J=0.83 Hz); 5.58 (s, 2H); 3.65–3.35 (m, 8H); 2.45 (d, 3H, J=0.83 Hz); 1.48 (s, 9H). MS (APCI+) Calc: 391.2, Found: 392.2 (M+1).

Preparation of 6'-(4-Methyl-thiazol-2-ylmethoxy)-3,4,5,6-tetrahydro-2H-[1,2']bipyrazinyl, (3-Q)

6'-(4-Methyl-thiazol-2-ylmethoxy)-2,3,5,6-tetrahydro-[1,2']bipyrazinyl-4-carboxylic acid tert-butyl ester (I-3u) (376 mg, 0.96 mmol) was dissolved in dry 1,4-dioxane (4 mL) and 4 M HCl in 1,4-dioxane (4 mL, 16 mmol) was added with stirring. A gummy solid immediately precipitated. Methanol (2 mL) was added to solubilize the solid. The resulting solution was stirred at room temperature for 4 h and concentrated to a gummy yellow solid. The residue was basified by addition of 1 M NaOH (15 mL) and extracted with CH$_2$Cl$_2$ (3×20 mL). The combine extracts were dried over Na$_2$SO$_4$ (anhydrous), filtered, and concentrated in vacuo to an amber oil. The oil solified on drying in vacuo to give the title compound 3-Q (274 mg, 98% yield).

$^1$H NMR (400 MHz, CDCl$_3$) δ 7.67 (s, 1H); 7.61 (s, 1H); 6.87 (q, 1H, J=0.83 Hz); 5.58 (s, 2H); 3.57–3.53 (m, 4H); 3.00–2.95 (m, 4H); 2.45 (d, 3H, J=0.83 Hz). MS (APCI+) Calc: 291.1, Found: 292.2 (M+1).

Example 3-R

Preparation of 5'-Bromo-6'-(3-chloro-benzyloxy)-3,4,5,6-tetrahydro-2H-[1,2']bipyrazinyl formate (3-R)

A solution of 5'-bromo-6'-(3-chloro-benzyloxy)-3,4,5,6-tetrahydro-2H-[1,2']bipyrazinyl-4-carboxylic acid tert-butyl ester I-3j (25 mg, 0.052 mmol) in formic acid (96%, 0.75 ml) was stirred at room temperature for 2 h, and concentrated in vacuo. The title compound 3-R was collected as a white solid (26 mg, >99%).

MS (ES$^+$) Calc: 382.0, Found: 383.3 (M+1).

Example 3-S

Preparation of 5'-Bromo-6'-(3-chloro-benzyloxy)-3,4,5,6-tetrahydro-2H-[1,2']bipyrazinyl methanesulfonate (3-S)

A solution of 5'-bromo-6'-(3-chloro-benzyloxy)-3,4,5,6-tetrahydro-2H-[1,2']bipyrazinyl-4-carboxylic acid tert-butyl ester I-3j (25 mg, 0.052 mmol) in 1,4-dioxane (0.5 ml) was treated with methanesulfonic acid (6.7 μl, 0.104 mmol) was stirred at room temperature for 16 h. The mixture was treated with ether to afford a precipitate. The supernatant was removed. The residue was treated with ether. The supernatant was again removed to provide a solid (26 mg, 87%).

MS (ES$^+$) Calc: 382.0, Found: 383.3 (M+1).

Example 4

Example 4 illustrates alternative methods for preparing compounds of the present invention wherein W is nitrogen and further illustrates compounds of the present invention where W is nitrogen not illustrated in Examples 1 and 2 above.

Example 4-A

Preparation of Intermediate (3-Fluoro-benzyl)-carbamic acid tert-butyl ester (I-4a)

A mixture of 3-fluoro-benzylamine (0.25 mL, 2.19 mmol) and Di-tert-butyl dicarbonate (0.5 mL, 2.19 mmol) in THF (5 mL) was stirred at ambient temperature for 2 h. The reaction mixture was poured into H$_2$O (15 mL) and extracted with EtOAc (2×20 mL). The organic layers were combined, washed with brine, dried (Na$_2$SO$_4$), and concentrated in vacuo to yield the title compound I-4a (493 mg).

$^1$HNMR (CDCL$_3$): δ 1.4(s, 9H), 4.3(d, 2H), 6.91–6.98 (m, 2H), 7.02–7.04 (d, 1H), 7.26–7.30 (m, 1H).

Preparation of Intermediate (6-Chloro-pyrazin-2-yl)-(3-fluoro-benzyl)-carbamic acid tert-butyl ester (I-4b)

A solution of (3-fluoro-benzyl)-carbamic acid tert-butyl ester I-4a (1.21 g, 5.37 mmol) in DMF (50 mL) was treated with 60% NaH in mineral oil (430 mg, 10.7 mmol). The resulting mixture was stirred at ambient temperature until the gas evolution ceased. The solution was treated with 2,6-dichloro-pyrazine (800 mg, 5.37 mmol) and the reaction mixture was heated to 80° C. under $N_2$ and stirred for 5 h. The reaction was cooled and concentrated in vacuo to approximately ⅓ volume. The reaction mixture was poured into $H_2O$ (50 mL) and extracted with Ethyl Acetate (1×200 mL). The organic layer was washed with $H_2O$ (4×50 mL), brine, dried ($Na_2SO_4$), and concentrated to dryness. The crude product was purified by chromatography (EtOAc/Hex 5:95) to afford the title compound I-4b (1.14 g) as a colorless oil.

MS (ES$^+$) Calc.: 337, Found: 338.1 (M+1). $^1$HNMR (MeOD): δ 1.4(s, 9H), 5.1(s, 2H), 7.0(m, 3H), 7.3(m, 1H), 8.3(s, 1H), 9.1(s, 1H).

Preparation of Intermediate (3-Fluoro-benzyl)-(3,4,5,6-tetrahydro-2H-[1,2']bipyrazinyl-6'-yl)-carbamic acid tert-butyl ester (I-4c)

A solution of (6-chloro-pyrazin-2-yl)-(3-fluoro-benzyl)-carbamic acid tert-butyl ester (1.14 g, 3.39 mmol) and piperazine (1.75 g, 20 mmol) in EtOH (34 mL) was stirred at reflux for 19 h. The reaction mixture was cooled and concentrated in vacuo. The residue was dissolved in Ethyl Acetate and washed with $H_2O$ (4×50 mL), brine, dried ($Na_2SO_4$), and concentrated to dryness. The crude product was chromatographed on Silica Gel (90 g) using 5% MeOH in $CH_2Cl_2$ as the eluant to give the title compound I-4c (1.09 g) as a pale yellow oil.

MS (ES$^+$) Calc.: 387, Found: 388.5 (M+1). $^1$HNMR (MeOD): δ 1.4(s, 9H), 2.8(m, 4H), 3.4(m, 4H), 5.1(s, 2H), 7.0(m, 3H), 7.3(m, 1H), 7.8(s, 1H), 8.3(s, 1H).

Preparation of (3-Fluoro-benzyl)-(3,4,5,6-tetrahydro-2H-[1,2']bipyrazinyl-6'-yl)-amine (4-A)

To a solution of (3-fluoro-benzyl)-(3,4,5,6-tetrahydro-2H-[1,2']bipyrazinyl-6'-yl)-carbamic acid tert-butyl ester I-4c (30 mg, 0.08 mmol) in $CH_2Cl_2$ (1 mL) was added with trifluoroacetic Acid (0.5 mL) and the resulting mixture was stirred at ambient temperature for 19 h. The reaction mixture was poured into 1N NaOH (10 mL) and extracted with ethyl acetate (1×40 mL). The organic layer was washed with brine, dried ($Na_2SO_4$), and concentrated to give the title compound 4-A (19.3 mg).

MS (ES$^+$) Calc.: 287, Found: 288.4 (M+1). $^1$HNMR (CDCL$_3$): δ 2.9(m, 4H), 3.5(m, 4H), 4.5(m, 2H), 4.8(bm, 1H), 6.9(m, 1H), 7.0(m, 1H), 7.3(m, 3H).

The compounds listed in Table 4 were prepared using the general procedures described in Example 4-A above with the appropriate starting materials.

TABLE 4

| Ex. No. | Compound Name | Analytical Data |
|---|---|---|
| 4-B | (2-Fluoro-benzyl)-(3,4,5,6-tetrahydro-2H-[1,2']bipyrazinyl-6'-yl)-amine hydrochloride salt | MS (ES$^+$) Calc.: 287, Found: 288.4 (M + 1). $^1$HNMR (MeOD): δ 3.3(m, 4H), 3.9(m, 4H), 4.7(bs, 2H), 7.1(m, 2H), 7.3(m, 2H), 7.4(m, 2H). |
| 4-C | (4-Chloro-benzyl)-(3,4,5,6-tetrahydro-2H-[1,2']bipyrazinyl-6'-yl)-amine hydrochloride salt | MS (ES$^+$) Calc.: 303, Found: 304.4 (M + 1). $^1$HNMR (MeOD): δ 3.3(m, 4H), 3.9(m, 4H), 4.6(m, 2H), 7.3(m, 5H), 7.4(m, 1H). |
| 4-D | (4-Fluoro-benzyl)-(3,4,5,6-tetrahydro-2H-[1,2']bipyrazinyl-6'-yl)-amine hydrochloride salt | MS (ES$^+$) Calc.: 287, Found: 288.4 (M + 1). $^1$HNMR (MeOD): δ 3.3(m, 4H), 3.9(m, 4H), 4.6(m, 2H), 7.1(m, 2H), 7.3(s, 1H), 7.4(m, 3H). |
| 4-E | (2,5-Dichloro-benzyl)-(3,4,5,6-tetrahydro-2H-[1,2']bipyrazinyl-6'-yl)-amine | MS (ES$^+$) Calc.: 337, Found: 338.2 (M + 1). $^1$HNMR (MeOD): δ 3.0(m, 4H), 3.6(m, 4H), 4.6(m, 2H), 7.3(m, 5H). |
| 4-F | (3,5-Difluoro-benzyl)-(3,4,5,6-tetrahydro-2H-[1,2']bipyrazinyl-6'-yl)-amine hydrochloride salt | MS (ES$^+$) Calc.: 305, Found: 306.3 (M + 1). $^1$HNMR (MeOD): δ 3.3(m, 4H), 3.9(m, 4H), 4.6(m, 2H), 6.8(m, 1H), 7.0(m, 2H), 7.3(s, 1H), 7.5(s, 1H). |
| 4-G | (3,5-Dichloro-benzyl)-(3,4,5,6-tetrahydro-2H-[1,2']bipyrazinyl-6'-yl)-amine | MS (ES$^+$) Calc.: 337, Found: 338.3 (M + 1). $^1$HNMR (CDCl$_3$): δ 2.9(m, 4H), 3.4(m, 4H), 4.4(m, 2H), 4.9(m, 1H), 7.2(m, 4H), 7.4(m, 1H). |
| 4-H | (2,3-Difluoro-benzyl)-(3,4,5,6-tetrahydro-2H-[1,2']bipyrazinyl-6'-yl)-amine | MS (ES$^+$) Calc.: 305, Found: 306.3 (M + 1). $^1$HNMR (CDCl$_3$): δ 2.9(m, 4H), 3.5(m, 4H), 4.6(m, 2 4.8(m, 1H), 7.1(m, 3H), 7.2(m, 1H), 7.4(s, 1H). |
| 4-I | (2,3-Dichloro-benzyl)-(3,4,5,6-tetrahydro-2H-[1,2']bipyrazinyl-6'-yl)-amine | MS (ES$^+$) Calc.: 337, Found: 338.2 (M + 1). $^1$HNMR (CDCl$_3$): δ 2.9(m, 4H), 3.4(m, 4H), 4.6(m, 2 4.9(m, 1H), 7.1(m, 1H), 7.2(m, 2H), 7.4(m, 2H). |
| 4-J | (2,6-Difluoro-benzyl)-(3,4,5,6-tetrahydro-2H-[1,2']bipyrazinyl-6'-yl)-amine | MS (ES$^+$) Calc.: 305, Found: 306.3 (M + 1). $^1$HNMR (CDCl$_3$): δ 2.9(m, 4H), 3.5(m, 4H), 4.6(m, 2 4.8(m, 1H), 6.9(m, 2H), 7.2(m, 2H), 7.4(s, 1H). |
| 4-K | (2-Chloro-6-fluoro-benzyl)-(3,4,5,6-tetrahydro-2H-[1,2']bipyrazinyl-6'-yl)-amine | MS (ES$^+$) Calc.: 321, Found: 322.3 (M + 1). $^1$HNMR (CDCl$_3$): δ 2.9(m, 4H), 3.5(m, 4H), 4.7(m, 2 4.8(m, 1H), 7.0(m, 1H), 7.2(m, 2H), 7.3(s, 1H), 7.4(s, 1H) |

Example 4-L

Preparation of (3-Fluoro-benzyl)-(3,4,5,6-tetrahydro-2H-[1,2']bipyrazinyl-6'-yl)-amine hydrochloride salt (4-L)

To a solution of (3-fluoro-benzyl)-(3,4,5,6-tetrahydro-2H-[1,2']bipyrazinyl-6'-yl)-carbamic acid tert-butyl ester I-4c (1.09 g, 2.82 mmol) in Methanol (6 mL) was treated with 1.0 M HCl/ether (28.2 mL, 28.2 mmol). The reaction mixture was stirred at ambient temperature for 19 h and concentrated in vacuo. The residue was repulped overnight in a mixture of Methanol (5 mL) and Ether (40 mL). The resulting tan solid was filtered and dried under high vacuum to afford the title compound 4-L (745 mg).

MS (ES$^+$) Calc.: 287, Found: 288.4 (M+1). $^1$HNMR (MeOD): δ 3.3(m, 4H), 3.9(m, 4H), 4.6(s, 2H), 7.0(m, 1H), 7.1(m, 11H), 7.2(m, 1H), 7.3(m, 2H), 7.5(s, 1H).

Example 4-M

Preparation of Intermediate (3-Chloro-benzyl)-carbamic acid tert-butyl ester (I-4d)

A solution of 3-chloro-benzylamine (0.25 mL, 2.05 mmol) and di-tert-butyl dicarbonate (0.47 mL, 2.1 mmol) in THF (10 mL) was stirred at ambient temperature overnight. The reaction mixture was concentrated in vacuo to a residue and chromatographed on Silica Gel (40 g) using 10% ethyl ccetate/hexanes as the eluant to the title compound I-4d (458 mg).

$^1$HNMR (CDCl$_3$): δ 1.4(s, 9H), 4.3(bd, 2H), 4.8(bm, 1H), 7.1(m, 1H), 7.2(bm, 3H).

Preparation of Intermediate (3-Chloro-benzyl)-(6-chloro-pyrazin-2-yl)-carbamic acid tert-butyl ester (I-4e)

A solution of (3-chloro-benzyl)-carbamic acid tert-butyl ester (458 mg, 1.9 mmol) in DMF (20 mL) was treated with 60% NaH in mineral oil (152 mg, 3.79 mmol). The resulting mixture was stirred at room, temperature until the gas evolution ceased and 2,6-dichloro-pyrazine (282 mg, 1.89 mmol) was added. The reaction mixture was stirred at 80° C. until the LC/MS indicated the reaction was complete. The reaction mixture was cooled and poured into Ethyl Acetate and washed with H$_2$O and brine. The organic layers were combined, dried (Na$_2$SO$_4$), and concentrated to yield the title compound I-4e (199 mg).

MS (ES$^+$) Calc.: 353, Found: 354.2 (M+1). $^1$HNMR (CDCL$_3$): δ 1.5(s, 9H), 5.1(s, 2H), 7.2(m, 3H), 7.3(m, 1H), 8.2(s, 1H), 9.1(s, 1H).

Preparation of Intermediate (3-Chloro-benzyl)-(3,4,5,6-tetrahydro-2H-[1,2']bipyrazinyl-6'-yl)-carbamic acid tert-butyl ester (I-4f)

A solution of (3-Chloro-benzyl)-(6-chloro-pyrazin-2-yl)-carbamic acid tert-butyl ester I-4e (68 mg, 0.19 mmol) and piperazine (99 mg, 1.15 mmol) in Ethanol (2 mL) were refluxed overnight. The reaction mixture was cooled and poured into 0.1M NaOH and extracted into ethyl acetate. The organic layer was washed with H$_2$O, brine, dried (Na$_2$SO$_4$), and concentrated to give the title compound I-4f (38 mg).

MS (ES$^+$) Calc.: 403, Found: 404.3 (M+1). $^1$HNMR (CDCL$_3$): δ 1.4(s, 9H), 2.9(m, 4H), 3.4(m, 4H), 5.0(s, 2H), 7.1(m, 3H), 7.2(m, 1H), 7.8(s, 1H), 8.3(s, 1H).

Preparation of (3-Chloro-benzyl)-(3,4,5,6-tetrahydro-2H-[1,2']bipyrazinyl-6'-yl)-amine (4-M)

(3-Chloro-benzyl)-(3,4,5,6-tetrahydro-2H-[1,2']bipyrazinyl-6'-yl)-carbamic acid tert-butyl ester I-4f (37.5 mg, 0.09 mmol) was treated with 4.0M HCl/Dioxane (2 mL, 8 mmol). Methanol was added until a clear solution is formed and the mixture was stirred overnight at ambient temperature. The reaction mixture was poured into 1N HCl and extracted with ethyl acetate. The aqueous phase was brought to pH 14 with 5N KOH and extracted with Ethyl Acetate. The organic layers were washed with brine, dried (Na$_2$SO$_4$), and concentrated to afford the title compound 4-M (23.3 mg).

MS (ES$^+$) Calc.: 303, Found: 304.3 (M+1). $^1$HNMR (MeOD): δ 2.9(m, 4H), 3.5(m, 4H), 4.5(bs, 2H), 7.3(bm, 6H).

Example 4-N

Preparation of (3-Chloro-benzyl)-(3,4,5,6-tetrahydro-2H-[1,2']bipyrazinyl-6'-yl)-amine fumarate salt (4-N)

A solution of (3-chloro-benzyl)-(3,4,5,6-tetrahydro-2H-[1,2']bipyrazinyl-6'-yl)-amine 4-M (1.14 g, 3.74 mmol) in a mixture of methanol (15 mL) and isopropyl Ether (90 mL) was treated with a methanolic solution of fumaric acid (434 mg in 7.5 mL Methanol, 3.74 mmol). The resulting mixture was stirred at room temperature for 1 h. Additional isopropyl Ether (120 mL) was then added to the reaction mixture and stirring continued for 10 minutes. The resulting solids were filtered from the solution and dried under high vacuum to obtain the title compound 4-N (1.25 g).

MS (ES$^+$) Calc.: 303, Found: 304.2 (M+1). $^1$HNMR (DMSO): δ 2.8 (m, 4H), 3.4 (m, 4H), 4.4 (m, 2H), 7.3 (bm, 6H).

Example 4-O

Preparation of (2-Chloro-benzyl)-(3,4,5,6-tetrahydro-2H-[1,2']bipyrazinyl-6'-yl)-amine hydrochloride salt (4-O)

The general procedure described in Example 4-A, was followed using 2-chloro-benzylamine as the starting amine in the preparation of the first intermediate to obtain the BOC-protected compound. The protecting group was removed by dissolving (2-chloro-benzyl)-(3,4,5,6-tetrahydro-2H-[1,2']bipyrazinyl-6'-yl)-carbamic acid tert-butyl ester (102 mg, 0.25 mM) in methanol (1 mL) and treating it with 1.0M HCl/ether (2.5 mL, 2.53 mmol). The resulting mixture was stirred and additional Methanol was added until the solution was clear. The reaction mixture was then stirred overnight at ambient temperature. Ether was added to the reaction mixture until it turned cloudy and then stirred for an additional 15 minutes. The solids were filtered from the mixture, washed with Ether, and air-dried to afford the title compound 4-O (41.8 mg).

MS (ES$^+$) Calc.: 303, Found: 304.4 (M+1). $^1$HNMR (MeOD): δ 3.3(m, 4H), 4.7(bs, 2H), 7.3(m, 3H), 7.4(m, 2H), 7.5(s, 1H).

Example 4-P

Preparation of (2,5-Difluoro-benzyl)-(3,4,5,6-tetrahydro-2H-[1,2']bipyrazinyl-6'-yl)-amine hydrochloride salt (4-P):

The general procedure described in Example 4-A was followed using 2,5-difluoro-benzylamine as the amine in the preparation of the first intermediate and DMAP (1 equiv.) to give the BOC-protected compound. The protecting group was removed by dissolving (2,5-difluoro-benzyl)-(3,4,5,6-tetrahydro-2H-[1,2']bipyrazinyl-6'-yl)-carbamic acid tert-butyl ester (99.6 mg, 0.24 mmol) in methanol (1 mL) and treating it with 1.0M HCl/Ether (3.68 mL, 3.68 mmol) and stirring the reaction mixture overnight at ambient temperature. Additional 1.0M HCl/ether (2 mL) was added to the reaction mixture and stirring continued overnight at room temperature. The reaction was still not complete, therefore conc. HCl (2 drops) was added and the resulting mixture stirred at ambient temperature overnight. Diethyl ether (20 mL) was added to the reaction mixture and stirring continued for 1 h. The solids were filtered from the reaction mixture, washed with Ether, and dried under high vacuum to give the title compound 4-P (64 mg).

MS (ES$^+$) Calc.: 305, Found: 306.3 (M+1). $^1$HNMR (MeOD): δ 3.3(m, 4H), 3.9(m, 4H), 4.6(m, 2H), 7.0(m, 1H), 7.1(m, 2H), 7.3(s, 1H), 7.5(s, 1H).

Example 4-Q

Preparation of Intermediate 6'-[Methyl-(6-methyl-pyridin-2-ylmethyl)-amino]-2,3,5,6-tetrahydro-[1,2']bipyrazinyl-4-carboxylic acid tert-butyl ester (I-4g)

A mixture of 6'-chloro-2,3,5,6-tetrahydro-[1,2']bipyrazinyl-4-carboxylic acid tert-butyl ester I-1a (50 mg, 0.17 mmol), methyl-(6-methyl-pyridin-2-ylmethyl)-amine (29.6 mg, 0.22 mmol), sodium tert-butoxide (45 mg, 0.46 mmol), BINAP (8.4 mg, 0.014 mmol), tris(dibenzylideneacetone)dipalladium(0) (6.2 mg, 0.006 mmol) in toluene (2 mL) was stirred at reflux for 2 h. The reaction mixture was cooled, diluted with ethyl acetate, and filtered through celite. The filtrate was concentrated in vacuo and the residue was purified via preparative TLC (5% methanol in methylene chloride) to yield the title compound I-4g (14.2 mg).

MS (ES$^+$) Calc.: 398, Found: 399.4 (M+1). $^1$HNMR (CDCl$_3$): δ 1.5(s, 9H), 2.6(m, 3H), 3.2(m, 3H), 3.5(m, 8H), 4.9(m, 2H), 6.9(m, 1H), 7.1(m, 1H), 7.4(m, 2H), 7.5(m, 1H).

Preparation of Methyl-(6-methyl-pyridin-2-ylmethyl)-(3,4,5,6-tetrahydro-2H-[1,2']bipyrazinyl-6'-yl)-amine (4-Q)

6'-[Methyl-(6-methyl-pyridin-2-ylmethyl)-amino]-2,3,5,6-tetrahydro-[1,2']-bipyrazinyl-4-carboxylic acid tert-butyl ester I-4g was deprotected with TFA as the procedure described in Example 4-A to afford the title compound 4-Q.

MS (ES$^+$) Calc.: 298, Found: 299.4 (M+1). $^1$HNMR (CDCl$_3$): δ 2.5(s, 3H), 2.9(m, 4H), 3.1(s, 3H), 3.4(m, 4H), 4.8(s, 2H), 6.9(m, 1H), 7.0(m, 1H), 7.4(m, 3H).

Example 4-R

Preparation of Intermediate 6-Methyl-pyridine-2-carbonitrile (I-4h)

2-Methyl-pyridine 1-oxide (10.9 g, 100 mmol) was dissolved into methylene chloride (100 mL) and dried over MgSO$_4$. The solution was filtered and the filtrate was added to trimethylsilyl cyanide (16.7 mL, 125 mmol) at ambient temperature. To which was added dropwise a solution of dimethylcarbamyl chloride (11.5 mL, 125 mmol) in methylene chloride (25 mL). The resulting mixture was stirred at ambient temperature for 24 h. A solution of 10% K$_2$CO$_3$ was added slowly to the reaction mixture and stirring was continued for 10 minutes after the addition was complete. The layers were separated and the aqueous layer was extracted with methylene chloride (2×50 mL). The combined organic extracts were dried (Na$_2$SO$_4$), and concentrated to dryness under high vacuum to yield the title compound I-4h (6.64 g).

$^1$HNMR (CDCl$_3$): δ 2.6(s, 3H), 7.4(m, 1H), 7.5(m, 1H), 7.7(m, 1H).

Preparation of Intermediate C-(6-Methyl-pyridin-2-yl)-methylamine (I-4i)

To a cooled solution of 1.0 M LiAlH$_4$ in THF (35.6 mL, 35.6 mmol) at 0° C. was added dropwise a solution of 6-methyl-pyridine-2-carbonitrile I-4h (2.0 g, 16.9 mmol) in THF (34 mL). The reaction mixture was stirred at 0° C. for 5 minutes after the addition was complete and then quenched with the addition of 1N NaOH (20 mL). The resulting reaction mixture was stirred for 1 h and filtered through celite washing well with ether. The filtrate was diluted with 1N NaOH (20 mL) and the organic layer separated. The organic layer was then washed with brine, dried (Na$_2$SO$_4$), and concentrated in vacuo to give the desired product I-4i (1.02 g).

$^1$HNMR (CDCl$_3$):δ 2.5(s, 3H), 3.9(s, 2H), 7.1(m, 2H), 7.5(m, 1H).

Preparation of Intermediate (6-Methyl-pyridin-2-ylmethyl)-carbamic acid tert-butyl ester (I-4j)

The general procedure in Example 4-A was followed to obtain the crude product. The compound was purified on Silica Gel (40 g) using 20% ethyl acetate/hexanes as the eluant to yield the title compound I-4j.

MS (ES$^+$) Calc.: 222, Found: 223.3 (M+1). $^1$HNMR (CDCl$_3$): δ 1.4(s, 9H), 2.5(s, 3H), 4.4(m, 2H), 7.0(m, 2H), 7.5(m, 1H).

Preparation of Intermediate (6-Chloro-pyrazin-2-yl)-(6-methyl-pyridin-2-ylmethyl)-carbamic acid tert-butyl ester (I-4k)

The general procedure in Example 4-A was followed to give the crude product. The crude material was purified on Silica Gel (40 g) using 15% ethyl acetate/hexanes as the eluant to afford the title compound I-4k.

MS (ES$^+$) Calc.: 334, Found: 335.3 (M+1). $^1$HNMR (CDCl$_3$): δ 1.4(s, 9H), 2.5(s, 3H), 5.2(s, 2H), 6.9(m, 1H), 7.0(m, 1H), 7.5(m, 1H), 8.2(s, 1H), 9.2(s, 1H).

Preparation of Intermediate (6-Methyl-pyridin-2-ylmethyl)-(3,4,5,6-tetrahydro-2H-[1,2']bipyrazinyl-6'-yl)-carbamic acid tert-butyl ester (I-4l)

The general procedure in Example 4-A was followed to yield the crude product. The crude material was purified via preparative TLC using 10% methanol/methylene chloride with 1% NH$_4$OH as the eluant to give the desired compound I-4l.

MS (ES$^+$) Calc.: 384, Found: 385.4 (M+1). $^1$HNMR (CDCl$_3$): δ 1.4(s, 9H), 2.5(s, 3H), 2.8(m, 4H), 3.3(m, 4H), 5.1(s, 2H), 6.9(m, 2H), 7.5(m, 1H), 7.7(s, 1H), 8.5(s, 1H).

Preparation of Intermediate (6-Methyl-pyridin-2-ylmethyl)-(3,4,5,6-tetrahydro-2H-[1,2']bipyrazinyl-6'-yl)-amine (I-4m)

A solution of (6-methyl-pyridin-2-yl methyl)-(3,4,5,6-tetrahydro-2H-[1,2']-bipyrazinyl-6'-yl)-carbamic acid tert-butyl ester I-4l (196.9 mg, 0.51 mM) in methylene chloride (2 mL) was treated with trifluoroacetic Acid (0.39 mL, 5.12 mmol). The resulting mixture was stirred at ambient temperature overnight. The reaction mixture was quenched with saturated NaHCO$_3$ solution and the pH of the aqueous layer brought to approximately 10 using 1N NaOH. The reaction mixture was diluted with methylene chloride and separated. The aqueous layer was extracted with methylene chloride and the organic layers were combined, dried (Na$_2$SO$_4$), and concentrated to dryness to afford the desired product I-4m.

MS (ES$^+$) Calc.: 284, Found: 285.3.

Preparation of (6-Methyl-pyridin-2-ylmethyl)-(3,4,5,6-tetrahydro-2H-[1,2']bipyrazinyl-6'-yl)-amine fumarate salt (4-R)

The general procedure in Example 4-N was followed using (6-Methyl-pyridin-2-ylmethyl)-(3,4,5,6-tetrahydro-2H-[1,2']bipyrazinyl-6'-yl)-amine I-4m as the starting material to yield the title compound.

MS (ES$^+$) Calc.: 284, Found: 285.3 (M+1). $^1$HNMR (MeOD): δ 2.5(s, 3H), 3.1(m, 4H), 3.6(m, 4H), 4.6(s, 2H), 6.7(m, 2H), 7.2(m, 2H), 7.3(m, 2H), 7.6(m, 1H).

Example 4-S

Preparation of Intermediate 3-[(6-Chloro-pyrazin-2-ylamino)-methyl]-benzonitrile (I-4n):

A mixture of 2,6-dichloropyrazine (75 mg, 0.503 mmol), 3-aminomethyl-benzonitrile (73 mg, 0.553 mmol), sodium t-butoxide (58 mg, 0.604 mmol), BINAP (12.5 mg, 0.020 mmol), and Pd$_2$(dba)$_3$ (9.2 mg, 0.010 mmol) in toluene (2 mL) was heated at reflux under nitrogen for 10 h. The solution was cooled to room temperature and filtered through a celite pad. The celite pad was washed with ethyl acetate several times. The combined filtrate was concentrated in vacuo to give the crude title compound. The product was purified by chromatography (silica, 5% MeOH/dichlormethane) to give 37.6 mg 3-[(6-chloro-pyrazin-2-ylamino)-methyl]-benzonitrile I-4n.

Preparation of 3-[(3,4,5,6-Tetrahydro-2H-[1,2'] bipyrazinyl-6'-ylamino)-methyl]-benzonitrile (4-S)

A mixture of 3-[(6-chloro-pyrazin-2-ylamino)-methyl]-benzonitrile I-4n (37.6 mg, 0.154 mmol), piperazine (16 mg, 0.185 mmol), sodium t-butoxide (18 mg, 0.185 mmol), BINAP (3.8 mg, 0.006 mmol), and $Pd_2(dba)_3$ (2.8 mg, 0.003 mmol) in toluene (2 mL) was heated at reflux under nitrogen for 10 h. The solution was cooled to room temperature and filtered through a celite pad. The celite pad was washed with ethyl acetate several times. The combined filtrate was concentrated in vacuo to give the crude title compound 4-S. The product was purified by chromatography (silica, 10% MeOH/dichlormethane with 1% $NH_4OH$) to give the title compound 4-S (10 mg).

$^1$H NMR (400 MHz, $CD_3OD$) δ 7.67 (s, 1H); 7.63 (d, 1H); 7.55 (d, 1H); 7.55 (d, 1H); 7.45 (t, 1H); 7.22 (s, 1H); 7.18 (s, 1H); 4.52 (s, 2H); 3.40 (t, 4H); 2.80 (t, 4H). MS ($ES^+$) Calc: 294.1, Found: 295.3 (M+1).

Example 4-T

Preparation of Intermediate Indan-1-yl-(3,4,5,6-tetrahydro-2H-[1,2']bipyrazinyl-6'-yl)-amine-4-carboxylic acid tert-butyl ester (I-4o)

A mixture of 6'-chloro-2,3,5,6-tertrahydro-[1,2'] bipyrazinyl-4-carboxylic acid tert-butyl ester (I-1a) (100 mg, 0.33 mmol), (S)-1-aminoindane (49 mg, 0.37 mmol), sodium tert-butoxide (57 mg, 0.46 mmol), $Pd_2(dba)_3$ (21 mg, 0.023 mmol) and Amphos (29 mg, 0.073 mmol) in toluene (anhydrous, 2 ml) under a nitrogen atmosphere was heated at reflux for 16 h. The reaction mixture was cooled to room temperature and filtered through a pad of silica gel, eluting with EtOAc-hexane (9:1). The filtrate was concentrated in vacuo. The residue was purified by preparative TLC (EtOAc-hexane 6:4) to provide 26 mg of the title compound I-4o (20%).

MS ($ES^+$) Calc: 395.2, Found: 396.2 (M+1).

Preparation of Indan-1-yl-(3,4,5,6-tetrahydro-2H-[1, 2']bipyrazinyl-6'-yl)-amine hydrochloride (4-T)

A solution of indan-1-yl-(3,4,5,6-tetrahydro-2H-[1,2'] bipyrazinyl-6'-yl)-amine-4-carboxylic acid tert-butyl ester I-4o (26 mg, 0.066 mmol) in HCl in 1,4-dioxane (4 M, 1.0 ml, 4 mmol) at 23° C. was stirred at room temperature for 2 h. The mixture was treated with ether, and a precipitate appeared. The solid was collected by filtration. The solid was dissolved in methanol and concentrated in vacuo to afford the title compound 4-T (10 mg, 41%). MS ($ES^+$) Calc: 295.2, Found: 296.2 (M+1).

Example 5

Example 5 illustrates a representative compound of the present invention where W is an acetylamino.

Preparation of Intermediate N-(6-Chloro-pyrazin-2-yl)-acetamide (I-5a)

A solution of 6-chloro-pyrazin-2-ylamine (50 mg, 0.38 mmol) in acetic acid (1.9 mL) was treated with acetic anhydride (0.04 mL, 0.42 mmol). The mixture was heated to reflux for 1 h, cooled to room temperature, then poured into saturated $NaHCO_3$ (30 mL) and extracted with ethyl acetate (2×30 mL). The organic layers were combined, washed with brine, dried ($Na_2SO_4$), filtered, and concentrated to dryness to give the title compound I-5a (58.6 mg).

MS ($ES^+$) Calc.: 171.1, Found: 172.0 (M+1). $^1$HNMR ($CDCl_3$): δ 9.42 (s, 1H), 8.34 (s, 1H), 7.90 (br s, 1H) 2.24(s, 3H).

Preparation of Intermediate 6'-Acetylamino-2,3,5,6-tetrahydro-[1,2']bipyrazinyl-4-carboxylic acid tert-butyl ester (I-5b)

A mixture of N-(6-chloro-pyrazin-2-yl)-acetamide I-5a (58.6 mg, 0.34 mmol) and piperazine-1-carboxylic acid tert-butyl ester (636 mg, 3.42 mmol) in ethanol (2 mL) was stirred at reflux for 24 h. The reaction mixture was diluted with ethyl acetate (40 mL) and washed with 0.1M HCl (3×35 mL), brine, dried ($Na_2SO_4$), filtered, and evaporated to dryness. The crude residue was purified by preparative TLC using ethyl acetate as the eluant to afford the title compound I-5b (36.9 mg).

MS ($ES^+$) Calc.: 321.1, Found: 322.3 (M+1). $^1$HNMR ($CDCl_3$): δ 8.75 (br s, 1H), 7.86 (s, 1H), 7.70 (br s, 1H) 2.20(s, 3H), 1.46 (s, 9H).

Preparation of Intermediate 6'-[Acetyl-(3-chloro-benzyl)-amino]-2,3,5,6-tetrahydro-[1,2']bipyrazinyl-4-carboxylic acid tert-butyl ester (I-5c)

To a solution of 6'-acetylamino-2,3,5,6-tetrahydro-[1,2'] bipyrazinyl-4-carboxylic acid tert-butyl ester I-5b (36.9 mg, 0.11 mmol) and 1-bromomethyl-3-chloro-benzene (15.8 μL, 0.12 mmol) in DMF (1.1 mL) at room temperature was added 60% NaH in mineral oil (5 mg, 0.13 mmol). After stirring at room temperature for 4 h, the reaction mixture was poured into $H_2O$ (10 mL) and extracted with ethyl acetate (50 mL). The organic layer was washed with $H_2O$ (3×10 mL), brine, dried ($Na_2SO_4$), filtered, and evaporated to dryness. The crude material was purified by preparative TLC using 50% ethyl acetate/ether with 1% $NH_4OH$ to afford the title compound I-5c (27.1 mg).

MS ($ES^+$) Calc.: 445.2, Found: 446.2 (M+1). $^1$HNMR ($CD_3OD$): δ 8.07 (s, 1H), 7.85 (br s, 1H), 7.33–7.16 (m, 4H) 5.01 (s, 2H), 3.57–3.42 (m, 8H), 2.12(s, 3H), 1.46 (s, 9H).

Preparation of N-(3-Chloro-benzyl)-N-(3,4,5,6-tetrahydro-2H-[1,2']bipyrazinyl-6'-yl)-acetamide (5-A)

To a solution of 6'-[acetyl-(3-chloro-benzyl)-amino]-2,3, 5,6-tetrahydro-[1,2']bipyrazinyl-4-carboxylic acid tert-butyl ester I-5c (27.1 mg, 0.06 mmol) in methylene chloride (1 mL) was added trifluoroacetic Acid (1 mL). The reaction mixture was stirred at room temperature until the reaction was completed. The reaction mixture was poured into saturated $NaHCO_3$ (20 mL) and extracted with methylene chloride (2×15 mL). The organic layers were combined, dried ($Na_2SO_4$), filtered, and concentrated to dryness to yield the title compound 5-A (26.2 mg).

MS ($ES^+$) Calc.: 345.1, Found: 346.2 (M+1). $^1$HNMR ($CDCl_3$): δ 7.95 (s, 1H), 7.74 (br s, 1H), 7.32–7.11 (m, 4H), 4.97 (s, 2H), 3.57–3.52(m, 4H), 3.00–2.96 (m, 4H), 2.26 (br s, 1H), 2.13(s, 3H).

Example 6

Example 6 illustrates the synthesis of NEPi Compound—(S)-2-[(1-{[3-(4-chlorophenyl)propyl]carbamoyl}cyclopentyl)methyl]-4-methoxy-butanoic acid referred to herein below for use in combination with the compounds of the present invention for treating female sexual dysfunction.

Preparation of Intermediate 1-[2-(tert-Butoxycarbonyl-4-methoxybutyl]-cyclopentanecarboxylic acid (I-6a)

A solution of tert-butyl 3-(1-carboxycyclopentyl) propanoate (12 g, 49.5 mmol) (see EP274234B1, Example 35) in dry tetrahydrofuran (100 ml) was added to a stirred solution of lithium diisopropylamide (130 ml) in a mixture of hexane (52 ml) and tetrahydrofuran (200 ml) at −78° C. under nitrogen. After 1 hour a solution of 2-bromoethyl methyl ether in tetrahydrofuran (100 ml) was added maintaining the temperature at −78° C. The reaction mixture was allowed to warm up to room temperature overnight. The mixture was quenched with water (100 ml) and acidified to pH 1 with 2M hydrochloric acid, and extracted with ethyl acetate (2×150 ml). The combined organic extracts were dried over magnesium sulfate and concentrated in vacuo to give the crude acid which was chromatographed on silica. Elution with increasing proportions of methanol in dichloromethane (neat dichloromethane to 1:50) gave an oil (7.7 g, 25.6 mmol, 52%); Rf 0.3 methanol, dichloromethane 1:20;

$^1$H NMR (CDCl$_3$ 400 MHz) δ: 1.4 (s, 9H), 1.4–1.7 (m, 7H), 1.75–1.95 (m, 2H), 2.0–2.15 (m, 3H), 2.3–2.4 (m, 1H), 3.3 (s, 3H), 3.3–3.4 (m, 2H); LRMS: m/z 299 (M−H$^+$).

Preparation of Intermediate 1-[(2S)-2-(tert-Butoxycarbonyl)-4-methoxybutyl]-cyclopentanecarboxylic acid (I-6b)

Intermediate I-6a and (+)-pseudoephedrine were recrystallised nine times from hexane to give a white crystaline solid. The salt was dissolved in ethyl acetate washed with 0.5M hydrochloric acid dried over magnesium sulphate and concentrated in vacuo the (S)-acid was obtained in 31% yield as a pale yellow oil in >90% ee (enantiomeric excess) by NMR analysis of the δ 3.3 peak of the (+)-pseudoephedrine salt;

$^1$H NMR (CDCl$_3$ 400 MHz) δ: 1.4 (s, 9H), 1.4–1.7 (m, 7H), 1.75–1.9 (m, 2H), 2.0–2.15 (m, 3H), 2.35–2.45 (m, 1H), 3.3 (s, 3H), 3.3–3.4 (m, 2H); [α]$_D$ −5.2 (EtOH, c 1.2).

Preparation of Intermediate tert-butyl (2S)-2-{[1-({[3-(4-chlorophenyl-propyl]amino}carbonyl) cyclopentyl]methyl}-4-methoxybutanoate (I-6c)

To a solution of 1,1'-carbonyl diimidazole (73.9 g, 0.45 mol) in azeotropically dried isopropyl acetate (339 ml) was added the isopropyl acetate solution of the Intermediate I-6b with stirring at 60° C. under an atmosphere of N$_2$ over a period of 1.5 hours. The transfer lines were then washed with dry isopropyl acetate (50 ml). The resultant solution was then stirred at 60° C. for a further 4.5 hours and then the reaction mixture was allowed to cool to room temperature and stirred for 15 hours. To the resultant solution was then added triethylamine (46.1 g, 0.46 mol), followed by 3-(4-chlorophenyl)-propylamine hydrochloride (J. Med. Chem., 1996, 39, 4942–51)(94.3 g, 0.46 mol). The resultant mixture was then heated to 60° C. for 7 hours before cooling to room temperature. Deionised water (100 ml) was then added to the reaction mixture with stirring, followed by aqueous hydrochloric acid (190 ml of a 5 M solution) until the pH of the aqueous layer was between pH 2 and 3. The aqueous layer was then separated, and the organic layer was washed with aqueous potassium carbonate (50 ml of a 0.5 M solution). The aqueous phase was separated and organic phase was washed with saturated brine solution (100 ml). The aqueous layer was then separated and the organic phase was concentrated by distillation under vacuum to give the title compound as a yellow oil (200.3 g, 443 mmol, 98% yield);

$^1$H NMR (CDCl$_3$ 300 MHz) δ: 1.45 (s, 9H), 1.45–1.56 (m, 1H), 1.56–1.74 (m, 6H), 1.74–2.11 (m, 7H), 2.32–2.43 (m, 1H), 2.64 (t, 2H), 3.22–3.30 (m, 2H), 3.27 (s, 3H), 3.30–3.38 (m, 2H), 5.75–5.85 (m, br, 1H), 7.13 (d, 2H), 7.26 (d, 2H); LRMS (ES positive): m/z 452 [M+H]$^+$ ($^{35}$Cl).

Preparation of (2S)-2-{[1-({[3-(4-Chlorophenyl) propyl]amino}carbonyl)-cyclopentyl]methyl}-4-methoxybutanoic acid and its sodium salt (6-A)

To a solution of Intermediate I-6c (9.6 g, 21.2 mmol) in dichloromethane (52 ml) was added trifluoroacetic acid (16.3 ml, 212 mmol) and the resultant solution was stirred at room temperature for 3.75 hours under an atmosphere of N$_2$. To the reaction was then added aqueous sodium carbonate solution (95 ml of a 10% w/v solution) with stirring until the pH of the aqueous layer was between pH 2 and 3. The layers were then separated and the organic layer was extracted with aqueous sodium carbonate solution (2×20 ml of a 10% w/v solution). The aqueous layers were combined and saturated brine (80 ml) was then added, followed by 2-butanone (40 ml). The layers were separated and the aqueous layer was extracted again with 2-butanone (2×50 ml). The combined organic layers were then dried by azeotropic distillation at atmospheric pressure to a volume of 70 ml whereupon crystallisation occurred and the mixture was diluted with 2-butanone (70 ml). The product was then collected by filtration and dried at 50° C. for 65 hours under vacuum to give the crude sodium salt of the title compound as a white solid (5.76 g) that was then purified by recrystallisation as follows. To the crude product was added ethyl acetate (87 ml) and ethanol (13 ml) and the remaining insoluble material was removed by filtration. The ethanol was then removed by azeotropic distillation at atmospheric pressure (to remove 110 ml of solvent) and replaced with ethyl acetate (145 ml) whereupon crystallisation occurred. The resultant crystallised product was then collected by filtration under vacuum to give the pure sodium salt of the title product as a white crystalline solid (4.51 g, 10.8 mmol, 51%); m.p. (ethyl acetate) 214–216° C.;

$^1$H NMR (DMSO-d$_6$ 300 MHz) δ: 1.26–1.58 (m, 8H), 1.62–1.74 (m, 3H), 1.74–1.86 (m, 1H), 1.91–2.07 (m, 3H), 2.57 (t, 2H), 3.03 (q, 2H), 3.10 (s, 3H), 3.13–3.27 (m, 2H), 7.22 (d, 2H), 7.29 (d, 2H), 9.16 (t, br, 1H); LRMS (ES negative); 789 [2M−H]$^-$ ($^{35}$Cl), 394 [M−H]$^-$ ($^{35}$Cl).

For analytical purposes the title product (i.e. the free acid) was obtained by dissolving this sodium salt in water, acidified with 5 M hydrochloric acid and extracted with dichloromethane. Removal of the solvent by blowing a stream of nitrogen over the sample gave the title product;

$^1$H NMR (DMSO-d$_6$ 300 MHz) δ: 1.22–1.80 (m, 11H), 1.81–1.96 (m, 2H), 1.96–2.08 (m, 1H), 2.93–2.27 (m, 1H), 2.53 (t, 2H), 3.03 (q, 2H), 3.11 (s, 3H), 3.16–3.25 (m, 2H), 7.20 (d, 2H), 7.30 (d, 2H), 7.51 (t, 1H); LRMS (ES negative); 789 [2M−H]$^-$ ($^{35}$Cl), 394 [M−H]$^-$ ($^{35}$Cl); HPLC (column: ChiralPak AS (25×0.46 cm); mobile phase: hexane/IPA/acetic acid (95/5/0.5 v/v/v); flow rate: 1.0 ml/min; temperature: ambient; injection volume: 20 μl; detection: UV@ 220 nm; Sample concentration: 1.0 mg/ml prepared in mobile phase) Retention Time: minor enantiomer 11.4 min (5.7%), major enantiomer 14.3 min (94.3%).

Preparation of Mono-hydrate of the Sodium Salt of 6-A

To the sodium salt of 6-A (200 mg) was added to 1 ml of a 3.9% water in isopropanol solution. The resulting slurry was stirred for 12 days whereupon it was isolated by filtration. The product gave the following PXRD pattern listed in Table 5 below.

TABLE 5

| Angle 2-Theta ° | Intensity % % |
|---|---|
| 3.552 | 30.8 |
| 7.154 | 8 |
| 9.526 | 3.1 |
| 10.359 | 15.7 |
| 10.608 | 14.3 |
| 11.03 | 5 |
| 12.369 | 3.7 |
| 12.939 | 13.2 |
| 13.233 | 12.3 |
| 13.835 | 14.2 |
| 14.345 | 37.9 |
| 14.887 | 16 |
| 15.16 | 16.8 |
| 16.372 | 24.9 |
| 16.813 | 6.9 |
| 17.203 | 22.1 |
| 17.408 | 32.7 |
| 17.708 | 13.5 |
| 17.93 | 29 |
| 18.313 | 12 |
| 18.545 | 23.9 |
| 18.811 | 14 |
| 19.7 | 34.2 |
| 19.978 | 100 |
| 20.273 | 90.6 |
| 20.627 | 51.9 |
| 20.829 | 29.4 |
| 20.926 | 28.4 |
| 21.443 | 52.7 |
| 21.611 | 41.6 |
| 21.881 | 21.2 |
| 22.174 | 24.3 |
| 22.472 | 47.1 |
| 22.881 | 35 |
| 23.141 | 23.2 |
| 23.478 | 15.1 |
| 24.088 | 13.9 |
| 24.313 | 12.6 |
| 24.588 | 22.7 |
| 25.013 | 25.8 |
| 25.514 | 29.9 |
| 25.987 | 25.5 |
| 27.107 | 18.2 |
| 27.395 | 30.6 |
| 27.869 | 19.2 |
| 28.716 | 21 |
| 28.788 | 19 |
| 28.989 | 27.2 |
| 30.232 | 13.4 |
| 30.672 | 15 |
| 30.952 | 17.5 |
| 31.437 | 15.7 |
| 31.788 | 13.9 |
| 32.114 | 24.6 |
| 32.998 | 13.3 |
| 33.375 | 18.8 |
| 33.815 | 14 |
| 34.266 | 14.4 |
| 35.705 | 15.7 |
| 35.989 | 14.1 |
| 36.514 | 16.7 |

TABLE 5-continued

| Angle 2-Theta ° | Intensity % % |
|---|---|
| 38.151 | 14.6 |
| 38.925 | 17 |
| 39.091 | 19 |
| 39.961 | 13 |

Differential scanning calorimetry (DSC) was performed using a Perkin Elmer DSC-7 instrument fitted with an automatic sample changer. Approximately 3 mg of the sample was accurately weighed into a 50 microliter aluminium pan and crimp sealed with a perforated lid. The samples were heated at 20° C./minute over the range 40° C. to 300° C. with a nitrogen gas purge. Dehydration events occurred at between 50 and 150° C. and a main melt between 212 and 225° C. The skilled person will appreciate that the melting point may vary outside this range as a result of sample impurity.

Anhydrous Salt:

The sodium salt of compound 6-A gave the following PXRD pattern listed in Table 6 below.

TABLE 6

| Angle 2-Theta ° | Intensity % % |
|---|---|
| 5.463 | 12.2 |
| 6.654 | 100 |
| 7.546 | 66 |
| 9.336 | 31.3 |
| 10.953 | 9.7 |
| 11.571 | 55.9 |
| 12.56 | 10.9 |
| 13.287 | 22.9 |
| 15.125 | 33.6 |
| 15.667 | 60.3 |
| 16.403 | 17.2 |
| 17.024 | 62.2 |
| 17.714 | 95.6 |
| 18.083 | 31.7 |
| 18.64 | 28.8 |
| 18.902 | 82.4 |
| 19.696 | 40.1 |
| 20.406 | 33.9 |
| 20.502 | 31.8 |
| 20.683 | 45.4 |
| 20.942 | 31.5 |
| 21.559 | 92.6 |
| 21.898 | 66.2 |
| 22.274 | 36.6 |
| 22.735 | 30 |
| 23.36 | 56.5 |
| 24.126 | 31.9 |
| 24.388 | 45.2 |
| 24.72 | 25.8 |
| 25.298 | 26.7 |
| 25.579 | 20.4 |
| 26.718 | 17.6 |
| 27.151 | 24.2 |
| 27.46 | 22.7 |
| 27.737 | 20.2 |
| 28.56 | 27.1 |
| 28.926 | 23.8 |
| 29.802 | 23.5 |
| 30.454 | 30.7 |
| 30.885 | 29.2 |
| 31.48 | 21 |
| 32.66 | 16.8 |
| 34.027 | 23.1 |
| 34.494 | 17.6 |

TABLE 6-continued

| Angle 2-Theta ° | Intensity % % |
|---|---|
| 36.011 | 19 |
| 36.997 | 17.4 |
| 38.704 | 21.2 |
| 39.961 | 18.7 |

Biological Assays

The utility of the compounds of the present invention in the practice of the instant invention is evidenced by activity in at least one of the protocols described hereinbelow.

5HT$_{2c}$ Binding Procedure

Affinity of compounds at the serotonin 5HT$_{2c}$ binding site was determined by competition binding in Swiss 3T3 mouse cells (available from the American Type Culture Collection (ATCC), Manassas, Va.) transfected with the human 5HT$_{2c}$ receptor against 3H-5HT. The method was adapted from Roth et al., *J. of Pharm. And Exp. Therap.*, 260(3), 1362–1365 (1992). Cells were grown in DMEM high glucose medium, harvested, homogenized, centrifuged, and resuspended in 50 mM Tris-HCL. They were incubated at 37° C. for 15 minutes, centrifuged, and then resuspended into assay buffer (50 mM Tris-HCl, 4 mM CaCl$_2$, 0.1% ascorbic acid, and 100 µM pargyline at pH 7.7) at 100 volumes per gram. Assay tubes contained 25 µL of 10 nM $^3$H-5HT (1 nM final conc.), and 25 µl of vehicle (assay buffer), blank (10 µM mianserin), or test compound (10× final volume). 200 µl of tissue homogenate was added to each tube, vortexed, and incubated for 30 minutes at 37° C. Samples were then rapidly filtered under vacuum with a Skatron™ cell harvester (available from Molecular Devices Corporation, Sunnyvale, Calif.) using GF/B filters presoaked in 0.5% polyethyleneimine (PEI), and washed with 2×5 mL cold 50 mM Tris-HCl. Filter mats were removed and counted in a Wallac Betaplate counter (available from PerkinElmer Life Sciences, Gaithersburg, Md.). Percent inhibition of specific binding by test compounds was used to calculate the Ki, or extrapolate concentration of test compound necessary to inhibit one-half of the total specific binding for each compound.

The compounds from the Examples above demonstrated Ki values for 5HT$_{2c}$ binding in the range from about 0.1 nM to 586.5 nM (Example 1-AW):

5HT$_{2A}$ Binding Procedure

Affinity of compounds at the serotonin 5HT$_{2A}$ binding site was determined by competition binding in NIH 3T3 mouse cells transfected with the rat 5HT$_{2A}$ receptor using 125I-DOI. The method was adapted from Leonhardt et al., *Molecular Pharmacology*, 42, 328–335 (1992). Frozen cell paste was homgenized in 50 mM tris-HCl buffer pH 7.4 containing 2 mM MgCl$_2$ using a Polytron and centrifuged at 45000×g for ten minutes. The resulting pellet was resuspended in fresh ice-cold 50 mM tris-HCl buffer pH 7.4 containing 2 mM MgCl$_2$ using a Polytron™ and centrifuged again at 45000×g for ten minutes. The final pellet was resuspended in 50 mM tris-HCl buffer pH 7.4 containing 2 mM MgCl$_2$ at a concentraion of 5 mg/mL. Wells in a 96 well plate contained 25 µL of 0.7 nM 125I-DOI (70 pM final conc.), and 25 µL of vehicle (assay buffer), blank (10 µM cinanserin), or test compound (10× final volume). 200 µl of tissue homogenate was added to each well and incubated for 15 minutes at 37° C. on a shaker. Samples were then rapidly filtered under vacuum with a cell harvester (Skatron™) using GF/B filters presoaked in 0.5% polyethyleneimine (PEI), and washed with 2×5 mL cold 50 mM tris-HCl. Filter mats were removed, dried and counted in a Wallac Betaplate counter. Concentration-response curves of the % inhibition of specific binding and log concentration by test compounds were used to determine the IC$_{50}$ for each compound and the Ki value calculated based on the Cheng-Prusof equation (Ki=IC50/(1+(L/Kd)), where L is the concentration of the radioligand used in the binding assay and the Kd was based on previous saturation studies with the radioligand.

The compounds from the Examples above demonstrated Ki values for 5HT$_{2a}$ binding in the range from 0.5 nM to 1.0 µM (Example 4-R). No 5HT$_{2a}$ binding data was generated for Examples 1-AE, 1-AF, 1-AL and 1-AH.

Functional Assay

Swiss 3T3 cells expressing r-5HT$_{2C}$, r-5HT$_{2A}$, h-5HT$_{2C}$ or h-5HT$_{2A}$ receptors were seeded at a density of 12,500 cells/well in 384 well black/clear collagen-coated plates. Forty eight (48) hrs later the cells were loaded with the calcium sensitive dye, Fluo 4-AM (4 µM dissolved in DMSO containing pluronic acid) in serum free DMEM in the presence of probenicid (2.5 mM) for 75 minutes at 37° C. in a CO$_2$ incubator. Unincorporated dye was removed by washing 3 times with a HEPES-buffered saline containing probenicid (2.5 mM) using a Skatron™ cell washer (final volume 30 µL).

Plates were added to a fluorometric imaging plate reader (FLIPR 384 available from Molecular Devices Corporation) individually and fluorescence measurements were taken every 2 seconds over an 85 seconds period. Test compound additions were made simultaneously to all 384 wells after 20 seconds of baseline recording. Concentration-response curves were generated using Graphpad Prism™ (available from GraphPad Software, Inc., San Diego, Calif.) and agonist efficacies were generated as % of the response to 10 µM 5-HT (considered as 100%). Estimation of antagonist potencies (functional Kis) were generated by measuring inhibition of the test compound response to 5-HT (10 nM for 5-HT$_{2C}$ and 50 nM for 5-HT$_{2A}$) and applying the Cheng Prusoff equation.

The functional data for the compounds listed in the Examples above utilizing the 5-HT$_{2c}$ expressed NIH 3T3 cells is summarized below.

Examples 1-A through 1-D, 1-G through 1-J, 1-L, 1-M, 1-O, 1-P, 1-AC, 1-AD, 1-AG, 1-AI, 1-AK, 1-AM through 1-AR, 1-AU through 1-CJ, 2-A, 3-A through 3-S, 4-A, 4-B, 4-E through 4-T, and 5-A demonstrated EC$_{50}$ values less than or equal to 1.0 µM.

Examples 1-E, 1-F, 1-K, 1-Q, 1-S, 1-X, 1-AB, 1-AJ, and 1-AL demonstrated EC$_{50}$ values greater than 1.0 µM.

Examples 1-N, 1-R, 1-U, 1-W, 1-Z, 1-AA, 1-AE, 1-AF, 1-AH, 1-AL, 1-AO, 1-AS, 1-AT, 4-C, and 4-D acted as an antagonist.

Example 1-V demonstrated no activity at 10 µM.

Spontaneous Food Intake

Wistar rats was administered test compound either orally or subcutaneously in a 30% β-cyclodextrin vehicle 30 minutes prior to the onset of the dark cycle. Food intake was monitored using a computerized system that monitors the intake of individual animals. Food intake was monitored for at least 16 hours after administration of the test compound.

Sexual Dysfunction

Example A

Treatment of MED

A representative compound of formula (I) has been demonstrated to induce increases in penile intracavernosal pressure (ICP) in the conscious male rat.

Test Compound: 6'-(2,5-Difluoro-benzyloxy)-3,4,5,6-tetrahydro-2H-[1,2']bipyrazinyl (Example I-K)

ICP Protocol: Intra cavernosal pressure (ICP) can be measured in the conscious rat by means of telemetric recording. A catheter is surgically implanted into the corpus cavernosum. The end of the catheter is linked to a device, which senses, processes, and transmits information digitally from within the animal. A receiver converts the radiofrequency signal from the implant to a digital pulse stream that is readable by a data collection system. The PC-based system collects telemetred data from the animal.

Surgery:—Induce and maintain general anaesthesia using 5% Isoflurane® in a carrier gas of 0.5 L/min oxygen and 1 L/min nitrous oxide to induce anaesthesia, reducing to 2% Isoflurane for maintenance anaesthesia. Administer 5 mg/kg subcutaneously (s.c.) Carprofen (Rimadyl® Large Animal Injection, 50 mg/ml, Pfizer Animal Health) at induction of anaesthesia, at end of day of surgery and on the morning of first day post-surgery to minimise pain and discomfort.

Implantation of corpus cavernosal probe:—Shave the skin of the ventral abdomen and extend to include the area around the penis and ventral scrotum. Clean and disinfect the shaved area. Place the rat in dorsal recumbency. Make a mid-line incision from the external base of the penis, running caudally for approximately 2 cm. Locate and expose the internal structure of the penis and identify the corpus cavernosum. Make a mid-line laparotomy, approximately 4 cm in length to access the abdominal cavity. Pierce the abdominal wall via the caudal incision with a suitable trocar and cannula, taking care not to damage any internal organs. Place the implant body in the abdominal cavity with the catheter orientated caudally and pass the catheter tip through the body wall via the preplaced cannula. Implant used is model TA11PA-C40, 8 mm catheter, with modified 3 mm tip (Data Sciences International Inc.). Secure the implant body to the abdominal wall using non-absorbable sutures and partially close the abdominal incision. Reflect the tip of the penis cranially and retract the caudal incision to optimise the surgical field. Carefully isolate approximately 10 mm of the internal structure of the penis from the surrounding tissue. Carefully reflect the corpus spongiosum to one side to give access to the corpus cavernosum. Access the corpus cavernosum using a modified over-the-needle catheter to puncture the tunica. Introduce the catheter tip via the preplaced catheter and advance until fully inserted. Carefully remove the access catheter and apply a suitable tissue adhesive to the insertion site. Observe for leakage. Close the subcutaneous fat layer in the caudal incision before closing with an appropriate absorbable suture. Instil approximately 5 ml of warm saline through the abdominal incision and complete closure of the mid-line incision. Close the skin incision with an appropriate absorbable suture.

Postoperative care:—Measure food and water intake and monitor bodyweight daily for at least 7 days post surgery, then 2–3 times weekly. Give Lectade® (Pfizer Animal Health) in drinking water for 3 days post surgery. House rats singly, and transfer to reverse light/dark conditions 5 days post surgery. Named Veterinary Surgeon (or Deputy) to issue a certificate of fitness to continue 2 days post surgery. Start using rats experimentally 7 days post surgery.

Experimental Procedure:—Perform experiment in room with reverse light/dark conditions. On day of experiment, place rat in home cage on receiver pad (PhysioTel® Model RPC-1, Data Sciences International Inc.) and leave to acclimatise for approximately one hour. Ensure that the rat has food and water ad lib. Take baseline reading of intra cavernosal pressure (ICP) for approximately 5 minutes. Transfer the data via a floppy disk to an Excel spreadsheet. Inject the rat with compound subcutaneously or via the jugular vein catheter (JVC). If using the JVC, flush through with sterile saline after dosing and seal with a saline/glucose lock solution. The interval between administration of compound and ICP measurement will vary with the compound to be tested. An interval of 30–60 min post s.c. injection is a good guide. The test compounds were dissolved in 50% β-cyclodextrin in saline. They were administered at a dose of 5–10 mg/kg subcutaneously (s.c.). Apomorphine hydrochloride hemihydrate (Sigma A-4393) at 60 µg/kg s.c. was used as a positive control as it has pro-erectile properties. Record ICP over a 15 minute period, starting at 30 minutes post injection i.e. from 30 to 35 minutes and repeat for two further 15 minute periods commencing at 60 minutes post injection and 120 minutes post injection respectively. Record ICP for 15 minutes. A signal from the receiver pad feeds through to the Data Exchange Matrix® and hence to the software (Dataquest ART® acquisition system, Data Sciences International Inc.). Transfer the data via a floppy disk to an Excel spreadsheet for analysis.

Table 1 illustrates the ICP data obtained from studies using the test compound of formula (I) as described hereinbefore. The data in Table 7 demonstrates that 6'-(2,5-Difluoro-benzyloxy)-3,4,5,6-tetrahydro-2H-[1,2'] bipyrazinyl induced proerectile effects in the conscious rat. This compound significantly increased the number of erectogenic events in a 15 minute test period when dosed at 5 mg/kg s.c. There was no difference in the number of erectogenic events induced at 120 minutes after dosing.

TABLE 7

| | |
|---|---|
| Number of erectogenic events @ 60 min | 1.5 ± 0.3 |
| Number of erectogenic events @ 120 min | 1.3 ± 0.5 |

Example B

Compounds of Formula (I) in Combination with PDE5i for Treatment of MED

The effects of concomitant administration of compound (s) of formula (I) in combination with a PDE5 inhibitor on the penile intracavernosal pressure (ICP) in an anaesthetised rabbit model of erection can be measured according to the following protocol.

Experimental Protocol

Male New Zealand rabbits (~2.5 kg) are pre-medicated with a combination of Medetomidine (Domitor®) 0.5 ml/kg inramuscularly (i.m.), and Ketamine (Vetalar®) 0.25 ml/kg i.m. whilst maintaining oxygen intake via a face mask. The rabbits are tracheotomised using a Portex™ uncuffed endotracheal tube 3 ID (internal diameter), connected to ventilator and maintained at a ventilation rate of 30–40 breaths per minute, with an approximate tidal volume of 18–20 ml, and a maximum airway pressure of 10 cm $H_2O$. Anaesthesia was then switched to Isoflurane® and ventilation continued with $O_2$ at 2 liters/min. The right marginal ear vein was cannulated using a 23G or 24G catheter, and Lactated Ringer solution perfused at 0.5 ml/min. The rabbit was maintained at 3% Isoflurane during invasive surgery, dropping to 2% for maintenance anaesthesia. The left jugular vein was exposed, isolated and then cannulated with a PVC catheter (17 gauge/17G) for the infusion of drugs and the test compounds.

The left groin area of the rabbit was shaved and a vertical incision was made approximately 5 cm in length along the thigh. The femoral vein and artery were exposed, isolated and then cannulated with a PVC catheter (17G) for the infusion of drugs and compounds. Cannulation was repeated for the femoral artery, inserting the catheter to a depth of 10 cm to ensure that the catheter reached the abdominal aorta. This arterial catheter was linked to a Gould system to record blood pressure. Samples for blood gas analysis were also taken via the arterial catheter. Systolic and diastolic pressures were measured, and the mean arterial pressure calculated using the formula (diastolic×2+systolic)÷3. Heart rate was measured via the pulse oxymeter and Po-ne-mah data acquisition software system (Ponemah Physiology Platform, Gould Instrument Systems Inc).

A ventral midline incision was made into the abdominal cavity. The incision was about 5 cm in length just above the pubis. The fat and muscle was bluntly dissected away to reveal the hypogastric nerve which runs down the body cavity. It was essential to keep close to the side curve of the pubis wall in order to avoid damaging the femoral vein and artery which lie above the pubis. The sciatic and pelvic nerves lie deeper and were located after further dissection on the dorsal side of the rabbit. Once the sciatic nerve is identified, the pelvic nerve was easily located. The term pelvic nerve is loosely applied; anatomy books on the subject fail to identify the nerves in sufficient detail. However, stimulation of the nerve causes an increase in intracavernosal pressure and cavernosal blood flow, and innervation of the pelvic region. The pelvic nerve was freed away from surrounding tissue and a Harvard bipolar stimulating electrode was placed around the nerve. The nerve was slightly lifted to give some tension, then the electrode was secured in position. Approximately 1 ml of light paraffin oil was placed around the nerve and electrode. This acts as a protective lubricant to the nerve and prevents blood contamination of the electrode. The electrode was connected to a Grass S88 Stimulator. The pelvic nerve was stimulated using the following parameters: —5V, pulse width 0.5 ms, duration of stimulus 20 seconds with a frequency of 16 Hz. Reproducible responses were obtained when the nerve was stimulated every 15–20 minutes. Several stimulations using the above parameters were performed to establish a mean control response. The compound(s) to be tested were infused, via the jugular vein, using a Harvard 22 infusion pump allowing a continuous 15 minute stimulation cycle. The skin and connective tissue around the penis was removed to expose the penis. A catheter set (Insyte-W, Becton-Dickinson 20 Gauge 1.1×48 mm) was inserted through the tunica albica into the left corpus cavernosal space and the needle removed, leaving a flexible catheter. This catheter was linked via a pressure transducer (Ohmeda 5299-04) to a Gould system to record intracavernosal pressure (ICP). Once an intracavernosal pressure was established, the catheter was sealed in place using Vetbond (tissue adhesive, 3M). Heart rate was measured via the pulse oxymeter and Po-ne-mah data acquisition software system (Ponemah Physiology Platform, Gould Instrument Systems Inc).

Intracavernosal blood flow was recorded either as numbers directly from the Flowmeter using Po-ne-mah data acquisition software (Ponemah Physiology Platform, Gould Instrument Systems Inc), or indirectly from Gould chart recorder trace. Calibration was set at the beginning of the experiment (0–125 ml/min/100 g tissue).

All data are reported as mean ±s.e.m. (standard error of the mean). Significant changes were identified using Student's t-tests. The test compounds were dissolved in 50% β-cyclodextrin in saline. They were administered at a dose of 5–10 mg/kg subcutaneously (s.c.).

Using the protocol described hereinbefore beneficial effects on ICP can be demonstrated for the concomitant administration of 6'-(2,5-Difluoro-benzyloxy)-3,4,5,6-tetrahydro-2H-[1,2']bipyrazinyl (5–10 mg/kg s.c.) and a selective inhibitor of PDE5 (3-ethyl-5-{5-[4-ethylpiperzino) sulphonyl-2-propoxyphenyl}-2-(2-pyridylmethyl)-6,7-dihydro-2H-pyrazolo[4,3-d]pyrimidin-7-one (as described in WO98/491066) (1 mg/kg i.v.(intravenously)). These studies suggest that there are a number of clinical benefits of concomitant administration of a PDE5 inhibitor and a compound of formula (I). Such benefits include increased efficacy and opportunities to treat MED subgroups that do not respond to other MED mono-therapies.

Example C

Treatment of FSAD

Serotonin 5HT2C receptor agonists potentiate pelvic nerve-stimulated increases in female genital blood flow in the anaesthetised rabbit model of sexual arousal.

The normal sexual arousal response consists of a number of physiological responses that are observed during sexual excitement. These changes such as vaginal, labial and clitoral engorgement result from increases in genital blood flow. Engorgement leads to increased vaginal lubrication via plasma transudation, increased vaginal compliance (relaxation of vaginal smooth muscle) and increases in vaginal and clitoral sensitivity.

Female sexual arousal disorder (FSAD) is a highly prevalent sexual disorder affecting up to 40% of pre-, per- and postmenopausal (±HRT) women. The primary consequence of FSAD is reduced genital engorgement or swelling which manifests itself as a lack of vaginal lubrication and a lack of pleasurable genital sensation. Secondary consequences include reduced sexual desire, pain during intercourse and difficulty in achieving orgasm. The most common cause of FSAD is decreased genital blood flow resulting in reduced vaginal, labial and clitoral engorgement (Berman, J., Goldstein, I., Werbin, T. et al. (1999a). Double blind placebo controlled study with crossover to assess effect of sildenafil on physiological parameters of the female sexual response. *J. Urol.*, 161, 805; Goldstein, I. & Berman, J. R. (1998). Vasculogenic female sexual dysfunction: vaginal engorgement and clitoral erectile insufficiency syndromes. *Int. J. Impot. Res.*, 10, S84–S90; Park, K., Goldstein, I., Andry, C., et al. (1997). Vasculogenic female sexual dysfunction: The hemodynamic basis for vaginal engorgement insufficiency and clitoral erectile insufficiency. *Int. J. Impotence Res.*, 9, 27–37; Werbin, T., Salimpour, P., Berman, L., et al. (1999). Effect of sexual stimulation and age on genital blood flow in women with sexual stimulation. *J. Urol.*, 161, 688).

As explained herein, the present invention provides a means for restoring or potentiating the normal sexual arousal response in women suffering from FSAD, by enhancing genital blood flow.

Method

Female New Zealand rabbits (~2.5 kg) were premedicated with a combination of Medetomidine (Domitor®) 0.5 ml/kg intramuscularly (i.m.), and Ketamine (Vetalar®) 0.25 ml/kg i.m. whilst maintaining oxygen intake via a face mask. The rabbits were tracheotomised using a Portex™ uncuffed endotracheal tube 3 ID (internal diameter), connected to ventilator and maintained at a ventilation rate of 30–40 breaths per minute, with an approximate tidal volume of 18–20 ml, and a maximum airway pressure of 10 cm $H_2O$. Anaesthesia was then switched to Isoflurane® and ventilation continued with $O_2$ at 2 l/min. The right marginal ear vein was cannulated using a 23G or 24G catheter, and Lactated Ringer solution perfused at 0.5 ml/min. The rabbit was maintained at 3% Isoflurane® during invasive surgery, dropping to 2% for maintenance anaesthesia.

The left groin area of the rabbit was shaved and a vertical incision was made approximately 5 cm in length along the thigh. The femoral vein and artery were exposed, isolated and then cannulated with a PVC catheter (17G) for the infusion of drugs and compounds. Cannulation was repeated for the femoral artery, inserting the catheter to a depth of 10 cm to ensure that the catheter reached the abdominal aorta. This arterial catheter was linked to a Gould system to record blood pressure. Samples for blood gas analysis were also taken via the arterial catheter. Systolic and diastolic pressures were measured, and the mean arterial pressure calculated using the formula (diastolic×2+systolic)÷3. Heart rate was measured via the pulse oxymeter and Po-ne-mah data acquisition software system (Ponemah Physiology Platform, Gould Instrument Systems Inc).

A ventral midline incision was made into the abdominal cavity. The incision was about 5 cm in length just above the pubis. The fat and muscle was bluntly dissected away to reveal the hypogastric nerve which runs down the body cavity. It was essential to keep close to the side curve of the pubis wall in order to avoid damaging the femoral vein and artery, which lie above the pubis. The sciatic and pelvic nerves lie deeper and were located after further dissection on the dorsal side of the rabbit. Once the sciatic nerve is identified, the pelvic nerve was easily located. The term pelvic nerve is loosely applied; anatomy books on the subject fail to identify the nerves in sufficient detail. However, stimulation of the nerve causes an increase in vaginal and clitoral blood flow, and innervation of the pelvic region. The pelvic nerve was freed away from surrounding tissue and a Harvard bipolar stimulating electrode was placed around the nerve. The nerve was slightly lifted to give some tension, then the electrode was secured in position. Approximately 1 ml of light paraffin oil was placed around the nerve and electrode. This acts as a protective lubricant to the nerve and prevents blood contamination of the electrode. The electrode was connected to a Grass S88 Stimulator. The pelvic nerve was stimulated using the following parameters:—5V, pulse width 0.5 ms, duration of stimulus 10 seconds and a frequency range of 2 to 16 Hz. Reproducible responses were obtained when the nerve was stimulated every 15–20 minutes. A frequency response curve was determined at the start of each experiment in order to determine the optimum frequency to use as a sub-maximal response, normally 4 Hz. A ventral midline incision was made, at the caudal end of the pubis, to expose the pubic area. Connective tissue was removed to expose the tunica of the clitoris, ensuring that the wall was free from small blood vessels. The external vaginal wall was also exposed by removing any connective tissue. One laser Doppler flow probe was inserted 3 cm into the vagina, so that half the probe shaft was still visible. A second probe was positioned so that it lay just above the external clitoral wall. The position of these probes was then adjusted until a signal was obtained. A second probe was placed just above the surface of a blood vessel on the external vaginal wall. Both probes were clamped in position.

Test Compounds 8,9-dichloro-2,3,4,4a-tetrahydro-1H-pyrazino[1,2-a]quinoxalin-5(6H)-one, which corresponds to Compound 75 of Chaki and Nakazato—Expert Opin. Ther. Patents (2001), 11(11):1677–1692 (see Section 3.9—$5HT_{2c}$ on page 1687 and FIG. 7 on page 1686), or Compound (6) of Isaac—Drugs of the Future (2001), 26(4):383–393 (see FIG. 2 on page 385).

8,9-dichloro-2,3,4,4a-tetrahydro-1H-pyrazino[1,2-a]quinoxalin-5(6H)-one was dissolved in 50% β-cyclodextrin in saline. It was administered at a dose of 5 mg/kg subcutaneously (s.c.).

Data Recordal

Vaginal and clitoral blood flow was recorded either as numbers directly from the Flowmeter using Po-ne-mah data acquisition software (Ponemah Physiology Plafform, Gould Instrument Systems Inc), or indirectly from Gould chart recorder trace. Calibration was set at the beginning of the experiment (0–125 ml/min/100 g tissue).All data are reported as mean ± standard error of the mean (s.e.m.). Significant changes were identified using Student's t-tests.

Results

The serotonin 5HT2C receptor agonist (8,9-dichloro-2,3,4,4a-tetrahydro-1H-pyrazino[1,2-a]quinoxalin-5(6H)-one; 5 mg/kg s.c.) acts as a potent enhancer of pelvic-nerve stimulated (PNS) increases in vaginal and clitoral blood flow in the anaesthetised rabbit (see Table 8 below). The potentiation was significant 30 mins after s.c. dosing and remained elevated for circa 1 hr. The 5HT2c agonist had no effect on basal genital blood flow in the absence of PNS (see Table 8 below). This reinforces our view that a 5HT2c receptor agonist will enhance the arousal response by potentiating the mechanism(s) that control sexual arousal/genital blood flow, thereby treating FSAD, and will not induce arousal in the absence of sexual stimulation. Since these agents also enhance clitoral blood flow it is likely that they will be effective in the treatment of orgasmic disorders.

Table 8 below illustrates that 8,9-dichloro-2,3,4,4a-tetrahydro-1H-pyrazino[1,2-a]quinoxalin-5(6H)-one (5 mg/kg s.c.) potentiates pelvic nerve stimulated increases in genital blood flow circa 35% after subcutaneous administration in the anaesthetised rabbit model of sexual arousal.

TABLE 8

| Time after injection of Compound 8,9-dichloro-2,3,4,4a-tetrahydro-1H-pyrazino[1,2-a]quinoxalin-5(6H)-one (min) | Unstimulated vaginal blood flow (Laser Doppler units) | Pelvic nerve stimulated increases in vaginal blood flow (Laser Doppler units) | Compound-induced potentiation of stimulated vaginal blood flow |
|---|---|---|---|
| Pre dose | 148 +/- 6 | 241 +/- 10 | — |
| 15 | 185 | 292 | 21 |
| 30 | 162 | 325 | 34 |
| 45 | 150 | 295 | 22 |
| 60 | 127 | 325 | 34 |
| 75 | 137 | 252 | 4 |
| 90 | 132 | 247 | 2 |

What is claimed is:

1. A compound of Formula (IA)

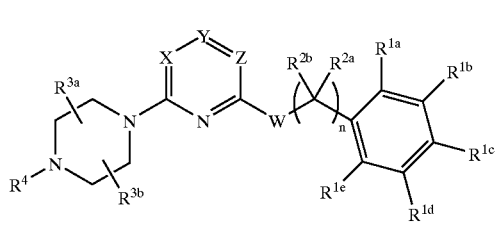

(IA)

wherein
Y is nitrogen;
X and Z are each independently CR, where R for each occurrence is hydrogen, halogen, $(C_1-C_4)$alkyl, amino, or $(C_1-C_4)$alkylamino;
W is amino, $(C_1-C_4)$alkylamino, or acetylamino;
at least one of $R^{1a}$, $R^{1b}$, $R^{1d}$, and $R^{1e}$ is independently selected from the group consisting of halogen, nitro, amino, $(C_1-C_4)$alkylamino, cyano, —C(O)NH$_2$, $(C_1-C_4)$alkyl, halo-substituted$(C_1-C_4)$alkyl, $(C_1-C_4)$alkoxy, and halo-substituted$(C_1-C_4)$alkoxy, or $R^{1a}$ and $R^{1b}$ taken together form a five- or six-membered, aromatic or partially or fully saturated fused ring, or $R^{1a}$ taken together with $R^{2a}$ or $R^{2b}$ forms a five- or six-membered fully saturated fused ring;
$R^{1c}$ is hydrogen;
$R^{2a}$ and $R^{2b}$ are each independently hydrogen, $(C_1-C_4)$alkyl, partially or fully saturated $(C_3-C_6)$cycloalkyl, or one of which taken together with $R^{1a}$ forms a five- or six-membered, fully saturated fused ring;
n is 0, 1, or 2;
$R^{3a}$ and $R^{3b}$ are each independently hydrogen, halogen, $(C_1-C_4)$alkyl, or $(C_1-C_4)$alkyl substituted with hydroxy, fluoro, or $(C_1-C_4)$alkoxy;
$R^4$ is hydrogen, hydroxy, $(C_1-C_4)$alkyl, $(C_1-C_4)$alkyl substituted with hydroxy or cyano, $(C_1-C_4)$alkylcarbonyl, $(C_1-C_4)$alkoxy, $(C_1-C_4)$alkoxycarbonyl, or $(C_3-C_4)$alkenyl;
a nitrogen oxide thereof, a prodrug of said compound or said nitrogen oxide; a pharmaceutically acceptable salt of said compound, said nitrogen oxide, or said prodrug, or a solvate or hydrate of said compound, said nitrogen oxide, said prodrug, or said salt.

2. The compound of claim 1 wherein
Y is nitrogen;
X and Z are each independently CR, where R is hydrogen, chloro, fluoro, methyl, or amino;

(i) $R^{1a}$ is halogen, $(C_1-C_4)$alkyl, trifluoromethyl, methoxy, or trifluoromethoxy, and $R^{1b}$, $R^{1d}$ and $R^{1e}$ are each hydrogen,
(ii) $R^{1b}$ is halogen, methyl, methoxy, nitro, amino, cyano, or —C(O)NH$_2$ and $R^{1a}$, $R^{1d}$ and $R^{1e}$ are each hydrogen,
(iii) $R^{1a}$ and $R^{1b}$ are each independently halogen or methyl and $R^{1d}$ and $R^{1e}$ are each hydrogen,
(iv) $R^{1b}$ and $R^{1d}$ are each independently halogen or methyl and $R^{1a}$ and $R^{1e}$ are each hydrogen,
(v) $R^{1a}$ and $R^{1d}$ are each independently halogen or methyl and $R^{1b}$ and $R^{1e}$ are each hydrogen,
(vi) $R^{1a}$ and $R^{1e}$ are each independently halogen or methyl and $R^{1b}$ and $R^{1d}$ are each hydrogen, or
(vii) $R^1$, $R^{1b}$ and $R^{1d}$ are each independently halogen or methyl and $R^{1e}$ is hydrogen;
W is amino, or acetylamino;
n is 1;
$R^{2a}$ and $R^{2b}$ are each independently methyl or hydrogen;
$R^{3a}$ and $R^{3b}$ are each independently hydrogen or $(C_1-C_2)$alkyl; and
$R^4$ is hydrogen or $(C_1-C_4)$alkyl;
a nitrogen oxide thereof, a prodrug of said compound or said nitrogen oxide; a pharmaceutically acceptable salt of said compound, said nitrogen oxide, or said prodrug, or a solvate or hydrate of said compound, said nitrogen oxide, said prodrug, or said salt.

3. The compound of claim 1 wherein
Y is N;
X and Z are each independently CR, where R is hydrogen;
(i) $R^{1a}$ is halogen, methyl, or trifluoromethyl and $R^{1b}$, $R^{1d}$ and $R^{1e}$ are each hydrogen,
(ii) $R^{1b}$ is halogen, methyl, nitro, amino, cyano or —C(O)NH$_2$ and $R^{1a}$, $R^{1d}$ and $R^{1e}$ are each hydrogen,
(iii) $R^{1b}$ and $R^{1d}$ are each independently halogen or methyl and $R^{1a}$ and $R^{1e}$ are each hydrogen, or
(iv) $R^{1a}$ and $R^{1d}$ are each independently halogen or methyl and $R^{1b}$ and $R^{1e}$ are each hydrogen;
W is amino, or acetylamino;
n is 1;
$R^{2a}$ and $R^{2b}$ are each independently methyl or hydrogen;
$R^{3a}$ is hydrogen, (2R)-methyl, or (2R)-ethyl;
$R^{3b}$ is hydrogen; and
$R^4$ is hydrogen;
a nitrogen oxide thereof, a prodrug of said compound or said nitrogen oxide; a pharmaceutically acceptable salt of said compound, said nitrogen oxide, or said prodrug, or a solvate or hydrate of said compound, said nitrogen oxide, said prodrug, or said salt.

4. The compound of claim 1 wherein

Y is N,

X and Z are each independently CR, where R for each occurrence is hydrogen or methyl;

(i) $R^{1a}$ is halogen, or methyl and $R^{1b}$, $R^{1d}$ and $R^{1e}$ are each hydrogen, (ii) $R^{1b}$ is halogen, methyl, nitro, amino, cyano, or —C(O)NH$_2$ and $R^{1a}$, $R^{1d}$ and $R^{1e}$ are each hydrogen, (iii) $R^{1b}$ and $R^{1d}$ are each independently halogen or methyl and $R^{1a}$ and $R^{1e}$ are each hydrogen, or (iv) $R^{1a}$ and $R^{1d}$ are each independently halogen or methyl and $R^{1b}$ and $R^{1e}$ are each hydrogen;

W is amino, or acetylamino;

n is 1;

$R^{2a}$ and $R^{2b}$ are each independently methyl or hydrogen;

$R^{3a}$ is hydrogen, (2R)-methyl, or (2R)-ethyl;

$R^{3b}$ is hydrogen; and $R^4$ is hydrogen;

a nitrogen oxide thereof, a prodrug of said compound or said nitrogen oxide; a pharmaceutically acceptable salt of said compound, said nitrogen oxide, or said prodrug, or a solvate or hydrate of said compound, said nitrogen oxide, said prodrug, or said salt.

5. The compound of claim 1 selected from the group consisting of (3-fluoro-benzyl)-(3,4,5,6-tetrahydro-2H-[1,2']bipyrazinyl-6'-yl)-amine;

(3-chloro-benzyl)-(3,4,5,6-tetrahydro-2H-[1,2']bipyrazinyl-6'-yl)-amine;

(3,5-difluoro-benzyl)-(3,4,5,6-tetrahydro-2H-[1,2']bipyrazinyl-6'-yl)-amine;

3-[(3,4,5,6-tetrahydro-2H-[1,2']bipyrazinyl-6'ylamino)-methyl]-benzonitrile;

(2,5-difluoro-benzyl)-(3,4,5,6-tetrahydro-2H-[1,2']bipyrazinyl-6'-yl)-amine;

(3,5-dichloro-benzyl)-(3,4,5,6-tetrahydro-2H-[1,2']bipyrazinyl-6'-yl)-amine;

(3-chloro-benzyl)-(2-methyl-3,4,5,6-tetrahydro-2H-[1,2']bipyrazinyl-6'-yl)-amine;

(3-fluoro-benzyl)-(2-methyl-3,4,5,6-tetrahydro-2H-[1,2']bipyrazinyl-6'-yl)-amine;

(2-chloro-benzyl)-(3,4,5,6-tetrahydro-2H-[1,2']bipyrazinyl-6'-yl)-amine;

(2-chloro-6-fluoro-benzyl)-(3,4,5,6-tetrahydro-2H-[1,2']bipyrazinyl-6'-yl)-amine;

(2,3-difluoro-benzyl)-(3,4,5,6-tetrahydro-2H-[1,2']bipyrazinyl-6'-yl)-amine; and N-(3-chloro-benzyl)-N-(3,4,5,6-tetrahydro-2H-[1,2']bipyrazinyl-6'-yl)-acetamide;

a nitrogen oxide thereof, a prodrug of said compound or said nitrogen oxide; a pharmaceutically acceptable salt of said compound, said nitrogen oxide, or said prodrug, or a solvate or hydrate of said compound, said nitrogen oxide, said prodrug, or said salt.

6. The compound of claim 1 selected from the group consisting of (3-fluoro-benzyl)-(3,4,5,6-tetrahydro-2H-[1,2']bipyrazinyl-6'-yl)-amine;

(3-chloro-benzyl)-(3,4,5,6-tetrahydro-2H-[1,2']bipyrazinyl-6'-yl)-amine;

(3,5-difluoro-benzyl)-(3,4,5,6-tetrahydro-2H-[1,2']bipyrazinyl-6'-yl)-amine;

(3,5-dichloro-benzyl)-(3,4,5,6-tetrahydro-2H-[1,2']bipyrazinyl-6'-yl)-amine;

(2-chloro-6-fluoro-benzyl)-(3,4,5,6-tetrahydro-2H-[1,2']bipyrazinyl-6'-yl)-amine; and N-(3-chloro-benzyl)-N-(3,4,5,6-tetrahydro-2H-[1,2']bipyrazinyl-6'-yl)-acetamide;

a nitrogen oxide thereof, a prodrug of said compound or said nitrogen oxide; a pharmaceutically acceptable salt of said compound, said nitrogen oxide, or said prodrug, or a solvate or hydrate of said compound, said nitrogen oxide, said prodrug, or said salt.

7. The compound of claim 1 which is (3-fluoro-benzyl)-(3,4,5,6-tetrahydro-2H-[1,2']bipyrazinyl-6'-yl)-amine;

a nitrogen oxide thereof, a prodrug of said compound or said nitrogen oxide; a pharmaceutically acceptable salt of said compound, said nitrogen oxide, or said prodrug, or a solvate or hydrate of said compound, said nitrogen oxide, said prodrug, or said salt.

8. A compound of Formula (IA)

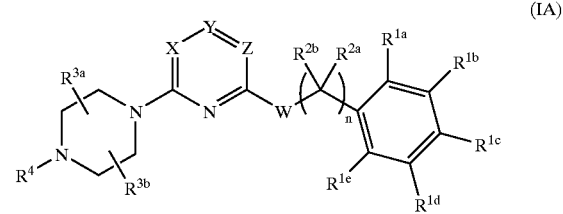

(IA)

wherein

Y is nitrogen;

X and Z are each independently CR, or

X is CH and Z is CR, or

X is CR and Z is CH, where R for each occurrence is halogen, $(C_1-C_4)$alkyl, amino, or $(C_1-C_4)$alkylamino; or W is oxy or thio;

at least one of $R^{1a}$, $R^{1b}$, $R^{1d}$, and $R^{1e}$ is independently selected from the group consisting of halogen, nitro, amino, $(C_1-C_4)$alkylamino, cyano, —C(O)NH$_2$, $(C_1-C_4)$alkyl, halo-substituted$(C_1-C_4)$alkyl, $(C_1-C_4)$alkoxy, and halo-substituted$(C_1-C_4)$alkoxy, or $R^{1a}$ and $R^{1b}$ taken together form a five- or six-membered, aromatic or partially or fully saturated fused ring, or $R^{1a}$ taken together with $R^{2a}$ or $R^{2b}$ forms a five- or six-membered, fully saturated fused ring;

$R^{1c}$ is hydrogen;

$R^{2a}$ and $R^{2b}$ are each independently hydrogen, $(C_1-C_4)$alkyl, partially or fully saturated $(C_3-C_6)$cycloalkyl, or one of which taken together with $R^{1a}$ forms a five- or six-membered, fully saturated fused ring;

n is 0, 1, or 2;

$R^{3a}$ and $R^{3b}$ are each independently hydrogen, halogen, $(C_1-C_4)$alkyl, or $(C_1-C_4)$alkyl substituted with hydroxy, fluoro, or $(C_1-C_4)$alkoxy;

$R^4$ is hydrogen, hydroxy, $(C_1-C_4)$alkyl, $(C_1-C_4)$alkyl substituted with hydroxy or cyano, $(C_1-C_4)$alkylcarbonyl, $(C_1-C_4)$alkoxy, $(C_1-C_4)$alkoxycarbonyl, or $(C_3-C_4)$alkenyl;

a nitrogen oxide thereof, a prodrug of said compound or said nitrogen oxide; a pharmaceutically acceptable salt of said compound, said nitrogen oxide, or said prodrug, or a solvate or hydrate of said compound, said nitrogen oxide, said prodrug, or said salt.

9. A pharmaceutical composition comprising (1) a compound of claim 1, or 8; and (2) a pharmaceutically acceptable excipient, diluent, or carrier.

10. The pharmaceutical composition of claim 9, further comprising at least one other pharmaceutical agent selected from the group consisting of an apo-B/MTP inhibitor, an MCR-4 agonist, a CCK-A agonist, a monoamine reuptake inhibitor, a sympathomimetic agent, a $\beta_3$ adrenergic receptor agonist, a dopamine agonist, a melanocyte-stimulating hormone receptor analog, a cannabinoid 1 receptor antagonist, a melanin concentrating hormone antagonist, leptin, a leptin analog, a leptin receptor agonist, a galanin antagonist, a lipase inhibitor, a bombesin agonist, a neuropeptide-Y antagonist, a thyromimetic agent, dehydroepiandrosterone or an analog thereof, a glucocorticoid receptor agonist or antagonist, an orexin receptor antagonist, a urocortin binding protein antagonist, a glucagon-like peptide-1 receptor agonist, a ciliary neurotrophic factor, a human agouti-related protein, a ghrelin receptor antagonist, a histamine 3 receptor antagonist or reverse agonist, and a neuromedin U receptor agonist.

11. The pharmaceutical composition of claim 10 wherein said anti-obesity agent is selected from the group consisting of orlistat, sibutramine, bromocriptine, ephedrine, leptin, and pseudoephedrine.

* * * * *